United States Patent
Gunning et al.

(10) Patent No.: US 10,519,107 B2
(45) Date of Patent: Dec. 31, 2019

(54) SULFONAMIDE COMPOUNDS AND THEIR USE AS STAT5 INHIBITORS

(71) Applicant: Governing Council of the University of Toronto, Toronto (CA)

(72) Inventors: Patrick Thomas Gunning, Mississauga (CA); Abbarna A. Cumaraswamy, Etobicoke (CA); Andrew Martin Lewis, Mississauga (CA); Mulu Geletu-Heye, Mississauga (CA)

(73) Assignee: The Governing Council of the University of Toronto, Toronto (CA)

( * ) Notice: Subject to any disclaimer, the term of this patent is extended or adjusted under 35 U.S.C. 154(b) by 0 days.

(21) Appl. No.: 15/315,324

(22) PCT Filed: May 29, 2015

(86) PCT No.: PCT/CA2015/000348
§ 371 (c)(1),
(2) Date: Nov. 30, 2016

(87) PCT Pub. No.: WO2015/179956
PCT Pub. Date: Dec. 3, 2015

(65) Prior Publication Data
US 2017/0101369 A1 Apr. 13, 2017

Related U.S. Application Data

(60) Provisional application No. 62/005,308, filed on May 30, 2014.

(51) Int. Cl.
| | | |
|---|---|---|
| *C07C 311/19* | (2006.01) | |
| *C07D 233/64* | (2006.01) | |
| *C07D 307/14* | (2006.01) | |
| *C07D 307/52* | (2006.01) | |
| *C07D 333/20* | (2006.01) | |
| *A61K 31/63* | (2006.01) | |
| *A61K 31/13* | (2006.01) | |
| *A61K 31/025* | (2006.01) | |

(52) U.S. Cl.
CPC ......... *C07C 311/19* (2013.01); *C07D 233/64* (2013.01); *C07D 307/14* (2013.01); *C07D 307/52* (2013.01); *C07D 333/20* (2013.01); *C07C 2601/02* (2017.05); *C07C 2602/42* (2017.05)

(58) Field of Classification Search
CPC combination set(s) only.
See application file for complete search history.

(56) References Cited

U.S. PATENT DOCUMENTS

| | | | |
|---|---|---|---|
| 6,383,790 B1 | 5/2002 | Shokat | |
| 8,586,749 B2 | 11/2013 | Turkson et al. | |
| 8,846,707 B2 * | 9/2014 | Turkson | A61K 31/18 |
| | | | 514/275 |
| 8,895,746 B2 | 11/2014 | Turkson et al. | |
| 2009/0069420 A1 | 3/2009 | Turkson et al. | |
| 2012/0130079 A1 | 5/2012 | Turkson et al. | |
| 2016/0068478 A1 | 3/2016 | Turkson et al. | |

FOREIGN PATENT DOCUMENTS

| | | | | |
|---|---|---|---|---|
| AU | 2011285836 A2 | 11/2013 | | |
| CA | 2757912 A1 | 10/2010 | | |
| CA | 2807292 A1 | 2/2012 | | |
| CA | 2874057 | 11/2013 | | |
| JP | 2013-537535 A | 10/2013 | | |
| KR | 10-2013-0121818 A | 11/2013 | | |
| RU | 2009116653 A | 11/2010 | | |
| WO | WO-2010/117438 A2 | 10/2010 | | |
| WO | WO-2010/117438 A3 | 10/2010 | | |
| WO | WO-2012/018868 A1 | 2/2012 | | |
| WO | WO-2012018868 A1 * | 2/2012 | ............. | A61K 31/18 |
| WO | WO-2013177534 A2 | 11/2013 | | |
| WO | WO-2014070859 | 5/2014 | | |
| WO | WO-2014070859 A1 * | 5/2014 | ............. | C07F 9/3834 |
| WO | WO-2015179956 | 12/2015 | | |

OTHER PUBLICATIONS

U.S. Appl. No. 14/452,183, filed Aug. 2014, Turkson; James.*
Urlam et al. "Development of new N-arylbenzamides as STAT3 dimerization inhibitors." Med. Chem. Commun. 2013, 4, 932-941. (Year: 2013).*
"International Application No. PCT/CA2015/000348, International Search Report and Written Opinion dated Aug. 26, 2015", (dated Aug. 26, 2015), 12 pgs.
Urlam, Murali K., et al., "Development of new N-Arylbenzamides as STAT3 Dimerization Inhibitors", Medchemcomm. Jun. 2013 ; 4(6): 932-941, (Jun. 2013), 932-941.
"International Application No. PCT/CA2015/000348, Russian Search Report dated Dec. 10, 2018", (dated Dec. 10, 2018), 3 pgs.
Ando, Tomoaki, "Critical Role for Mast Cell Stat5 Activity in Skin Inflammation", Cell Rep. Jan. 30, 2014; 6(2): 366-376. doi:10.1016/j.celrep.2013.12.029, (Jan. 30, 2014), 366-376.
Furqan, M., et al., "STAT inhibitors for cancer therapy", Journal of Hematology & Oncology, 6(1), 90. doi:10.1186/1756-8722-6-90, (2013), 11 pgs.

(Continued)

*Primary Examiner* — Amanda L Aguirre
(74) *Attorney, Agent, or Firm* — Schwegman Lundberg & Woessner, P.A.

(57) ABSTRACT

The present disclosure relates to compounds having the Formula (Formula (I)) which are inhibitors of STAT5.

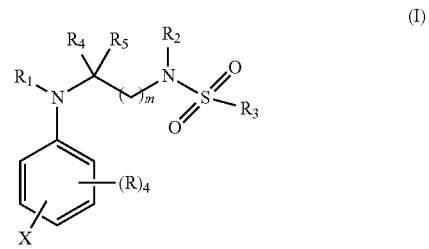

21 Claims, 20 Drawing Sheets
Specification includes a Sequence Listing.

(56) References Cited

OTHER PUBLICATIONS

Kawakami, Toshiaki, et al., "Hypothetical atopic dermatitis-myeloproliferative neoplasm syndrome", Frontiers in Immunology, vol. 6, Article 434, (Aug. 24, 2015), 4 pgs.
Lai, Ping-Shan, et al., "A STAT inhibitor patent review: progress since 2011", Expert Opinion on Therapeutic Patents, 25(12); DOI:10.1517/13543776.2015.1086749, (2015), 26 pgs.
Lauenborg, Britt, et al., "Malignant T cells express lymphotoxin a and drive endothelial activation in cutaneous T cell lymphoma", Oncotarget, vol. 6, No. 17, (Apr. 15, 2015), 15235-15249.
Mitra, Abhisek, et al., "Signal Transducer and Activator of Transcription 5b (Stat5b) Serine 193 Is a Novel Cytokine-induced Phospho-regulatory Site That Is Constitutively Activated in Primary Hematopoietic Malignancies", The Journal of Biological Chemistry vol. 287, No. 20, pp. 16596-16608, May 11, 2012, (May 11, 2012), 16596-16608.
Persson, Jenny Liao, "miRNA in mycosis fungoides and skin inflammation", APMIS 121: 1017-1019, (2013), 1017-1019.
Schartl, Manfred, et al., "A Mutated EGFR Is Sufficient to Induce Malignant Melanoma with Genetic Background-Dependent Histopathologies", Journal of Investigative Dermatology (2010) 130, 249-258; doi:10.1038/jid.2009.213, (Jul. 16, 2009), 249-258.
Yu, Hua, et al., "STATs in cancer inflammation and immunity: a leading role for STAT3", Nat Rev Cancer. Nov. 2009; 9(11): 798-809. doi:10.1038/nrc2734, (Nov. 2009), 798-809.
"U.S. Appl. No. 13/263,336, Notice of Allowance dated May 24, 2013", 7 pgs.
"U.S. Appl. No. 13/263,336, Notice of Allowance dated Aug. 8, 2013", 6 pgs.
"U.S. Appl. No. 13/263,336, Amendment filed Jul. 23, 2013 responsive to the Notice of Allowance dated May 24, 2013", 5 pgs.
"U.S. Appl. No. 14/076,247, Notice of Allowance dated Jun. 23, 2014", 6 pgs.
"U.S. Appl. No. 14/076,247, Preliminary Amendment filed Nov. 10, 2013", 8 pgs.
"Canadian Application Serial No. 2,807,292, Office Action dated Apr. 29, 2016", 4 pgs.
"Canadian Application Serial No. 2,807,292, Office Action dated Aug. 25, 2015", 4 pgs.
"Definition of Derivative", Merriam-Webster, [online]. [retrieved on Mar. 29, 2017]. Retrieved from the Internet: <https://www.merriam-webster.com/dictionary/derivative>, (2017), 13 pgs.
"European Application Serial No. 10761975.1, Noting Loss of Rights dated Apr. 23, 2013", 2 pgs.
"European Application Serial No. 10761975.1, Office Action dated Nov. 23, 2011", 2 pgs.
"European Application Serial No. 10761975.1, Response filed May 30, 2012 to Offrice Action dated Nov. 23, 2011", 5 pgs.
"European Application Serial No. 10761975.1, Supplemental European Search Report dated Aug. 1, 2012", 8 pgs.
"International Application Serial No. PCT/US11/46340, International Preliminary Report on Patentatbility dated Feb. 5, 2013", 9 pgs.
"International Application Serial No. PCT/US11/46340, International Search Report dated Dec. 19, 2011", 3 pgs.
"International Application Serial No. PCT/US11/46340, Written Opinion dated Dec. 19, 2011", 8 pgs.
"International Application Serial No. PCT/US2010/001021, International Preliminary Report on Patentability dated Oct. 11, 2011", 6 pgs.
"International Application Serial No. PCT/US2010/001021, International Search Report dated Jul. 13, 2011", 2 pgs.
"International Application Serial No. PCT/US2010/001021, Written Opinion dated Jul. 13, 2011", 5 pgs.
Abdulghani, Junaid, et al., "Stat3 Promotes Metastatic Progression of Prostate Cancer", The American Journal of Pathology, vol. 172, No. 6, (Jun. 2008), 1717-1728.
Akca, Hakan, et al., "Activation of the AKT and STAT3 pathways and prolonged survival by a mutant EGFR in human lung cancer cells", Lung Cancer, 54, (2006), 25-33.
Alimirah, Fatouma, et al., "DU-145 and PC-3 human prostate cancer cell lines express androgen receptor: Implications for the androgen receptor functions and regulation", FEBS Letters, 580, (2006), 2294-2300.
Almarsson, Orn, et al., "Crystal engineering of the composition of pharmaceutical phases. Do pharmaceutical co-crystals represent a new path to improved medicines?", Chem. Commun., 2004, (2004), 1889-1896.
Becker, Stefan, et al., "Three-dimensional structure of the Stat3β homodimer bound to DNA", Nature, 394, (1998), 145-151.
Berishaj, Marjan, et al., "Stat3 is tyrosine-phosphorylated through the interleukin-6/glycoprotein 130/Janus kinase pathway in breast cancer", Breast Cancer Research, 9:R32, (2007), 1-8.
Bhasin, Deepak, et al., "Design, synthesis, and studies of small molecule STAT3 inhibitors", Bioorganic & Medicinal Chemistry Letters 18, (2008), 391-395.
Blaskovich, Michelle A., et al., "Discovery of JSI-124 (Cucurbitacin I), a Selective Janus Kinase/Signal Transducer and Activator of Transcription 3 Signaling Pathway Inhibitor with Potent Antitumor Activity against Human and Murine Cancer Cells in Mice", Cancer Research, 63, (2003), 1270-1279.
Boulares, A. Hamid, et al., "Role of Poly(ADP-ribose) Polymerase (PARP) Cleavage in Apoptosis—Caspase 3-Resistant PARP Mutant Increases Rates of Apoptosis in Transfected Cells", J. Biol. Chem., 274(33), (1999), 22932-22940.
Bowman, Tammy, et al., "STATs in oncogenesis", Oncogene, 19, (2000), 2474-2488.
Bromberg, Jacqueline, "Signal transducers and activators of transription as regulators of growth, apoptosis and breast development", Breast Cancer Research, 2(2), (2000), 86-90.
Bromberg, Jacqueline, et al., "Stat3 as an Oncogene", Cell, vol. 98, (1999), 295-303.
Bromberg, Jacqueline, "The role of STATs in transcriptional control and their impact on cellular function", Oncogene, 19, (2000), 2468-2473.
Buettner, Ralf, et al., "Activated STAT Signaling in Human Tumors Provides Novel Molecular Targets for Therapeutic Intervention", Clinical Cancer Research, vol. 8, (Apr. 2002), 945-954.
Burke, William M., et al., "Inhibition of constitutively active Stat3 suppresses growth of human ovarian and breast cancer cells", Oncogene, 20, (2001), 7925-7934.
Byrn, Stephen R., et al., "Chapter 11 Hydrates and Solvates", In: Solid-State Chemistry of Drugs, Second Edition, SSCI, Inc., (1999), 233-242.
Carlesso, Nadia, et al., "Tyrosyl Phosphorylation and DNA Binding Activity of Signal Transducers and Activators of Transcription (STAT) Proteins in Hematopoietic Cell Lines Transformed by Bcr/Abl", J. Exp. Med., 183, (Mar. 1996), 811-820.
Carro, Maria S., et al., "he transcriptional network for mesenchymal transformation of brain tumours", Nature, 463(7279), (2010), 11 pgs.
Catlett-Falcone, Robyn, et al., "Constitutive Activation of Stat3 Signaling Confers Resistance to Apoptosis in Human U266 Myeloma Cells", Immunity, 10, (Jan. 1999), 105-115.
Chen, Jianyong, et al., "Design and synthesis of a new, conformationally constrained, macrocyclic small-molecule inhibitor of STAT3 via 'click chemistry'", Bioorganic & Medicinal Chemistry Letters, 17, (2007), 3939-3942.
Chen, Jianyong, et al., "Structure-Based Design of Conformationally Constrained, Cell-Permeable STAT3 Inhibitors", ACS Med. Chem. Lett., 1, (2010), 85-89.
Coleman IV, David R., et al., "Solid Phase Synthesis of Phosphopeptides Incorporating 2,2-Dimethyloxazolidine Pseudoproline Analogs: Evidencefor trans Leu-Pro Peptide Bonds in Stat3 Inhibitors", nternational Journal of Peptide Research and Therapeutics, vol. 14, No. 1, (Mar. 2008), 1-9.
Coleman, IV, David R., et al., "Investigation of the Binding Determinants of Phosphopeptides Targeted to the Src Homology 2 Domain of the Signal Transducer and Activator of Transcription 3. Development of a High-Affinity Peptide Inhibitor", J. Med. Chem., 48, (2005), 6661-6670.

(56) References Cited

OTHER PUBLICATIONS

Darnell, Jr., James E., et al., "The JAK-STAT Pathway: Summary of Initial Studies and Recent Advances", Recent Progress in Hormone Research, vol. 51, (1996), 391-404.
Darnell, Jr., James E., et al., "Transcription Factors as Targets for Cancer Therapy", Nature Rev. Cancer, 2, (2002), 740-749.
Darnell, Jr., James E., "Validating Stat3 in cancer therapy", Nature Medicine, 11(6), (Jun. 2005), 595-596.
Debonera, Fotini, et al., "Activation of Interleukin-6/STAT3 and Liver Regeneration Following Transplantation", Journal of Surgical Research, 96, (2001), 289-295.
Dourlat, Jennifer, et al., "New syntheses of tetrazolylmethylphenylalanine and O-malonyltyrosine as pTyr mimetics for the design of STAT3 dimerization inhibitors", Bioorganic & Medicinal Chemistry Letters, 17, (2007), 3943-3946.
Farr, Andrew G., et al., "Medullary Epithelial Cell Lines from Murine Thymus Constitutively Secrete IL-1 and Hematopoietic Growth Factors and Express Class II Antigens in Response to Recombinant Interferon-γ", Cellular Immunology, 119, (1989), 427-444.
Faruqi, Tatjana R., et al., "Rac1 mediates STAT3 activation by autocrine IL-6", Proc. Natl. Acad. Sci. USA, 98(16), (2001), 9014-9019.
Ferbeyre, G., et al., "The role of Stat5 transcription factors as tumor suppressors or oncogenes", Biochimica et Biophysica Acta, 1815, (2011), 104-114.
Filmus, Jorge, et al., "Epidermal Growth Factor Receptor Gene—Amplified MDA-468 Breast Cancer Cell Line and Its Nonamplified Variants", Molecular and Cellular Biology, 7(1), (1987), 251-257.
Fletcher, Steven, et al., "Antagonism of the Stat3-Stat3 Protein Dimer with Salicylic Acid Based Small Molecules", ChemMedChem, 6, (2011), 1459-1470.
Fletcher, Steven, et al., "Disruption of Transcriptionally Active Stat3 Dimers with Non-phosphorylated, Salicylic Acid-Based Small Molecules: Potent in vitro and Tumor Cell Activities", ChemBioChem, 10, (2009), 1959-1964.
Fletcher, Steven, et al., "Mild, efficient and rapid O-debenzylation of ortho-substituted phenols with trifluoroacetic acid", Tetrahedron Letters, 49, (2008), 4817-4819.
Fletcher, Steven, et al., "Molecular Approaches towards the Inhibition of the Signal Transducer and Activator of Transcription 3 (Stat3) Protein", NIH Public Access, Author Manuscript, Published in final edited form as: ChemMedChem. Aug. 2008 ; 3(8): 1159-1168. doi:10.1002/cmdc.200800123., (2008), 22 pgs.
Fletcher, Steven, et al., "Molecular disruption of oncogenic signal transducer and activator of transcription 3 (STAT3) protein", Biochem. Cell Biol., 87, (2009), 825-833.
Fuh, B., et al., "LLL-3 inhibits STAT3 activity, suppresses glioblastoma cell growth and prolongs survival in a mouse glioblastoma model", British Journal of Cancer, 100, (2009), 106-112.
Garcia, Roy, et al., "Constitutive activation of Stat3 by the Src and JAK tyrosine kinases participates in growth regulation of human breast carcinoma cells", Oncogene, 20, (2001), 2499-2513.
Gough, Daniel J., et al., "Mitochondrial Stat3 Supports Ras-Dependent Oncogenic Transformation", NIH Public Access, Author Manuscript, Published in final edited form as: Science. Jun. 26, 2009; 324(5935): 1713-1716. doi:10.1126/science.1171721., (2009), 11 pgs.
Gouilleux, Fabrice, et al., "Prolactin and Interleukin-2 Receptors in T Lymphocytes Signal through a MGF-STAT5-Like Transcription Factor", Endocrinology, 136(12), (1995), 5700-5708.
Gouilleux-Gruart, Valerie, et al., "Activated Stat Related Transcription Factors in Acute Leukemia", Leukemia & Lymphoma, 28(1-2), (Dec. 1997), 83-88.
Gouilleux-Gruart, Valerie, et al., "STAT-Related Transcription Factors Are Constitutively Activated in Peripheral Blood Cells From Acute Leukemia Patients", Blood, 87(5), (1996), 1692-1697.
Gritsko, Tanya, et al., "Persistent Activation of Stat3 Signaling Induces Survivin Gene Expression and Confers Resistance to Apoptosis in Human Breast Cancer Cells", Clin Cancer Res., 2(1), (2006), 11-19.
Grivennikov, Sergei, et al., "Dangerous liaisons: STAT3 and NF-κB collaboration and crosstalk in cancer", NIH Public Access, Author Manuscript, published in final edited form as: Cytokine Growth Factor Rev. Feb. 2010; 21(1): 11-19. doi:10.1016/j.cytogfr.2009.11. 005., (2010), 19 pgs.
Gunning, Patrick T., et al., "Isoform selective inhibition of STAT1 or STAT3 homo-dimerization via peptidomimetic probes: Structural recognition of STAT SH2 domains", Bioorganic & Medicinal Chemistry Letters, 17, (2007), 1875-1878.
Gunning, Patrick T., et al., "Targeting Protein-Protein Interactions: Suppression of Stat3 Dimerization with Rationally Designed Small-Molecule, Nonpeptidic SH2 Domain Binders", NIH Public Access, Author Manuscript, published in final edited form as: Chembiochem. Nov. 24, 2008; 9(17): 2800-2803. doi:10.1002/cbic.200800291., (2008), 22 pgs.
Haftchenary, Sina, et al., "Inhibiting aberrant Stat3 function with molecular therapeutics: a progress report", Anti-Cancer Drugs, 22(2), (2011), 115-127.
Harris, Timothy J., et al., "An In Vivo Requirement for STAT3 Signaling in TH17 Development and TH17-Dependent Autoimmunity", J Immunol.,179, (2007), 4313-4317.
Haura, Eric B., et al., "Mechanisms of Disease: insights into the emerging role of signal transducers and activators of transcription in cancer", Nature Clinical Practice Oncology, 2(6), (Jun. 2005), 315-324.
Huang, Chen, et al., "Inhibition of STAT3 activity with AG490 decreases the invasion of human pancreatic cancer cells in vitro", Cancer Sci., 97(12), (Dec. 2006), 1417-1423.
Inghirami, G., et al., "New and Old Functions of STAT3: A Pivitol Target for Individualized Treatment of Cancer", Cell Cycle, 4(9), (2005), 1131-1133.
Johnson, Paul J., et al., "Overexpressed pp60$^{c-src}$ Can Induce Focus Formation Without Complete Transformation of NIH 3T3 Cells", Molecular and Cellular Biology, 5(5), (May 1985), 1073-1083.
Jones, Gareth, et al., "Development and Validation of a Genetic Algorithm for Flexible Docking", Journal of Molecular Biology, 267(3), (1997), 727-748.
Kaptein, Allard, et al., "Dominant Negative Stat3 Mutant Inhibits Interleukin-6-induced Jak-STAT Signal Transduction", The Journal of Biological Chemistry, 271(11), (1996), 5961-5964.
Kelly, John J. P., et al., "Proliferation of Human Glioblastoma Stem Cells Occurs Independently of Exogenous Mitogens", Stem Cells, 27, (2009), 1722-1733.
Kopantzev, Yevgeny, et al., "IL-6 mediated activation of STAT3 bypasses Janus kinases in terminally differentiated B lineage cells", Oncogene, 21, (2002), 6791-6800.
Kortylewski, Marcin, et al., "Role of Stat3 in suppressing antitumor immunity", NIH Public Access, Author Manuscript, published in final edited form as: Curr Opin Immunol. Apr. 2008 ; 20(2): 228-233., (2008), 9 pgs.
Kortylewski, Marcin, et al., "Stat3 as a Potential Target for Cancer Immunotherapy", J Immunother., 30(2), (2007), 131-139.
Lai, Stephen Y., et al., "Defining the role of the JAK-STAT pathway in head and neck and thoracic malignancies: Implications for future therapeutics approaches", Drug Resistance Updates, 13, (2010), 67-78.
Liby, Karen, et al., "The SyntheticTriterpenoid CDDO-Imidazolide Suppresses STAT Phosphorylation and Induces Apoptosis in Myeloma and Lung Cancer Cells", Clin Cancer Res., 12(14), (2006), 4288-4293.
Lin, Li, et al., "A Novel Small Molecule, LLL12, Inhibits STAT3 Phosphorylation and Activities and Exhibits Potent Growth-Suppressive Activity in Human Cancer Cells", Neoplasia, 12(1), (Jan. 2010), 39-50.
Maegawa, Tomohiro, et al., "Pd/C(en) Catalyzed Chemoselective Hydrogenation in the Presence of Aryl Nitriles", Chem. Pharm. Bull., 55(5), (May 2007), 837-839.
Mandal, Pijus K., et al., "Solid phase synthesis of Stat3 inhibitors incorporating O-carbamoylserine and O-carbamoylthreonine as glu-

(56) References Cited

OTHER PUBLICATIONS tamine mimics", NIH Public Access, Author Manuscript, published in final edited form as: Bioorg Med Chem Lett. Feb. 1, 2007; 17(3): 654-656. doi:10.1016/j.bmcl.2006.10.099., (2007), 8 pgs.

Maritano, Diego, et al., "The STAT3 isoforms alpha and beta have unique and specific functions", Nature Immunology, 5(4), (Apr. 2004), 401-409.

Mashili, Fredirick, et al., "Constitutive STAT3 Phosphorylation Contributes to Skeletal Muscle Insulin Resistance in Type 2 Diabetes", Diabetes, vol. 62, (Feb. 2013), 457-465.

Miyamoto, Takeshi, et al., "STAT3 is critical to promote inflammatory cytokines and RANKL expression in inflammatory arthritis", Abstract P43, Arthritis Research & Therapy, vol. 14 Suppl 1, (2012), 38-39.

Mora, Linda B., et al., "Constitutive Activation of Stat3 in Human Prostate Tumors and Cell Lines: Direct Inhibition of Stat3 Signaling Induces Apoptosis of Prostate Cancer Cells", Cancer Research, 62, (2002), 6659-6666.

Muller, Judith, et al., "Discovery of Chromone-Based Inhibitors of the Transcription Factor STAT5", ChemBioChem, 9, (2008), 723-727.

Neculai, Dante, et al., "Structure of the Unphosphorylated STAT5a Dimer", J. Biol. Chem., 280(49), (2005), 40782-40787.

Niu, Guilian, et al., "Constitutive Stat3 activity up-regulates VEGF expression and tumor angiogenesis", Oncogene, 21, (2002), 2000-2008.

Ouyang, Hong, et al., "Immortal Human Pancreatic Duct Epithelial Cell Lines with Near Normal Genotype and Phenotype", American Journal of Pathology, 157(5), (Nov. 2000), 1623-1631.

Page, Brent D. G., et al., "Identification of a non-phosphorylated, cell permeable, small molecule ligand for the Stat3 SH2 domain", Bioorganic & Medicinal Chemistry Letters, 21, Fletcher, (2011), S605-S609.

Page, Brent D. G., et al., "Signal transducer and activator of transcription 3 inhibitors: a patent review", Expert Opin. Ther. Patents, 21(1), (2011), 65-83.

Page, Brent D. G., et al., "Small Molecule STAT5-SH2 Domain Inhibitors Exhibit Potent Antileukemia Activity", Journal of Medicinal Chemistry, 55, (2011), 1047-1055.

Pandey, Paras N., et al., "Palladium-Catalyzed Hydrodehalogenation of Haloaromatic Compounds", Synthesis, No. 10, (Oct. 1982), 876-878.

Pardanani, A., et al., "JAK inhibitor therapy for myelo?brosis: critical assessment of value and limitations", Leukemia, 25, (2011), 218-225.

Quintas-Cardama, Alfonso, et al., "Janus kinase inhibitors for the treatment of myeloproliferative neoplasias and beyond", Nature Reviews, vol. 10, (Feb. 2011), 127-140.

Razgulin, Andrew V., et al., "Binding Properties of Aromatic Carbon-Bound Fluorine", J. Med. Chem, 49, (2006), 7902-7906.

Real, Pedro J., et al., "Resistance to chemotherapy via Stat3-dependent overexpression of Bcl-2 in metastatic breast cancer cells", Oncogene, 21, (2002), 7611-7618.

Ren, Zhiyong, et al., "Identification of a High-Affinity Phosphopeptide Inhibitor of Stat3", Bioorganic & Medicinal Chemistry Letters, 13, (2003), 633-636.

Schlessinger, Karni, et al., "Malignant Transformation but not Normal Cell Growth Depends on Signal Transducer and Activator of Transcription 3", Cancer Res, 65(13), (2005), 5828-5834.

Schroder, Martina, et al., "Preassociation of nonactivated STAT3 molecules demonstrated in living cells using bioluminescence", Journal of Leukocyte Biology, vol. 75, (May 2004), 792-797.

Schroder, Martina, et al., "Preassociation of nonactivated STAT3 molecules demonstrated in living cells using bioluminescence resonance energy transfer: a new model of STAT activation?", Journal of Leukocyte Biology, vol. 75, (May 2004), 92-79.

Schust, Jochen, et al., "A high-throughput fluorescence polarization assay for signal transducer and activator of transcription 3", Analytical Biochemistry, 330, (2004), 114-118.

Schust, Jochen, et al., "Stattic: A Small-Molecule Inhibitor of STAT3 Activation and Dimerization", Chemistry & Biology 13, (Nov. 2006), 1235-1242.

Sehgal, Pravin B., et al., "Paradigm shifts in the cell biology of STAT signaling", NIH Public Access, published in final edited form as: Semin Cell Dev Biol. Aug. 2008 ; 19(4): 329-340. doi:10.1016/j.semcdb.2008.07.003., (2008), 26 pgs.

Seidel, H. Martin, et al., "Spacing of palindromic half sites as a determinant of selective STAT (signal transducers and activators of transcription) DNA binding and transcriptional activity", Proc. Natl. Acad. Sci. USA. 92, (Mar. 1995), 3041-3045.

Shahani, Vijay M., et al., "Design, Synthesis and in vitro Characterization of Novel Hybrid Peptidomimetic Inhibitors of STAT3 Protein", NIH Public Access, Author Manuscript, published in final edited form as: Bioorg Med Chem. Mar. 1, 2011; 19(5): 1823-1838. doi:10.1016/j.bmc.2010.12.010., (2011), 34 pgs.

Shahani, Vijay M., et al., "Identification of Purine-Scaffold Small-Molecule Inhibitors of Stat3 Activation by QSAR Studies", ACS Medicinal Chemistry Letters, (2011), 79-84.

Shuai, Ke, et al., "Interferon Activation of the Transcription Factor Stat91 Involves Dimerization through SH2-Phosphotyrosyl Peptide Interactions", Cell, vol. 76, (1994), 821-828.

Siddiquee, Khandaker, et al., "Selective chemical probe inhibitor of Stat3, identified through structure-based virtual screening, induces antitumor activity", Proc. Natl. Acad. Sci. USA, 104(18), (2007), 7391-7396.

Siddiquee, Khandaker A. Z., et al., "An Oxazole-Based Small-Molecule Stat3 Inhibitor Modulates Stat3 Stability and Processing and Induces Antitumor Cell Effects", ACS Chemical Biology, 2(12), gunning, (2007), 787-798.

Siddiquee, Khandaker Al Zaid, et al., "STAT3 as a target for inducing apoptosis in solid and hematological tumors", Cell Research, 18, (2008), 254-267.

Song, Hui, et al., "A low-molecular-weight compound discovered through virtual database screening inhibits Stat3 function in breast cancer cells", Proc. Natl. Acad. Sci. USA, 102(13), (2005), 4700-4705.

Sugimoto, Ken, "Role of STAT3 in inflammatory bowel disease", World J. Gastroenterology, 14(33), (2008), 5110-5114.

Sun, Jiazhi, "Cucurbitacin Q: a selective STAT3 activation inhibitor with potent antitumor activity", Oncogene, 24, (2005), 3236-3245.

Tan, Shyh-Han, et al., "Signal transducer and activator of transcription 5A/B in prostate and breast cancers", Endocrine-Related Cancer, 15, (2008), 367-390.

Turkson, James, et al., "A Novel Platinum Compound Inhibits Constitutive Stat3 Signaling and Induces Cell Cycle Arrest and Apoptosis of Malignant Cells", The Journal of Biological Chemistry, 280(38), (2005), 32979-32988.

Turkson, James E., et al., "Inhibition of constitutive signal transducer and activator of transcription 3 activation by novel platinum complexes with potent antitumor activity", Molecular Cancer Therapeutics, (Dec. 2004), 1533-1542.

Turkson, James, et al., "Novel peptidomimetic inhibitors of signal transducer and activator of transcription 3 dimerization and activator of transcription 3 dimerization and biological activity", Molecular Cancer Therapeutics, (2004), 261-269.

Turkson, James, et al., "Phosphotyrosyl Peptides Block Stat3-mediated DNA Binding Activity, Gene Regulation, and Cell Transformation", The Journal of Biological Chemistry, 276(48), (2001), 45443-45455.

Turkson, James, et al., "Requirement for Ras/Rac1-Mediated p38 and c-Jun N-Terminal Kinase Signaling in Stat3 Transcriptional Activity Induced by the Src Oncoprotein", Molecular and Cellular Biology, 19(11), (1999), 7519-7528.

Turkson, James, et al., "STAT proteins as novel targets for cancer drug discovery", Expert Opin. Ther. Targets, 8(5), (2004), 409-422.

Turkson, James, et al., "STAT proteins: novel molecular targets for cancer drug discovery", Oncogene, 19, (2000), 6613-6626.

Turkson, James, et al., "Stat3 Activation by Src Induces Specific Gene Regulation and Is Required for Cell Transformation", Molecular and Cellular Biology, 18(5), (May 1998), 2545-2552.

(56) References Cited

OTHER PUBLICATIONS

Urlam, Murali K., et al., "Development of new N-Arylbenzamides as STAT3 Dimerization Inhibitors", NIH Public Access, published in final edited form as: Medchemcomm; 4(6), (2013), 932-941, (2013), 19 pgs.

Valerio, Christine, et al., "Regioselective Chlorocarbonylation of Polybenzyl Cores and Functionalization Using Dendritic and Organometallic Nucleophiles", . Org. Chem., 65, (2000), 1996-2002.

Van De Waterbeemd, Han, et al., "Property-Based Design: Optimization of Drug Absorption and Pharmacokinetics", Journal of Medicinal Chemistry, 44(9), (2011), 1313-1333.

Vippagunta, Sudha R., et al., "Crystalline Solids", Adv Drug Deliv Rev., 48(1), (May 16, 2001), 3-26.

Wagner, Markus, "Enhanced Expression of the Type II Transforming Growth Factor-B Receptor Is Associated with Decreased Survival in Human Pancreatric Cancer", Pancreas, 19(4), (1999), 370-376.

Wang, Chen, et al., "Expression of a Retinoic Acid Receptor Gene in Myeloid Leukemia Cells", Leukemia, 3(4), (1989), 264-269.

Wang, Tianhong, et al., "Regulation of the innate and adaptive immune responses by Stat-3 signaling in tumor cells", Nature Medicine, 10(1), (2004), 48-54.

Wang, X., et al., "KLF8 promotes human breast cancer cell invasion and metastasis by transcrigtional activation of MMP9", Oncogene, 30, (2011), 1901-1911.

Weber-Nordt, R. M., et al., "Constitutive activation of STAT proteins in primary lymphoid and myeloid leukemia cells and in Epstein-Barr virus (EBV)-related lymphoma cell lines", Blood, 88(3), (1996), 809-816.

Wei, Daoyan, et al., "Stat3 activation regulates the expression of vascular endothelial growth factor and human pancreatic cancer angiogenesis and metastasis", Oncogene, 22, (2003), 319-329.

Weimbs, Thomas, et al., "Regulation of STATs by polycystin-1 and their role in polycystic kidney disease", JAK-STAT, 2:2, e23650, (2013), 9 pgs.

Wu, Pengguang, et al., "A High-Throughput STAT Binding Assay Using Fluorescence Polarization", Analytical Biochemistry, 249, (1997), 29-36.

Xie, Tong-Xin, et al., "Stat3 activation regulates the expression of matrix metalloproteinase-2 and tumor invasion and metastasis", Oncogene, 23, Wei, (2004), 3550-3560.

Yang, Jinbo, et al., "Novel Roles of Unphosphorylated STAT3 in Oncogenesis and Transcriptional Regulation", Cancer Res, 65(3), (2005), 939-947.

Yu, Chao-Lan, et al., "Enhanced DNA-binding activity of a Stat3-related protein in cells transformed bv the Src oncoprotein", Science, 269(5220), (1995), 4 pgs.

Yu, Hua, et al., "The STATs of Cancer—New Molecular Targets Come of Age", Nature Reviews, 4, (Feb. 2004), 97-105.

Yue, Peibin, et al., "Targeting STAT3 in cancer: how successful are we?", NIH Public Access, Author Manuscript, Published in final edited form as: Expen Opin Investig Drugs, 18(1), (2009), 45-56, (2009), 18 pgs.

Zhang, Guohong, et al., "Early Detection of Apoptosis Using a Fluorescent Conjugate of Annexin V", BioTechniques, 23(3), (1997), 525-531.

Zhang, Sheng, et al., "PTP1B as a drug target: recent developments in PTP1B inhibitor discovery", Drug Discovery Today, Viol. 12, Issues 9-10, (May 2007), 373-381.

Zhang, Xiaolei, et al., "A novel small-molecule disrupts Stat3 SH2 domain-phosphotyrosine interactions and Stat3-dependent tumor processes", Biochemical Pharmacology, 79, (2010), 1398-1409.

Zhang, Yi, et al., "Activation of Stat3 in v-Src-transformed Fibroblasts Requires Cooperation of Jak1 Kinase Activity", J. Biol. Chem., 275, (2000), 24935-24944.

Zhao, Shujie, et al., "Inhibition of STAT Tyr705 Phosphorylation by Smad4 Suppresses Transforming Growth Factor B-Mediated Invasion and Metastasis in Pancreatic Cancer Cells", Cancer Res, 68(11), (2008), 4221-4228.

Zhao, Wei, et al., "A Cell-permeable Stat3 SH2 Domain Mimetic Inhibits Stat3 Activation and Induces Antitumor Cell Effects in Vitro", J. Biol. Chem., 285, (2010), 35855-35865.

"European Application No. 15800248.5, Extended European Search Report dated Oct. 16, 2017", (dated Oct. 16, 2017), 8 pgs.

Page, Brent D.G., et al., "Inhibiting Aberrant Signal Transducer and Activator of Transcription Protein Activation with Tetrapodal, Small Molecule Src Homology 2 Domain Binders: Promising Agents against Multiple Myeloma", J. Med. Chem 2013, 56, 7190-7200, (Aug. 22, 2013), 7190-7200.

Hermanson, Greg T., *Bioconjugate Techniques*, Third Edition, Academic Press, Elsevier Inc., (2013), 1139 pgs.

\* cited by examiner

A)

B)

C)

| Compound | Remaining Percentages @ 60 minutes (%) | |
|---|---|---|
| | HLS9 | MMLS9 |
| Verapamil | 16.92 | 15.86 |
| AC 3-019 | 59.82 | 6.96 |
| AM 1-020 | 11.76 | 24.69 |
| DR 3-093 | 13.79 | 0.82 |
| SH4-054 | 39.18 | 2.88 |

SULFONAMIDE COMPOUNDS AND THEIR USE AS STAT5 INHIBITORS

PRIORITY CLAIM TO RELATED APPLICATIONS

This application is a U.S. national stage application filed under 35 U.S.C. § 371 from International Application Serial No. PCT/CA2015/000348, which was filed 29 May 2015, and published as WO2015/179956 on 3 Dec. 2015, and which claims priority to U.S. Provisional Application No. 62/005,308, filed 30 May 2014, which applications and publication are incorporated by reference as if reproduced herein and made a part hereof in their entirety, and the benefit of priority of each of which is claimed herein.

FIELD

The present disclosure relates to compounds which are inhibitors of the STAT5 protein, including compounds of the Formula (I).

INTRODUCTION

Numerous inhibitors have been developed to target the JAK-STAT signaling pathway, a major driving force in hematopoietic malignancies. While emphasis has focused on identifying effective upstream kinase inhibitors for suppressing STAT activity, inhibitors have suffered from poor kinase selectivity[1], cardiovascular toxicity[2,3], and in some clinical cases, acquired resistance.[4] Multiple kinase inhibitors have been used in combination to try to combat resistance.[5,6] An alternative strategy to reduce off-target toxicity, is to target proteins immediately downstream of the kinases, such as the Signal Transducer and Activator of Transcription (STAT) 5 protein.

In normal cells, the activation of STAT5 proteins are tightly regulated by cytokines (IL-2, IL-5, IL-7, GM-CSF, erythropoietin (EPO), thrombopoietin, and prolactin) and growth factors.[7] Binding of these extracellular ligands to their target receptors induces the activation of receptor-associated JAK kinases that phosphorylate key tyrosine residues within the receptor, providing docking sites for the SRC homology 2 (SH2) domains of the inactive cytoplasmic STAT5 monomers. STAT5 is then phosphorylated at specific tyrosine residues, either Y694 (STAT5A) or Y699 (STAT5B) of the C-terminus. Phosphorylated STAT5 monomers form either homo- or hetero-[8,9] STAT5X-STATX dimers through reciprocal phosphotyrosine-SH2 interactions. Activated STAT5 dimers translocate to the nucleus where they bind to STAT5 DNA response elements inducing transcription of genes involved in proliferation (Bcl-xl, c-Myc, pim-1), cell differentiation (p21), cell survival (MCL-1) inflammation (Osm) and apoptosis (JAB).[10] In contrast, mutations within cytosolic kinases (TEL-JAK2, Bcr-Abl, FLT-3) as well as overactive receptor associated tyrosine kinases (SRC, EGFR) induces constitutive phosphorylation of STAT5 proteins increasing the production of anti-apoptotic genes which can contribute to driving the cancer phenotype.[11]

Approaches aimed at directly targeting STAT5 have been limited to a chromone-derived acyl hydrazine inhibitor, identified through a high-throughput fluorescence polarization (FP) screen. While this agent exhibited promising in vitro disruption of the STAT5:EPOR phosphopeptide interaction, higher concentrations were required to inhibit STAT5 in cells.[12]

SUMMARY

In one embodiment, the present disclosure relates to compounds of the Formula (I) which are inhibitors of the STAT5 protein. In one embodiment, the compound of the Formula (I) has the following structure

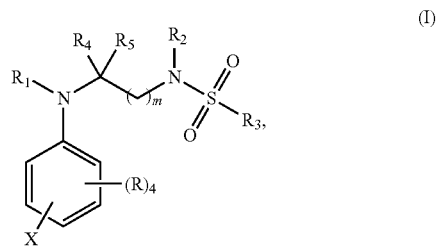

wherein
$R_1$ is —$(CH_2)_n$—$(C_6$-$C_{10})$-aryl or —C(=O)—$(CH_2)_n$—$(C_6$-$C_{10})$-aryl, wherein the aryl groups are optionally substituted with one to five substituents selected from halo, OH, $(C_1$-$C_6)$-alkyl, $(C_1$-$C_6)$-alkoxy, halo-substituted-$(C_1$-$C_4)$-alkyl, -(cyclopropyl)-$CF_3$, —$NO_2$, CN, —$SO_3R'$ and —COOR', wherein R' is H or $(C_1$-$C_4)$-alkyl;
$R_2$ is —$(CH_2)_n$—$(C_6$-$C_{10})$-aryl, wherein the aryl groups are optionally substituted with one to five substituents selected from halo, OH, $(C_1$-$C_6)$-alkyl, $(C_1$-$C_6)$-alkoxy, halo-substituted-$(C_1$-$C_4)$-alkyl, -(cyclopropyl)-$CF_3$, —$NO_2$, ON, —$SO_3R'$ and —COOR', wherein R' is H or $(C_1$-$C_4)$-alkyl;
$R_3$ is —$(CH_2)_n$—$(C_6$-$C_{10})$-aryl, wherein the aryl groups are optionally substituted with one to five substituents selected from halo, OH, $(C_1$-$C_6)$-alkyl, $(C_1$-$C_6)$-alkoxy, halo-substituted-$(C_1$-$C_4)$-alkyl, -(cyclopropyl)-$CF_3$, —$NO_2$, ON, —$SO_3R'$ and —COOR', wherein R' is H or $(C_1$-$C_4)$-alkyl;
X is —COOR", —P(O)(OR")$_2$, tetrazole, —C(=O)NR"—OH, or —$CF_2OH$, wherein R" is H or $(C_1$-$C_4)$-alkyl;
$R_4$ and $R_5$ are H, or taken together $R_4$ and $R_5$ are —C(=O);
R is H, OH, halo, $(C_1$-$C_6)$-alkyl or $(C_1$-$C_6)$-alkoxy;
n is 0, 1, 2, 3, 4, 5, or 6; and
m is 1, 2, 3 or 4;
or a pharmaceutically acceptable salt, solvate, prodrug and/or stereoisomer thereof.

The present disclosure also includes pharmaceutical compositions comprising compounds of the disclosure and pharmaceutically acceptable excipients, carriers and/or additives.

In one embodiment, the compounds of the disclosure are inhibitors of the STAT5 protein. In an aspect of the disclosure, the compounds of the Formula (I) are useful for treating or preventing conditions of a condition or disease mediated by the STAT5 protein. In another embodiment, the condition or disease is hematopoietic malignancies, skin conditions, non-melanoma skin cancer, prostate cancer or inflammation.

Other features and advantages of the present application will become apparent from the following detailed description. It should be understood, however, that the detailed description and the specific examples while indicating preferred embodiments of the application are given by way of illustration only, since various changes and modifications within the spirit and scope of the application will become apparent to those skilled in the art from this detailed description.

DRAWINGS

The disclosure will now be described in greater detail with reference to the following drawings in which.

Figure 8:
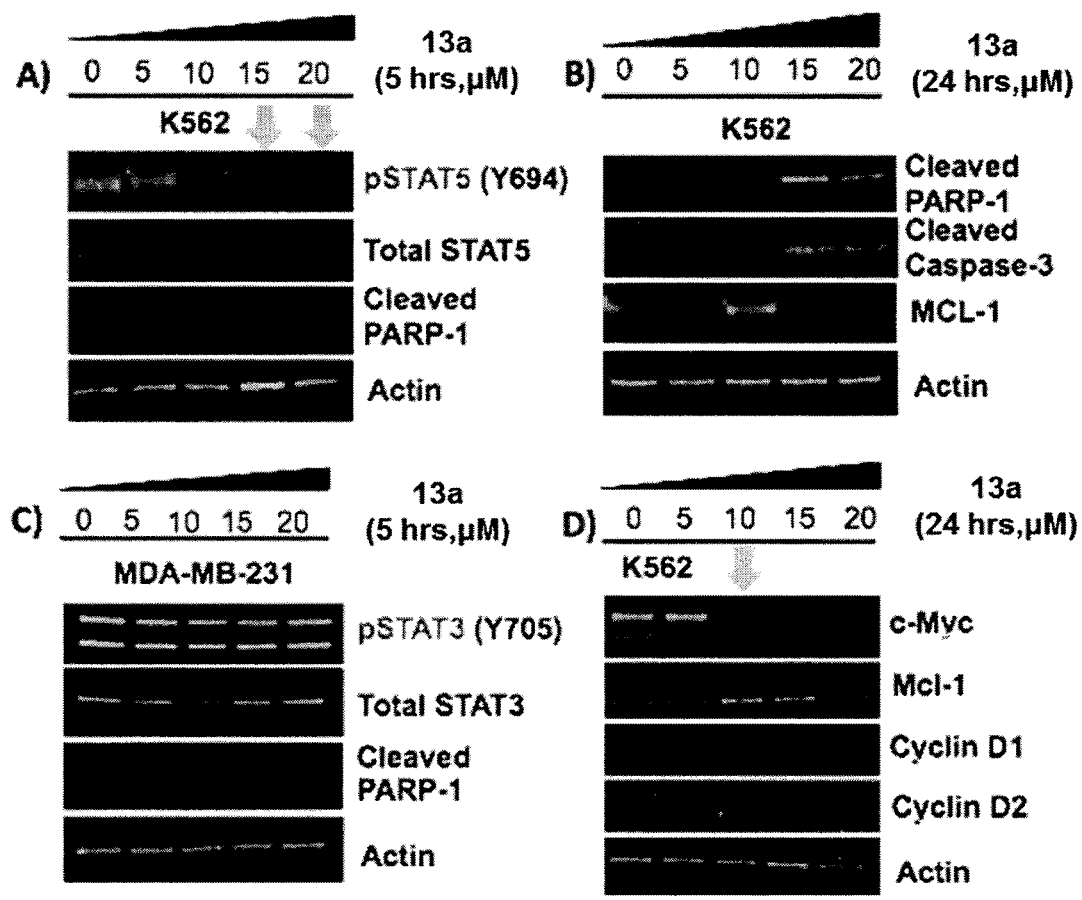
Figure 9:
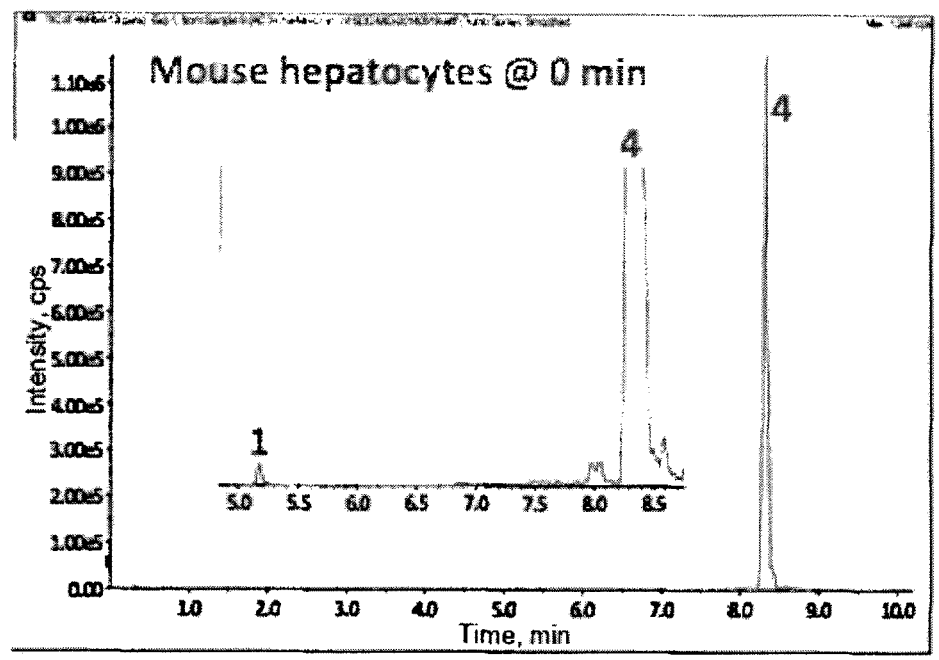
Figure 9:
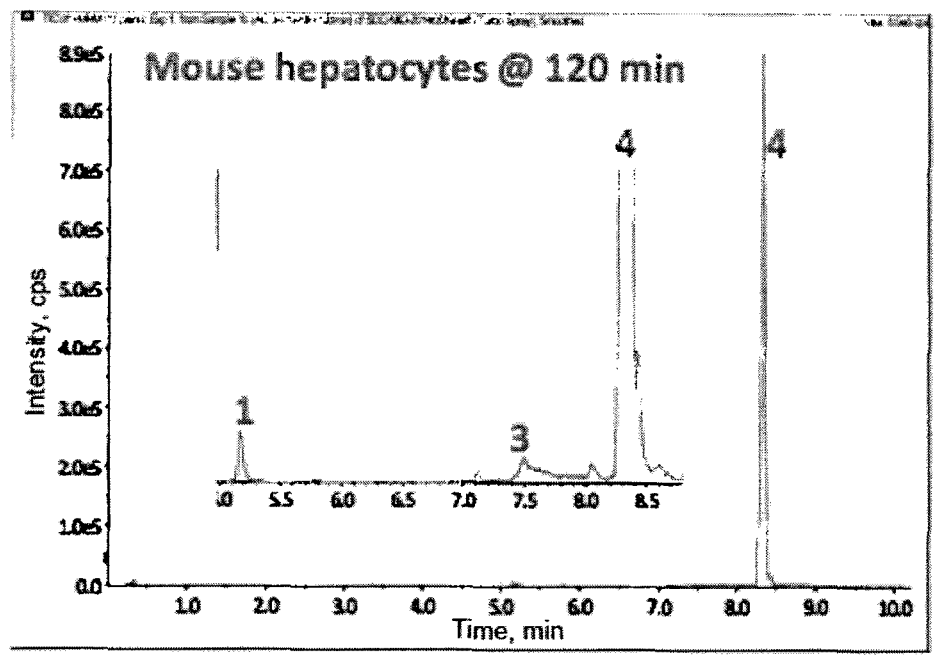
Figure 9:
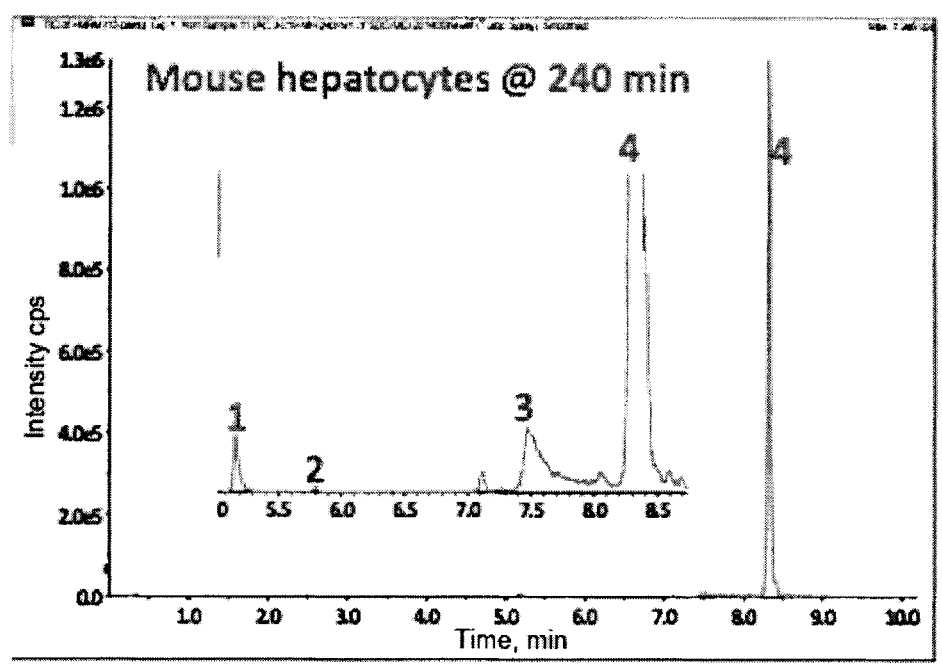
Figure 10:
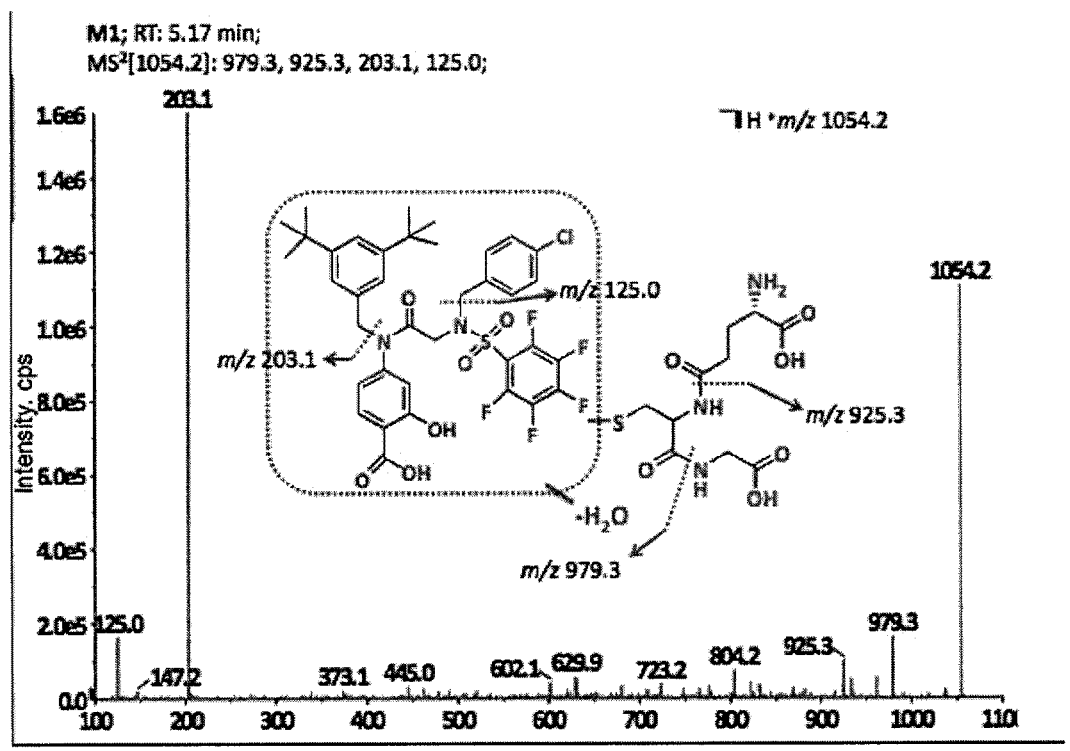
Figure 11:
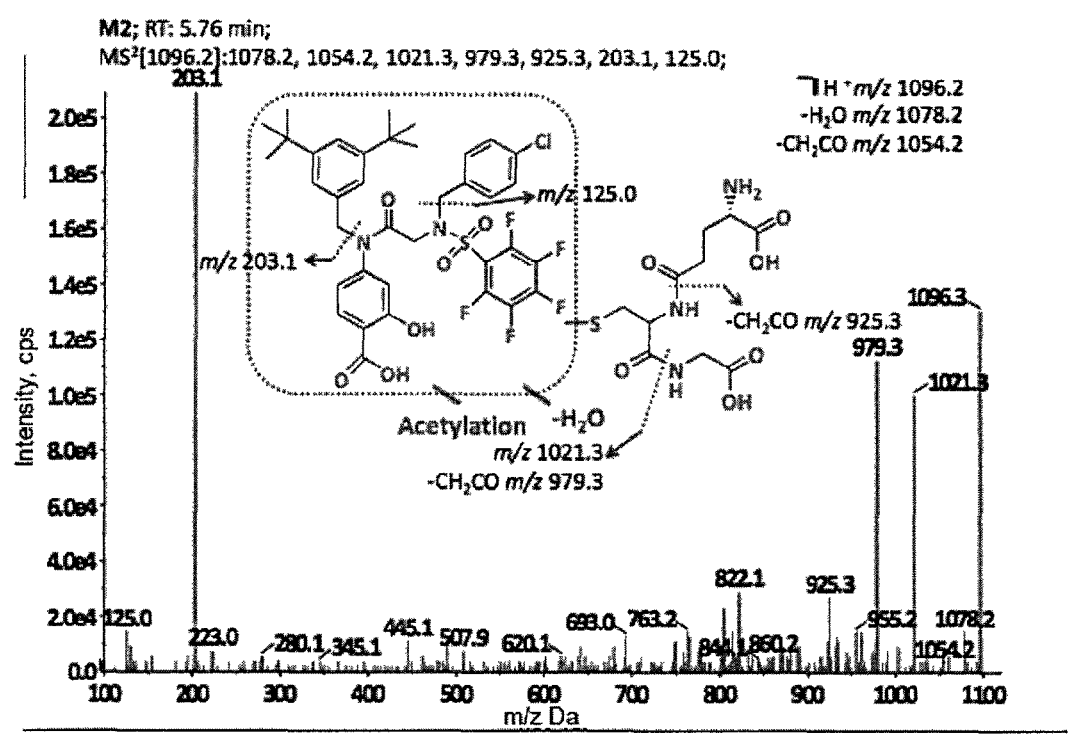
Figure 12:
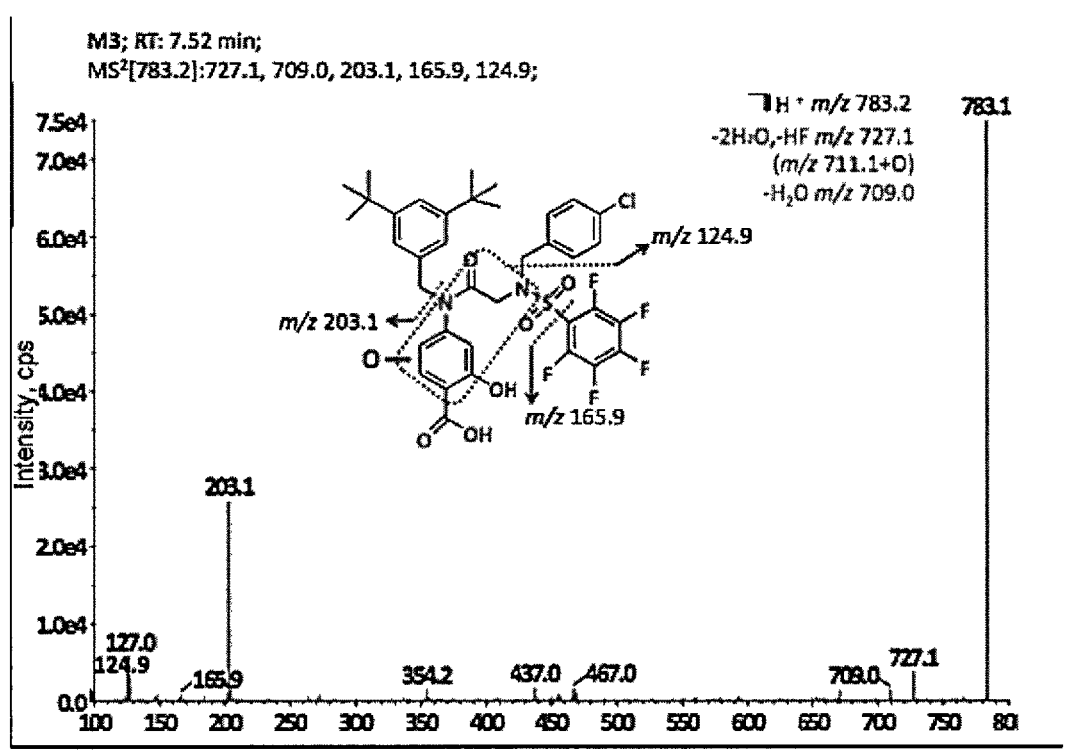
Figure 13:
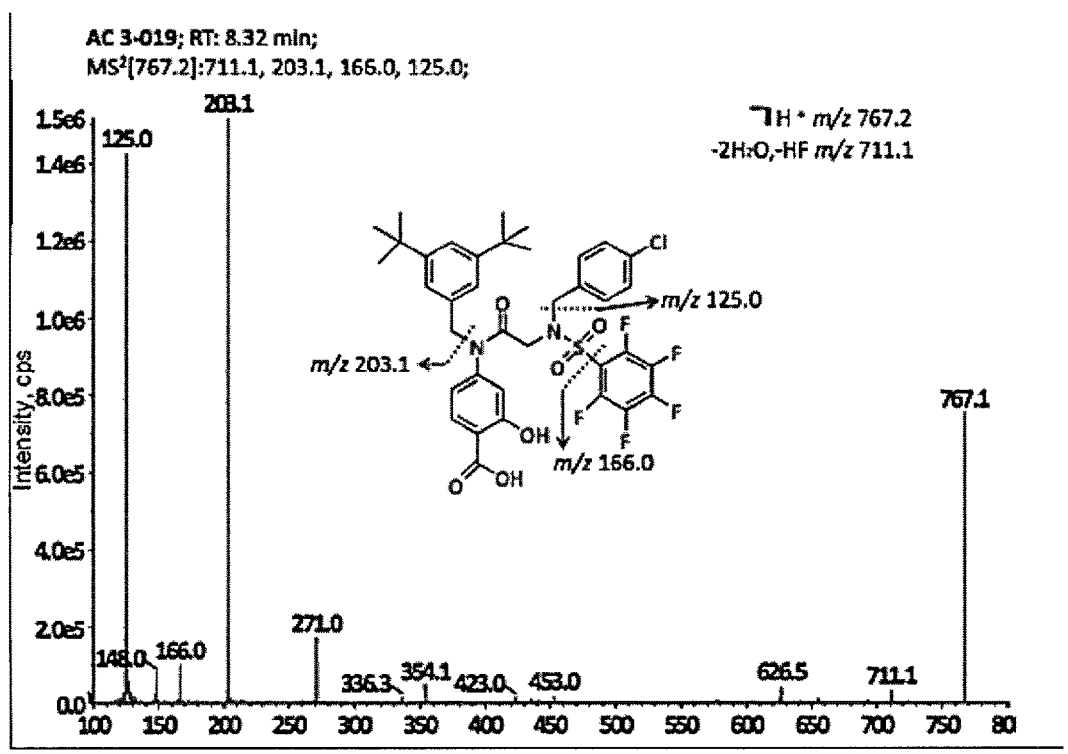
Figure 14:
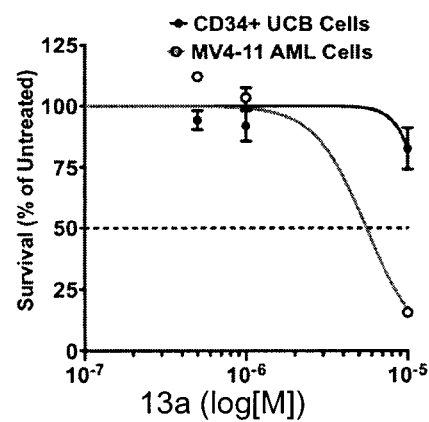

FIG. 8 is a graph showing A) Inhibition of pSTAT5 with a compound of the disclosure in K562 cells; B) Initiation of apoptosis after 24 hrs and knockdown of MCL-1; C) the compound shows no effect on pSTAT3 in MDA-MB-231 cells up to 20 µM; and D) knockdown of downstream target c-Myc after 5 hrs;

FIG. 9 shows a series of LC-MS spectra showing the metabolic stability in mouse hepatocytes of a compound of the disclosure at various time points: A) 0 min; B) 120 min; and C) 240 min;

FIG. 10 shows a tandem mass spectra of a first peak from the LC-MS spectra of FIG. 9;

FIG. 11 shows a tandem mass spectra of a second peak from the LC-MS spectra of FIG. 9;

FIG. 12 shows a tandem mass spectra of a third peak from the LC-MS spectra of FIG. 9;

FIG. 13 shows a tandem mass spectra of a fourth peak from the LC-MS spectra of FIG. 9; and FIG. 14 shows the effects of a compound of the disclosure on CD34+ and MV4-11 AML cells.

Figure 15:
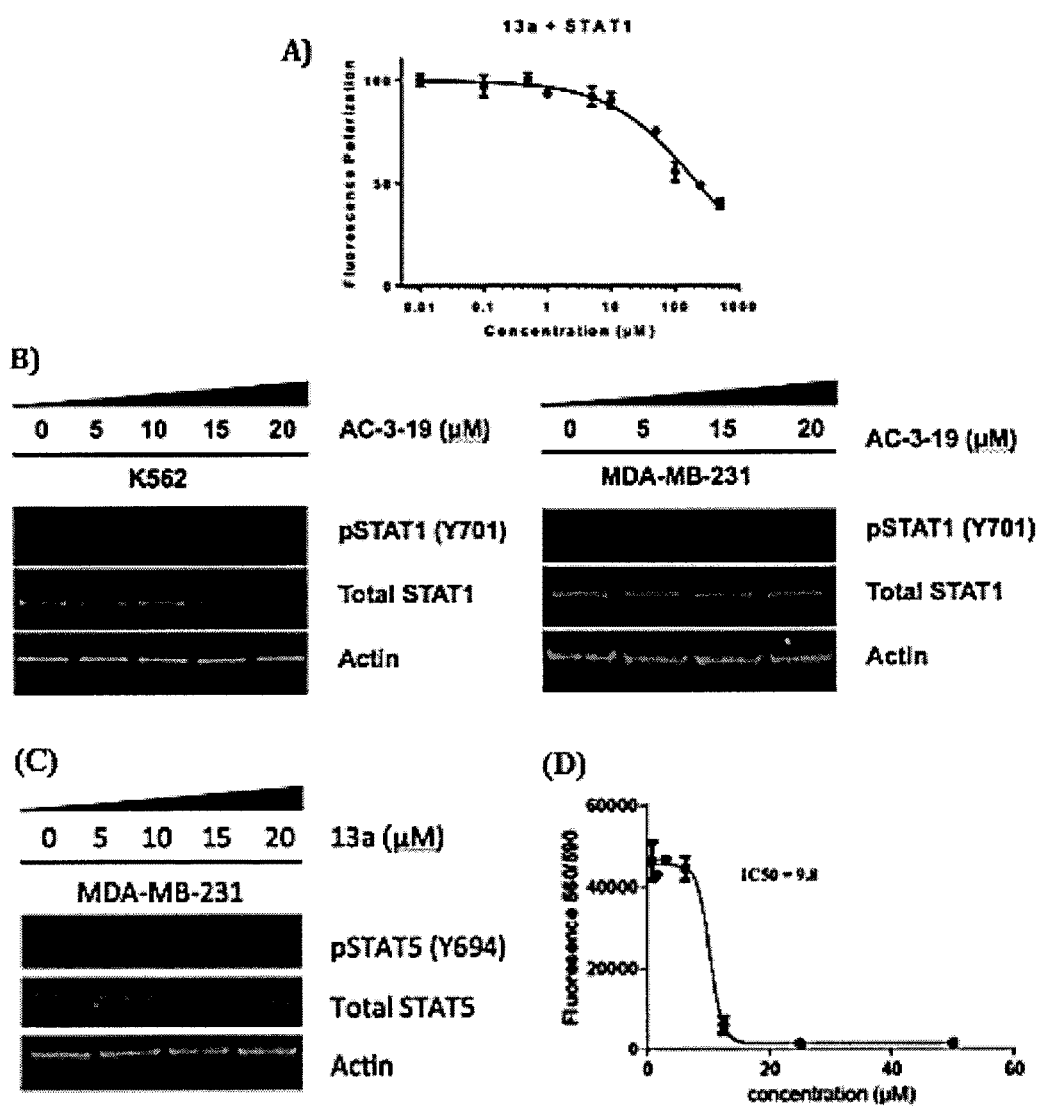

FIG. 15 shows A) a normalized FP curve displaying the competitive binding of a compound of the disclosure to wildtype STAT1 protein; B) Effect of a compound of the disclosure on the phosphorylation levels of STAT1 in K562 and MDA-MB-231 cells; C) Phosphorylation levels of STAT5 within MDA-MB-231 cells. D) Cell viability of a compound of the disclosure in MDA-MB-231 cells.

Figure 16:
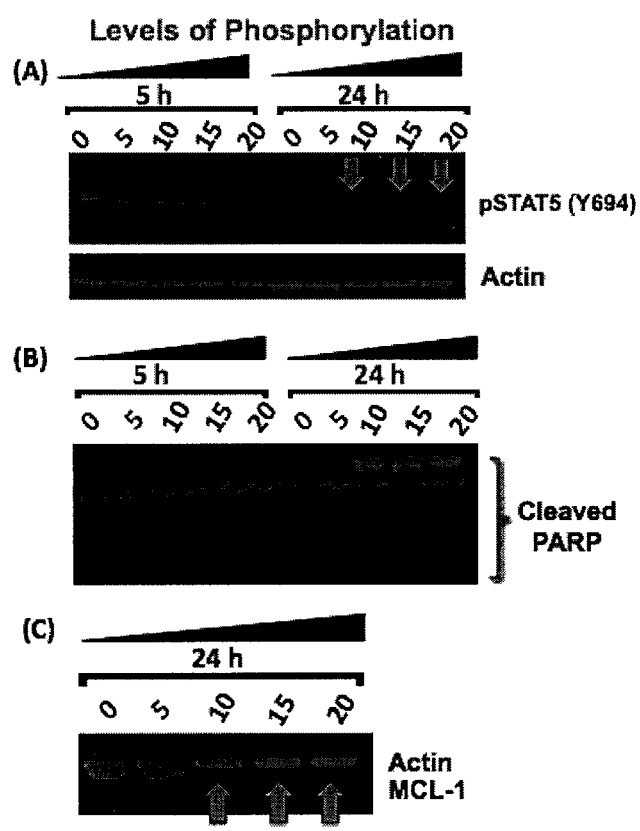

FIG. 16 shows A) Inhibition of pSTAT5 with a compound of the disclosure (10 µM, yellow arrows) in MV-4; 11 cells at 5 and 24 h; B) After 24 h, apoptosis was initiated by the detectable cleaved PARP-1; C) a compound of the disclosure induced complete knockdown of downstream target gene, MCL-1 at 10 µM.

Figure 17:
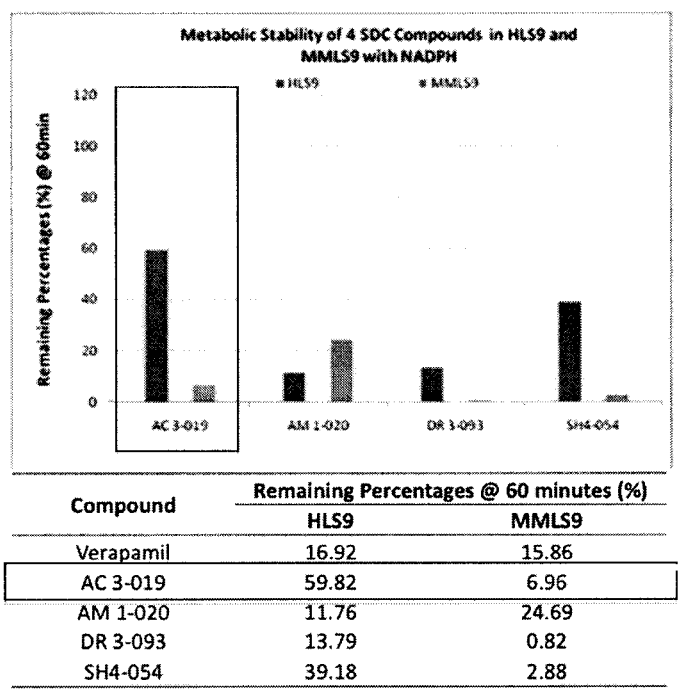

FIG. 17 shows the metabolic stability of a compound of the disclosure in HLS9 and MMLS9 with NADPH at 60 min.

Figure 18:
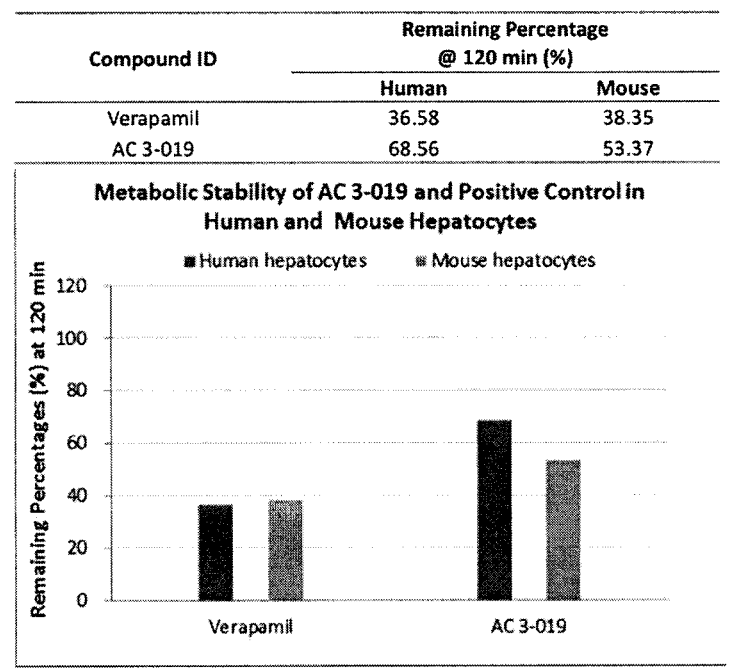

FIG. 18 shows A) the metabolic stability of a compound of the disclosure and positive control (verapamil) in human and mouse hepatocytes at 120 min. B) Remaining percentages of the compound and positive control (verapamil) in boiled human and mouse hepatocytes at 120 min as the negative control.

Figure 19:
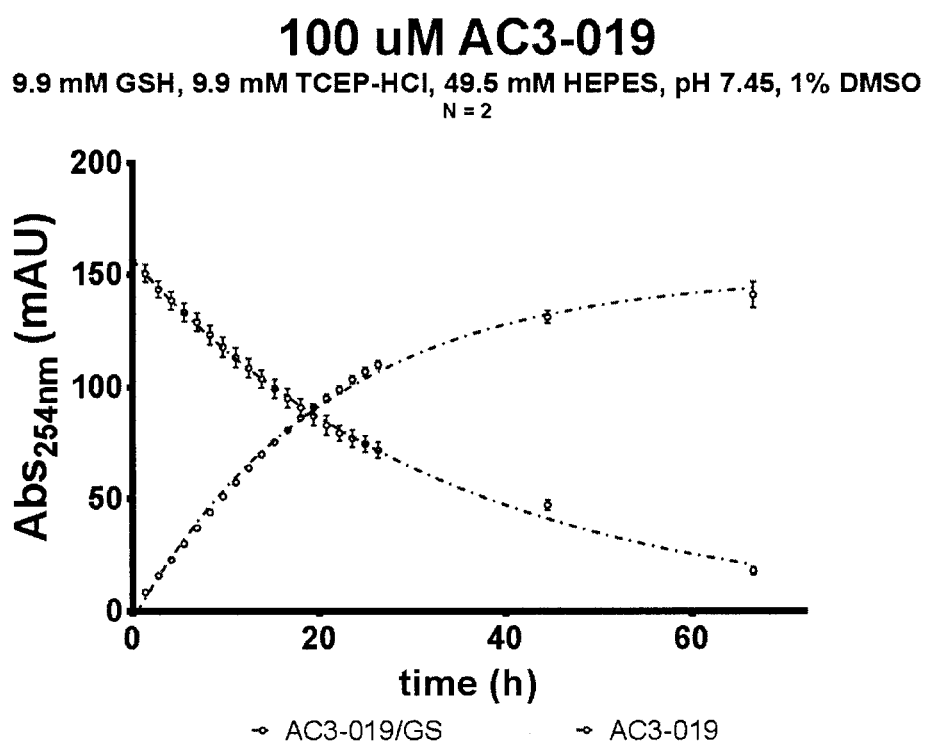

FIG. 19 shows a single phase decay fit for the analytical HPLC data points of a compound of the disclosure in the presence of excess glutathione tripeptide (10 mM).

DESCRIPTION OF VARIOUS EMBODIMENTS

Definitions

The term "($C_1$-$C_p$)-alkyl" as used herein means straight and/or branched chain, saturated alkyl radicals containing from one to "p" carbon atoms and includes (depending on the identity of p) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable p is an integer representing the largest number of carbon atoms in the alkyl radical.

The term "($C_1$-$C_p$)-alkoxy" means an alkyl group, as defined above, having an oxygen atom attached thereto. As used herein, the term means straight and/or branched chain, saturated alkyl radicals having an oxygen atom attached thereto and containing from one to "p" carbon atoms and includes (depending on the identity of p) methoxy, ethoxy, propoxy, isopropoxy, n-butoxy, s-butoxy, isobutoxy, t-butoxy, 2,2-dimethylbutoxy, n-pentoxy, 2-methylpentoxy, 3-methylpentoxy, 4-methylpentoxy, n-hexoxy and the like, where the variable p is an integer representing the largest number of carbon atoms in the alkoxy radical.

The term "halo-substituted-($C_1$-$C_p$)-alkyl" as used herein means straight and/or branched chain, saturated alkyl radicals containing from one to "p" carbon atoms, in which at least one, and up to and including all, of the hydrogen atoms have been replaced with halogen atoms and includes (depending on the identity of p) fluoromethyl, difluoromethyl, trifluoromethyl, chloromethyl, dichloromethyl, trichloromethyl, 1-fluoroethyl, 1,1-difluoroethyl and the like, where the variable p is an integer representing the largest number of carbon atoms in the alkyl radical.

The term "aryl" as used herein refers to cyclic groups that contain at least one aromatic ring, for example a single ring (e.g. phenyl) or multiple condensed rings (e.g. naphthyl). In an embodiment of the present disclosure, the aryl group contains 6, 9 or 10 atoms such as phenyl, naphthyl, indanyl, anthracenyl, 1,2-dihydronaphthyl, 1,2,3,4-tetrahydronaphthyl, fluorenyl, indanyl, indenyl and the like.

The term "halo" as used herein refers to a halogen atom and includes fluorine (F), chlorine (Cl), bromine (Br) and iodine (I).

The term "pharmaceutically acceptable salt" refers, for example, to a salt that retains the desired biological activity of a compound of the present disclosure and does not impart undesired toxicological effects thereto; and may refer to an acid addition salt or a base addition salt.

The term "solvate" as used herein means a compound or its pharmaceutically acceptable salt, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions.

In embodiments of the present disclosure, the compounds may have an asymmetric center. These compounds exist as enantiomers. Where compounds possess more than one asymmetric center, they may exist as diastereomers. It is to be understood that all such isomers and mixtures thereof in any proportion are encompassed within the scope of the present disclosure. It is to be further understood that while the stereochemistry of the compounds may be as shown in any given compound listed herein, such compounds may also contain certain amounts (e.g. less than 20%, suitably less than 10%, more suitably less than 5%) of compounds of the disclosure having alternate stereochemistry. For example, compounds of the disclosure that are shown without any stereochemical designations are understood to be racemic mixtures (i.e. contain an equal amount of each possible enantiomer or diastereomer). However, it is to be understood that all enantiomers and diastereomers are included within the scope of the present disclosure, including mixtures thereof in any proportion.

The term "effective amount" or "therapeutically effective amount" or "pharmaceutically effective amount" as used herein means an amount effective, at dosages and for periods of time necessary to achieve the desired result. For example in the context of treating a subject with a disease mediated by STAT5, an effective amount is an amount that, for example, inhibits the STAT5 protein in the subject. Effective amounts may vary according to factors such as the disease state, age, sex and/or weight of the subject. The amount of a given compound that will correspond to such an amount will vary depending upon various factors, such as the given drug or compound, the pharmaceutical formulation, the route of administration, the type of condition, disease or disorder, the identity of the subject being treated, and the like, but can nevertheless be routinely determined by one skilled in the art.

As used herein, the term "prodrug" refers to a substance that is prepared in an inactive form that is converted to an active form (i.e., drug) within the body or cells thereof by the action of, for example, endogenous enzymes or other chemicals and/or conditions. Prodrug derivatives of the compounds of the disclosure or pharmaceutically acceptable salts or solvates thereof, can be prepared by methods known to those of ordinary skill in the art, and include esters of any free hydroxyl or carboxyl moieties of the compounds.

As used herein, a "subject" refers to all members of the animal kingdom including mammals, and suitably refers to humans. A member of the animal kingdom includes, without limitation, a mammal (such as a human, primate, swine, sheep, cow, equine, horse, camel, canine, dog, feline, cat, tiger, leopard, civet, mink, stone marten, ferret, house pet, livestock, rabbit, mouse, rat, guinea pig or other rodent, seal, whale and the like), fish, amphibian, reptile, and bird (such as water fowl, migratory bird, quail, duck, goose, poultry, or chicken). In an embodiment of the present disclosure, the subject is in need of a compound or composition of the disclosure.

Compounds of the Disclosure

In one embodiment, the present disclosure relates to compounds of the Formula (A), which are STAT5 inhibitors. In one embodiment, the compound of the Formula (A) has the following structure

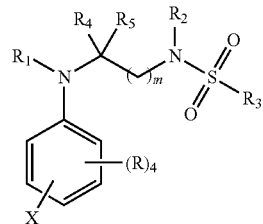

(A)

wherein $R_1$ is —$(CH_2)_n$—$(C_6$-$C_{10})$-aryl or —C(=O)—$(CH_2)_n$—$(C_6$-$C_{10})$-aryl, wherein the aryl groups are optionally substituted with one to five substituents selected from halo, OH, $(C_1$-$C_6)$-alkyl, $(C_1$-$C_6)$-alkoxy, halo-substituted-$(C_1$-$C_4)$-alkyl, -(cyclopropyl)-$CF_3$, —$NO_2$, CN, —$SO_3R'$ and —COOR', wherein R' is H or $(C_1$-$C_4)$-alkyl;

$R_2$ is —$(CH_2)_n$—$(C_6$-$C_{10})$-aryl, wherein the aryl groups are optionally substituted with one to five substituents selected from halo, OH, $(C_1$-$C_6)$-alkyl, $(C_1$-$C_6)$-alkoxy, halo-substituted-$(C_1$-$C_4)$-alkyl, -(cyclopropyl)-$CF_3$, —$NO_2$, CN, —$SO_3R'$ and —COOR', wherein R' is H or $(C_1$-$C_4)$-alkyl;

$R_3$ is —$(CH_2)_n$—$(C_6$-$C_{10})$-aryl, wherein the aryl groups are optionally substituted with one to five substituents selected from halo, OH, $(C_1$-$C_6)$-alkyl, $(C_1$-$C_6)$-alkoxy, halo-substituted-$(C_1$-$C_4)$-alkyl, -(cyclopropyl)-$CF_3$, —$NO_2$, CN, —$SO_3R'$ and —COOR', wherein R' is H or $(C_1$-$C_4)$-alkyl;

X is —COOR", —P(O)(OR")$_2$, tetrazole, —C(=O)NR"—OH, or —$CF_2OH$, wherein R" is H or $(C_1$-$C_4)$-alkyl or —$(CH_2)$—$(C_6$-$C_{10})$-aryl;

$R_4$ and $R_5$ are independently or simultaneously H or $CF_3$ wherein at least one of $R_4$ or $R_5$ is H, or taken together $R_4$ and $R_5$ are —C(=O) or —C(=S);

R is H, OH, halo, $(C_1$-$C_6)$-alkyl or $(C_1$-$C_6)$-alkoxy;

each n is independently or simultaneously 0, 1, 2, 3, 4, 5, or 6; and m is 1, 2, 3 or 4;

or a pharmaceutically acceptable salt, solvate, prodrug and/or stereoisomer thereof.

In one embodiment, the compound of the Formula (A) is a compound of the Formula (I) which are STAT5 inhibitors. In one embodiment, the compound of the Formula (I) has the following structure

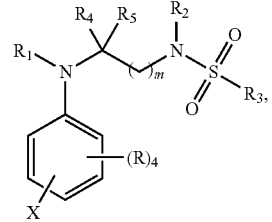

(I)

wherein $R_1$ is —$(CH_2)_n$—$(C_6$-$C_{10})$-aryl or —C(=O)—$(CH_2)_n$—$(C_6$-$C_{10})$-aryl, wherein the aryl groups are optionally substituted with one to five substituents selected from halo, OH, $(C_1$-$C_6)$-alkyl, $(C_1$-$C_6)$-alkoxy, halo-substituted-($C_1$-$C_4$)-alkyl, -(cyclopropyl)-$CF_3$, —$NO_2$, CN, —$SO_3R'$ and —COOR', wherein R' is H or ($C_1$-$C_4$)-alkyl;

$R_2$ is —$(CH_2)_n$—($C_6$-$C_{10}$)-aryl, wherein the aryl groups are optionally substituted with one to five substituents selected from halo, OH, ($C_1$-$C_6$)-alkyl, ($C_1$-$C_6$)-alkoxy, halo-substituted-($C_1$-$C_4$)-alkyl, -(cyclopropyl)-$CF_3$, —$NO_2$, CN, —$SO_3R'$ and —COOR', wherein R' is H or ($C_1$-$C_4$)-alkyl;

$R_3$ is —$(CH_2)_n$—($C_6$-$C_{10}$)-aryl, wherein the aryl groups are optionally substituted with one to five substituents selected from halo, OH, ($C_1$-$C_6$)-alkyl, ($C_1$-$C_6$)-alkoxy, halo-substituted-($C_1$-$C_4$)-alkyl, -(cyclopropyl)-$CF_3$, —$NO_2$, ON, —$SO_3R'$ and —COOR', wherein R' is H or ($C_1$-$C_4$)-alkyl;

X is —COOR'', —P(O)(OR'')$_2$, tetrazole, —C(=O)NR''—OH, or —$CF_2$OH, wherein R'' is H or ($C_1$-$C_4$)-alkyl;

$R_4$ and $R_5$ are H, or taken together $R_4$ and $R_5$ are —C(=O);

R is H, OH, halo, ($C_1$-$C_6$)-alkyl or ($C_1$-$C_6$)-alkoxy;

each n is independently or simultaneously 0, 1, 2, 3, 4, 5, or 6; and m is 1, 2, 3 or 4;

or a pharmaceutically acceptable salt, solvate, prodrug and/or stereoisomer thereof.

In one embodiment of the disclosure, $R_1$ is —($C_6$-$C_{10}$)-aryl, —($CH_2$)—($C_6$-$C_{10}$)-aryl or —C(=O)—($C_6$-$C_{10}$)-aryl. In another embodiment, $R_1$ is phenyl, naphthyl, —$CH_2$—phenyl, —$CH_2$-naphthyl, —C(=O)-phenyl or —C(=O)-naphthyl.

In another embodiment of the disclosure, the optional substituents on the aryl group of $R_1$ are selected from one to five of halo, CN, ($C_1$-$C_6$)-alkyl, halo-substituted-($C_1$-$C_4$)-alkyl and ($C_1$-$C_6$)-alkoxy. In another embodiment of the disclosure, the optional substituents on the aryl group of $R_1$ are selected from one to five of halo, ($C_1$-$C_6$)-alkyl and ($C_1$-$C_6$)-alkoxy. In another embodiment, the optional substituents on the aryl group of $R_1$ are selected from one to five of fluoro, chloro, bromo, ($C_1$-$C_4$)-alkyl or ($C_1$-$C_4$)-alkoxy. In a further embodiment, the optional substituents on the aryl group of $R_1$ are selected from one to three substituents selected from fluoro, methyl and t-butyl. In one embodiment, the optional substituents on the aryl group of $R_1$ are selected from one to three substituents selected from CN, —$CF_3$, —$CH_3$, F, isopropyl and t-butyl.

In one embodiment of the disclosure, the $R_1$ moiety is

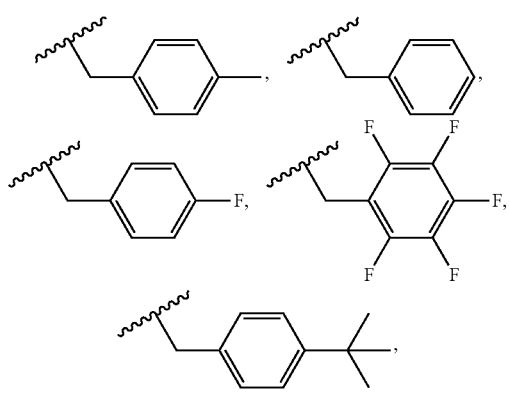

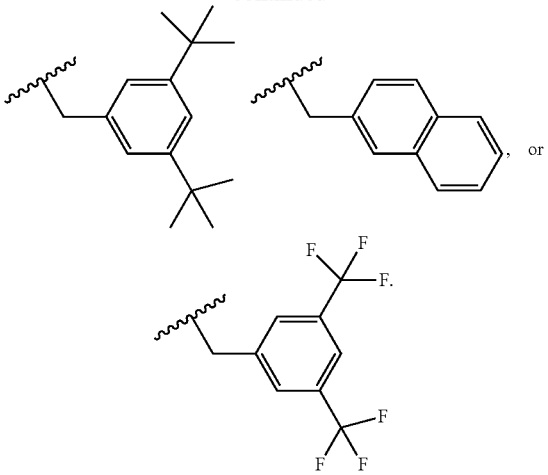

In another embodiment, the $R_1$ moiety is

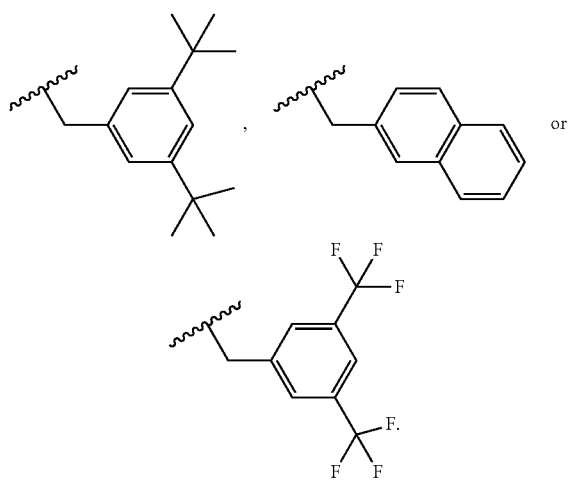

In another embodiment, the $R_1$ moiety is

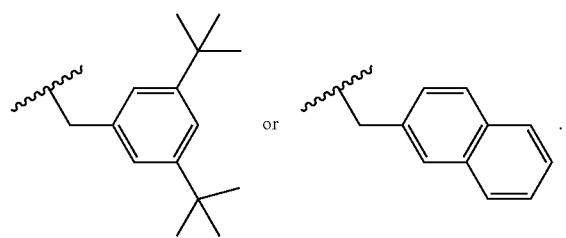 [SMILES: *Cc1cc(C(C)(C)C)cc(C(C)(C)C)c1 ; *Cc1ccc2ccccc2c1]

In one embodiment of the disclosure, $R_2$ is —($C_6$-$C_{10}$)-aryl or —($CH_2$)—($C_6$-$C_{10}$)-aryl. In another embodiment, $R_2$ is phenyl or —$CH_2$-phenyl.

In another embodiment, the optional substituents on the aryl group of $R_2$ are selected from one to five of halo, halo-substituted-($C_1$-$C_4$)-alkyl, -(cyclopropyl)-$CF_3$, —$NO_2$, CN, —$SO_3R'$ and —COOR', wherein R' is H or ($C_1$-$C_4$)-alkyl. In another embodiment, the optional substituents on the aryl group of $R_2$ are selected from one to three of halo, halo-substituted-($C_1$-$C_4$)-alkyl, and -(cyclopropyl)-$CF_3$. In another embodiment, the optional substituents on the aryl group of $R_2$ are one to three chloro groups, $CF_3$, or -(cyclopropyl)-$CF_3$.

In another embodiment, the $R_2$ moiety is

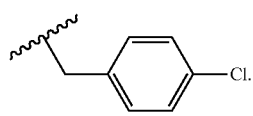 [SMILES: *Cc1ccc(Cl)cc1]

In another embodiment of the disclosure, $R_3$ is —($C_6$-$C_{10}$)-aryl or —($CH_2$)—($C_6$-$C_{10}$)-aryl. In another embodiment, $R_3$ is phenyl or —$CH_2$-phenyl.

In one embodiment, the optional substituents on the aryl group of $R_3$ are selected from one to five of halo, OH, ($C_1$-$C_6$)-alkyl, and ($C_1$-$C_6$)-alkoxy. In another embodiment, the optional substituents on the aryl group of $R_3$ are selected from one to five of fluoro, chloro, bromo, OH, ($C_1$-$C_3$)-alkyl, and ($C_1$-$C_3$)-alkoxy. In another embodiment, the optional substituents on the aryl group of $R_3$ are selected from one to five of fluoro, chloro, bromo, and ($C_1$-$C_3$)-alkyl.

In one embodiment, the $R_3$ moiety is

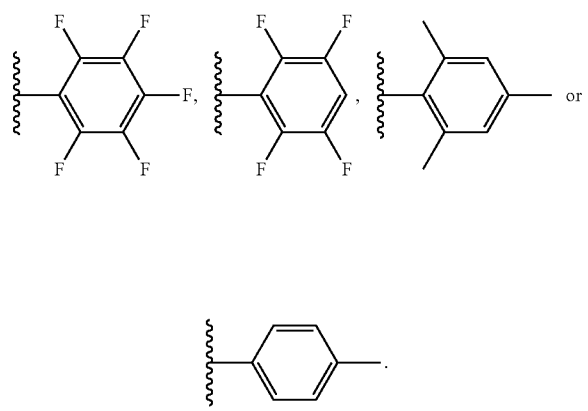

In another embodiment, the $R_3$ moiety is

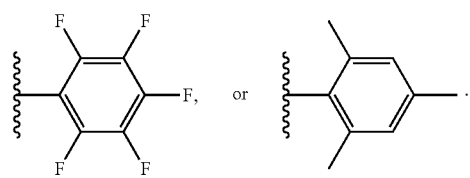

In a further embodiment of the disclosure, R is H, OH, fluoro, chloro, bromo, or ($C_1$-$C_4$)-alkyl. In another embodiment, H, F or OH.

In another embodiment of the disclosure, X is COOR", —P(O)(OR")$_2$ or tetrazole, wherein R" is H, or ($C_1$-$C_4$)-alkyl (such as t-butyl). In one embodiment, X is —COOR", wherein R" is H or ($C_1$-$C_4$)-alkyl. In one embodiment, X is —COOH. In one embodiment, X is —COO-benzyl.

In another embodiment of the disclosure, the compound of the Formula (I) has the following structure

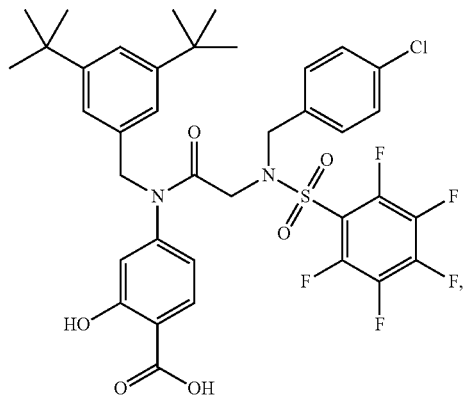
(13a)

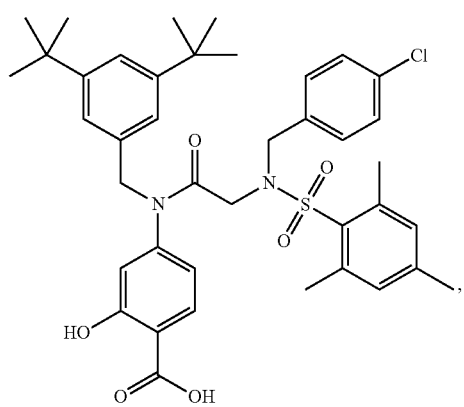
(13b)

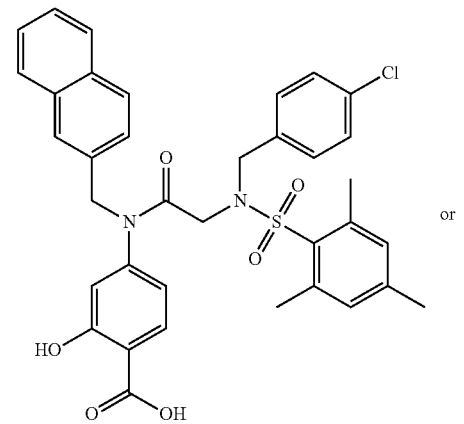
(13c)

-continued

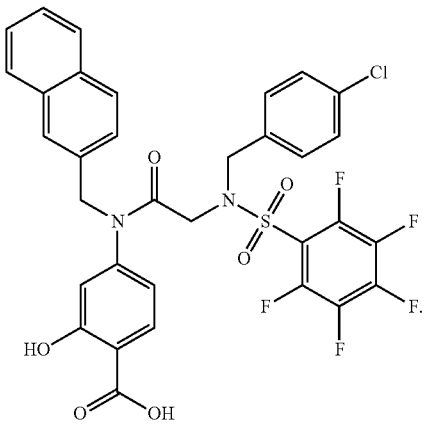

In a further embodiment, the compound of the Formula (I) has the following structure

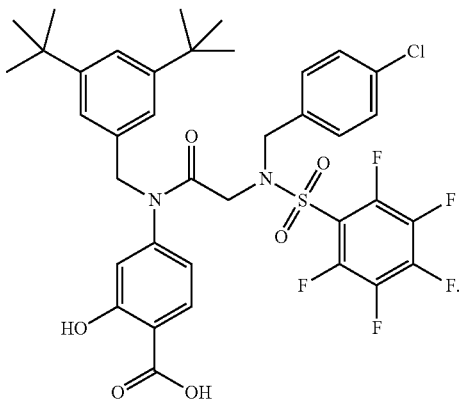 [SMILES: CC(C)(C)c1cc(CN(C(=O)CN(Cc2ccc(Cl)cc2)S(=O)(=O)c2c(F)c(F)c(F)c(F)c2F)c2ccc(C(=O)O)c(O)c2)cc(C(C)(C)C)c1]

In another embodiment of the disclosure, the compound of the Formula (I) is a compound of the Formula (I.A)

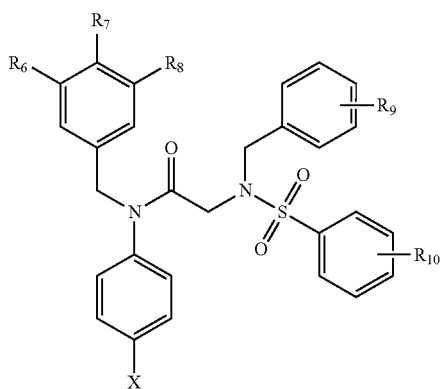

(I.A)

wherein
$R_6$, $R_7$ and $R_8$ are independently or simultaneously selected from H, halo, OH, $(C_1-C_6)$-alkyl, $(C_1-C_6)$-alkoxy, halo-substituted-$(C_1-C_4)$-alkyl, -(cyclopropyl)-$CF_3$, —$NO_2$, CN, —$SO_3R'$ and —COOR', wherein R' is H or $(C_1-C_4)$-alkyl; $R_9$ and $R_{10}$ are independently or simultaneously selected from one to five of halo, OH, $(C_1-C_6)$-alkyl, $(C_1-C_6)$-alkoxy, halo-substituted-$(C_1-C_4)$-alkyl, -(cyclopropyl)-$CF_3$, —$NO_2$, CN, —$SO_3R'$ and —COOR', wherein R' is H or $(C_1-C_4)$-alkyl;
X is —COOR", —P(O)(OR")$_2$, tetrazole, —C(=O)NR"—OH, or —$CF_2OH$, wherein R" is H, $(C_1-C_4)$-alkyl, or —$CH_2$—$(C_6-C_{10})$aryl;
or a pharmaceutically acceptable salt, solvate, prodrug and/or stereoisomer thereof.

In another embodiment of the disclosure, $R_6$, $R_7$ and $R_8$ are independently or simultaneously selected from H, halo, CN, $(C_1-C_6)$-alkyl, halo-substituted-$(C_1-C_4)$-alkyl and $(C_1-C_6)$-alkoxy. In another embodiment of the disclosure, $R_6$, $R_7$ and $R_8$ are independently or simultaneously selected from H, halo, CN, $CF_3$, $(C_1-C_6)$-alkyl and $(C_1-C_6)$-alkoxy. In another embodiment, $R_6$, $R_7$ and $R_8$ are independently or simultaneously selected from H, fluoro, chloro, bromo, CN, $CF_3$, $(C_1-C_4)$-alkyl or $(C_1-C_4)$-alkoxy. In one embodiment, $R_6$, $R_7$ and $R_8$ are independently or simultaneously selected from H, CN, —$CF_3$, —$CH_3$, F, isopropyl and t-butyl. In another embodiment, $R_6$ and $R_8$ are independently or simultaneously selected from H, CN, —$CF_3$, $(C_1-C_4)$-alkyl (such as —$CH_3$, isopropyl or t-butyl). In one embodiment, $R_6$ and $R_8$ are t-butyl and $R_7$ is H.

In one embodiment, $R_9$ and $R_{10}$ are independently or simultaneously selected from one to five of halo, OH, $(C_1-C_6)$-alkyl, $(C_1-C_6)$-alkoxy, or halo-substituted-$(C_1-C_4)$-alkyl. In one embodiment, $R_9$ and $R_{10}$ are independently or simultaneously selected from one to five of Cl, F, Br, OH, or $(C_1-C_6)$-alkyl. In one embodiment, $R_9$ is Cl in the para-position. In another embodiment, $R_{10}$ is five fluoro atoms. In another embodiment, $R_{10}$ is four fluoro atoms in the ortho- and meta-positions. In another embodiment, $R_{10}$ is three methyl groups in the ortho and para-positions.

In one embodiment, X is —COOR", wherein R" is H, $(C_1-C_4)$-alkyl, or —$CH_2$—$(C_6-C_{10})$aryl. In one embodiment, X is —COOH, —COO(t-butyl) or —COO-benzyl. In another embodiment, X is —COOH.

Compositions

The present disclosure also includes pharmaceutical compositions comprising a compound of the Formula (A), (I) and (I.A) as defined above (compounds of the disclosure), or pharmaceutically acceptable salts, solvates, and prodrugs thereof, and a pharmaceutically acceptable carrier or diluent. The compounds are suitably formulated into pharmaceutical compositions for administration to subjects, preferably humans in a biologically compatible form suitable for administration in vivo.

The compositions containing the compounds of disclosure can be prepared by known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (2003-20th edition) and in The United States Pharmacopeia: The National Formulary (USP 24 NF19) published in 1999. On this basis, the compositions include, albeit not exclusively, solutions of the substances in association with one or more pharmaceutically acceptable vehicles or diluents, and contained in buffered solutions with a suitable pH and iso-osmotic with the physiological fluids.

The compounds of disclosure may be used pharmaceutically in the form of the free base, in the form of salts, solvates and as hydrates. All forms are within the scope of the disclosure. Acid and basic addition salts may be formed with the compounds of the disclosure for use as sources of the free base form even if the particular salt per se is desired only as an intermediate product as, for example, when the salt is formed only for the purposes of purification and identification. All salts that can be formed with the compounds of the disclosure are therefore within the scope of the present disclosure.

Methods of Medical Treatments and Uses

The compounds of the disclosure, including compounds of the Formula (A), (I) and (I.A) are inhibitors of the STAT5 protein. In one embodiment, the compounds of the disclosure are STAT5 selective inhibitors in relation to their activity against STAT5 and STAT3. In one embodiment, the compounds of the disclosure have $K_D$ values of less than 200 nM, optionally less than 150 nM, optionally less than 100 nM, or optionally less than 50 nM.

Accordingly, in one embodiment of the disclosure, there is included a method of treating or preventing a disease or condition mediated by signal transducer and activator of transcription 5 (STAT5) protein, comprising administering a pharmaceutically effective amount of a compound of the disclosure to a subject in need thereof. In one embodiment, the disease or condition mediated by STAT5 is a disease or condition in which inhibition of the STAT5 protein would be beneficial. In one embodiment, the disease or condition is a hematopoietic malignancy, skin condition, non-melanoma skin cancer, prostate cancer or inflammation, comprising administering a pharmaceutically effective amount of a compound of the disclosure to a subject in need thereof. In one embodiment, the hematopoietic malignancy is leukemia. In another embodiment, the leukemia is acute leukemia, chronic leukemia, lymphocytic leukemia or myelogenous leukemia. In another embodiment, the skin condition is psoriasis or dermatitis.

In another embodiment, the compounds of the disclosure are useful for inhibiting the signal transducer and activator of transcription 5 (STAT5) protein. In another embodiment, the compounds of the disclosure are useful for the preparation of a medicament for inhibiting the signal transducer and activator of transcription 5 (STAT5) protein. In one aspect of the disclosure, the compounds of the disclosure are useful for the treatment or prevention of hematopoietic malignancies, skin conditions, non-melanoma skin cancer, prostate cancer or inflammation. In one embodiment, the hematopoietic malignancy is leukemia. In another embodiment, the leukemia is acute leukemia, chronic leukemia, lymphocytic leukemia or myelogenous leukemia. In another embodiment, the skin condition is psoriasis or dermatitis.

In another embodiment, the compounds of the disclosure are useful as probes for investigating the function of STAT5 in various diseased cells. In one embodiment, the compounds of the disclosure specifically inhibit STAT5, and therefore, the compounds are used as probes in determining whether STAT5 is involved in a disease or condition.

Although the disclosure has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art to the present disclosure.

The operation of the disclosure is illustrated by the following representative examples. As is apparent to those skilled in the art, many of the details of the examples may be changed while still practicing the disclosure described herein.

EXAMPLES

Experimental Protocols

Example 1. Chemistry Methods

Anhydrous solvents methanol, DMSO, $CH_2Cl_2$, THF and DMF were purchased from Sigma Aldrich and used directly from Sure-Seal bottles. Molecular sieves were activated by heating to 300° C. under vacuum overnight. All reactions were performed under an atmosphere of dry nitrogen in oven-dried glassware and were monitored for completeness by thin-layer chromatography (TLC) using silica gel (visualized by UV light, or developed by treatment with $KMnO_4$ stain). NMR spectra were recorded in Bruker Avance III spectrometer at 23° C., operating at 400 MHz for $^1H$ NMR and 100 MHz $^{13}C$ NMR spectroscopy either in $CDCl_3$, $CD_3OD$ or $d_6$-DMSO. Chemical shifts (d) are reported in parts per million (ppm) after calibration to residual isotopic solvent. Coupling constants (J) are reported in Hz. Mass spectrometry was performed with an AB/Sciex QStar mass spectrometer with an ESI source, MS/MS and accurate mass capabilities, associated with an Agilent 1100 capillary LC system. Before biological testing, inhibitor purity was evaluated by reversed-phase HPLC (rpHPLC). Analysis by rpHPLC was performed using a Phenomenex Luna 5u C18 150 mm×4.6 mm column run at 1.2 mL/min, and using gradient mixtures. The linear gradient consisted of a changing solvent composition of either (I) 15% MeCN and 85% $H_2O$ with 0.1% TFA (v/v) to 100% MeCN over 30 minutes and (II) 15% MeCN and 85% $H_2O$ with 0.1% TFA (v/v) to 100% MeCN over 60 minutes, UV detection at 250 nm. For reporting HPLC data, percentage purity is given in parentheses after the retention time for each condition. All biologically evaluated compounds are >95% chemical purity as measured by HPLC. The HPLC traces for all tested compounds are provided in supporting information.

Compounds of the disclosure were synthesized in the following general manner as shown in Scheme 1.

Scheme 1:

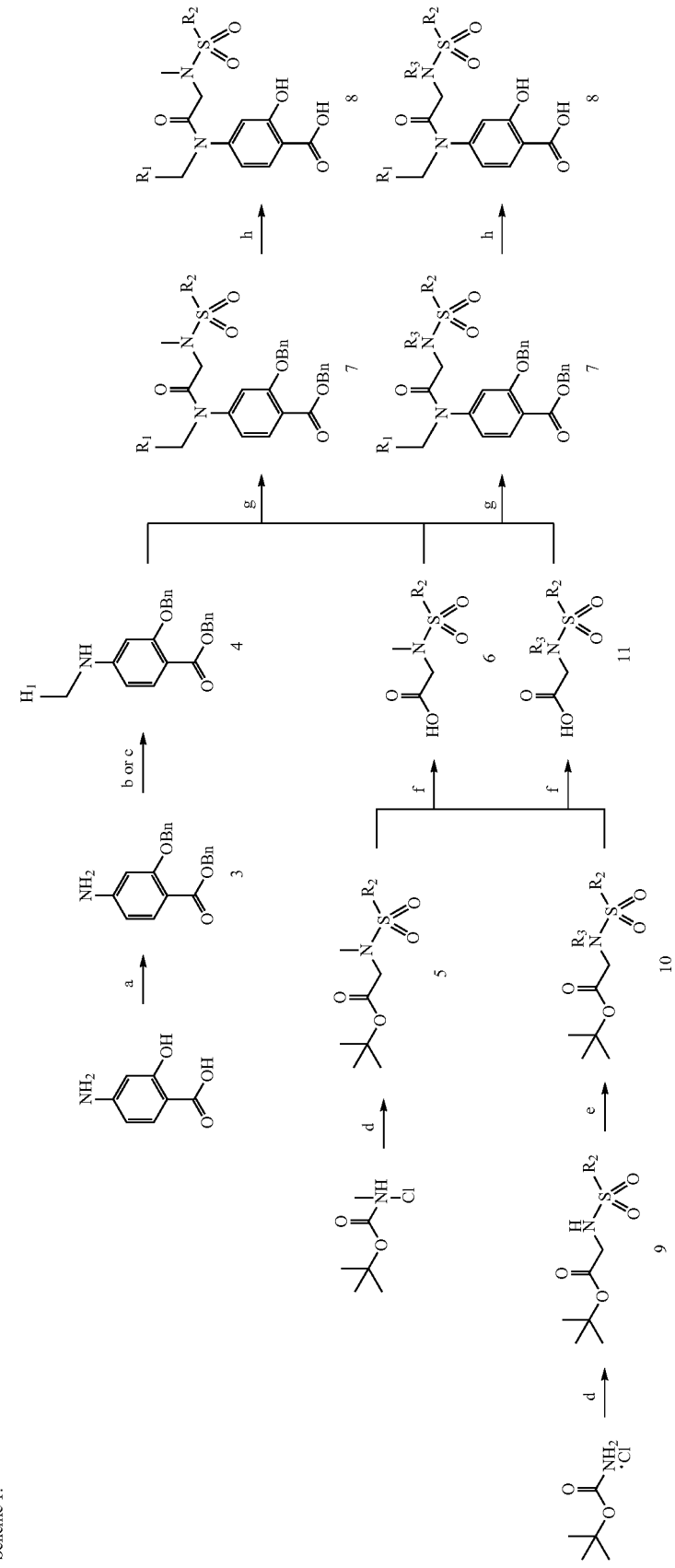

a) i) K'OBu, BnBr, DMF, 0° C.→RT., 1 H; then K'OBu, BnBr, DMF, 0° C. → RT., 16 h, 47%; b) 1) Aldehyde, AcOH, 3Å Mol. sieves, CH₃OH, 45° C., 2 h; 2) NaCNBH₃, 45° C., 16 h, 36-96%; c) Aldehyde, 3Å Mol. sieves, CH₂Cl₂, NaOAc, Na(OAc)₃BH, RT, 16 h, 88%; d) (CH₃)₃CSO₂Cl OR C₅F₅SO₂Cl, K₂CO₃, CH₃CN, 16 h, 0° C. → RT, 60-77%; e) 1) p-Cl(C₆H₆)BnBr, Cs₂CO₃, DMF, R.T., N₂, 2 h, 70%; f) CH₂Cl₂:TFA 1:1, RT, 1 h, 90%; g) PPh₃Cl₂, CHCl₃, 30 min, 100° C. microwave assisted heating, 20-98%; h) H₂, Pd/C, 1:1 THF/CH₃OH, 3-10 h, RT, 35-95%. DMF = N,N-dimethylformamide, TFA = Trifluoroacetic acid General Procedure a (Dibenzylation of Salicylic Acid).

To a stirred solution of 4-aminosalicylic acid (1.0 eq) in DMF (0.1 M) at 0° C. was added KO'Bu (1.2 eq). After 15 min, benzyl bromide (1.2 eq) was added drop-wise. The suspension was allowed to stir at room temperature for a further 4 h before the reaction vessel was again cooled to 0° C. Once again, KO'Bu (1.2 eq) was added prior to the dropwise addition of benzyl bromide (1.2 eq). The reaction was left to stir overnight before quenching with $H_2O$. The solution was then repeatedly extracted with ethyl acetate and the organic phases combined. The organics were then washed with $H_2O$ and brine then concentrated, dried over $Na_2SO_4$ and concentrated in vacuo. The resulting residue was purified using the Biotage Isolera automated column chromotographer with a 4:1 Hexanes/EtOAc gradient under reduced pressure.

General Procedure b (Reductive Amination Using Sodium Cyanoborohydride).

To a solution of benzyl protected 4-amino salicylic acid 5 (1.0 eq) and acetic acid (1.5 eq) stirred in anhydrous $CH_3OH$ (0.1 M) with 3 Å mol. sieves was added the aldehyde (1.0 eq). The solution was heated to 45° C. for 3 hr and then allowed to cool to rt. Next, $NaCNBH_3$ (1.3 equiv) was added portion-wise and the reaction was allowed to stir at rt overnight. The reaction was diluted with $CH_2Cl_2$, filtered and concentrated in vacuo. The concentrate was purified using the Biotage Isolera automated column chromatographer using a gradient of Hexanes/EtOAc.

General Procedure c (Reductive Amination Using Sodium Triacetoxyborohydride).

To a solution of benzyl protected 4-amino salicylic acid 5 (1.2 eq) and acetic acid (1.2 eq) stirred in anhydrous dichloroethane (0.1 M) with 3 Å mol. sieves was added the aldehyde (1.0 eq). The solution was then stirred at rt for 5 min after which $Na(OAc)_3BH$ (1.5 eq) was added and left to stir at rt overnight. The reaction was diluted with $CH_2Cl_2$, filtered and concentrated in vacuo. The concentrate was purified using the Biotage Isolera automated column chromatographer using a gradient of Hexanes/EtOAc.

General Procedure d (Sulfonylation of Glycine and Sarcosine t-Butyl Ester).

A solution of amino acid t-butyl ester (1 eq) and $K_2CO_3$ (1.1 eq) were dissolved in anhydrous acetonitrile and cooled to 0° C. before sulfonyl chloride (1 eq) was added. The resultant solution was allowed to stir overnight at rt. The reaction was concentrated in vacuo and residue was dissolved in $CH_2Cl_2$. The organics were combined and then washed sequentially with 0.1 M HCl, saturated $NaHCO_3$ and brine. The organics were then dried over $Na_2SO_4$ and concentrated in vacuo to furnish derivatives 7 & 8 with no further purification.

General Procedure e (Alkylation of Sulfonamide).

A solution of 8 (1 eq) and $Cs_2CO_3$ (1.3 eq) were dissolved in anhydrous DMF followed by the addition of p-ClBnBr (1 eq). The resultant solution was allowed to stir for 2 h at r.t. The reaction was quenched with $H_2O$ and then repeatedly extracted with ethyl acetate. The organic phases were combined and washed with $H_2O$, brine, dried over $Na_2SO_4$ and concentrated in vacuo. The resulting residue was purified using the Biotage Isolera automated column chromotographer with a 2:1 Hexanes/EtOAc gradient under reduced pressure.

General Procedure f (t-Butyl Ester Deprotection).

A solution of amino acid t-butyl ester (1 eq) was dissolved in TFA and immediately diluted with $CH_2CO_2$ in a 1:1 mixture (0.1 M) solution. The resultant solution was allowed to stir for 1 h and then co-evaporated with $CH_3OH$ (3×) and $CHCl_3$ (3×). The resultant residue was carried forward with no purification.

General Procedure g ($PPh_3Cl_2$ Peptide Coupling).

To a stirred solution of carboxylic acid 10 (1.1 eq) in $CHCl_3$ (0.1 M) was added $PPh_3Cl_2$ (2.5 eq). The reaction was allowed to stir 5 min at rt or until complete dissolvation, followed by the drop-wise addition of the secondary aniline 6 (1.0 eq). The reaction mixture was then heated in a microwave at 100° C. for 30 min. The reaction mixture was allowed to cool to rt followed by sequential washing with saturated $NaHCO_3$ and brine. The organic layers were then dried over $Na_2SO_4$ and concentrated in vacuo. The concentrate was absorbed directly onto silica for column chromatography purification using a gradient of hexanes and EtOAc.

General Procedure h (Hydrogenolysis of the Benzyl Ester and Benzyl Ether).

The benzyl protected salicylic acid, 11 (1 eq) was dissolved in a stirred solution of $CH_3OH/THF$ (1:2, 0.1 M). The solution was thoroughly degassed before the careful addition of 10% Pd/C (10 mg/mmol). $H_2$ gas was bubbled through the solvent for 5 min before the solution was put under an atmosphere of $H_2$ gas and stirred continuously for 2-5 h, monitoring completion of reaction via TLC. The $H_2$ gas was evacuated and the reaction filtered through celite to remove Pd catalyst and concentrated in vacuo. The resulting residue was adsorbed onto silica and columned using a Biotage Isolera in a gradient of $CH_2Cl_2$, $CH_3OH$ and 1% acetic acid.

Intermediate Characterization Data

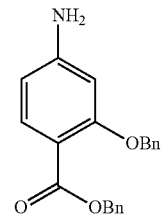

Benzyl 4-amino-2-(benzyloxy)benzoate (3)

Compound 3 was synthesized according to general procedure a, yielding the final product as an orange solid (47%): $\delta_H$ (400 MHz, d-$CDCl_3$) 5.07 (s, 2H, $CH_2$), 5.21 (s, 2H, $CH_2$), 5.99 (br s, 2H, $NH_2$), 6.18 (dd, J=8.6 and 1.8 Hz, 1H, CH)), 6.32 (d, J=1.7 Hz, 1H, CH), 7.28-7.38 (8H, m, CH), 7.47 (d, J=7.2 Hz, 2H, CH), 7.60 (d, J=8.6 Hz, 1H, CH); $\delta_C$ (400 MHz, $CDCl_3$) 65.8, 70.2, 99.1, 106.7, 109.0, 126.8, 127.5, 127.7, 127.9, 128.3, 128.4, 134.3, 136.6, 136.7, 152.2, 160.7, 165.7; LRMS (ES+) calculated for $[C_{21}H_{19}NO_3+H]$ 333.18. found 334.2.

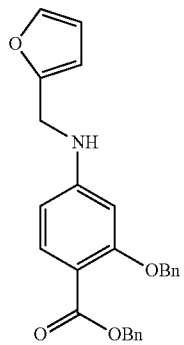 [SMILES: O=C(OCc1ccccc1)c1ccc(NCc2ccco2)cc1OCc1ccccc1]

Benzyl 2-(benzyloxy)-4-((furan-2-ylmethyl)amino) benzoate

Derivative 4 synthesized via furan-2-carbaldehyde on a 1.5 mmol scale using general procedure b (74%): $\delta_H$ (400 MHz, d-CDCl$_3$) 4.36 (d, J=5.4 Hz, 2H, CH$_2$), 4.54 (br s, 1H, NH), 5.12 (s, 2H, CH$_2$), 5.31 (s, 2H, CH$_2$), 6.19 (d, J=3.4 Hz, 1H, CH), 6.21 (d, J=2.0 Hz, 1H, CH), 6.24 (dd, J=8.6 and 2.0 Hz, 1H, CH), 6.31 (q, J=3.0, 1.8, and 4.6 Hz, 1H, CH) 7.26-7.50 (m, 11H, 11 CH), 7.84 (d, J=8.6 Hz, 1H, CH); $\delta_C$(100 MHz, d-CDCl$_3$) 40.6, 65.7, 70.4, 97.5, 104.9, 107.2, 108.9, 110.3, 126.8, 127.5, 127.6, 127.9, 128.2, 128.4, 134.2, 136.6, 136.7, 142.0, 151.4, 152.2, 160.7, 165.5 LRMS (ES+) Calculated for [C$_{26}$H$_{23}$NO$_4$+H] 413.16. found 414.2.

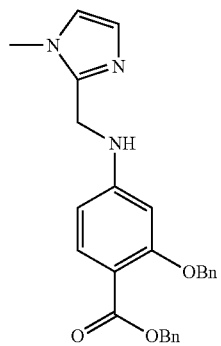

Benzyl-2-(benzyloxy)-(((1-methyl-H-imidazol-2-yl) methyl)amino)benzoate

Derivative 4 synthesized via 1-methyl-1H imidazole-2-carbaldehyde on a 1.5 mmol scale using general procedure b (43%): $\delta_H$ (400 MHz, d-CDCl$_3$) 3.53 (s, 3H, CH$_3$), 4.27 (d, J=5.4 Hz, 2H, CH$_2$), 5.08 (s, 2H, CH$_2$), 5.21 (br, 1H, NH), 5.31 (s, 2H, CH$_2$), 6.24 (dd, J=8.6, 2.0 Hz, 1H, CH), 6.30 (d, J=2.0 Hz, 1H, CH), 6.81 (s, 1H, CH), 6.96 (s, 1H, CH), 7.23-7.51 (m, 10H, 10 CH), 7.84 (d, J=8.6 Hz, 1H, CH); $\delta_C$ (100 MHz, d-CDCl$_3$) 14.1, 20.9, 29.6, 32.4, 40.1, 60.2, 65.7, 70.3, 97.6, 104.7, 108.6, 121.6, 126.9, 127.1, 127.5, 127.9, 128.2, 134.2, 136.7, 144.0, 152.5, 160.7, 165.7 LRMS (ES+) Calculated for [C$_{26}$H$_{25}$N$_3$O$_3$+H] 427.19. found 428.21.

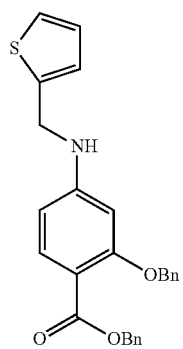 [SMILES: O=C(OCc1ccccc1)c1ccc(NCc2cccs2)cc1OCc1ccccc1]

Benzyl 2-(benzyloxy)-4-((thiophen-2-ylmethyl) amino)benzoate

Derivative 4 synthesized via thiophene-2-carbaldehyde on a 1.5 mmol scale using General Procedure b (73%): $\delta_H$ (400 MHz, d-CDCl$_3$) 4.50 (s, 2H, CH$_2$), 4.54 (br s, 1H, NH), 5.10 (s, 2H, CH$_2$), 5.31 (s, 2H, CH$_2$), 6.20 (d, J=2.0 Hz, 1H, CH), 6.25 (dd, J=8.6 and 2.0 Hz, 1H, CH), 6.97 (br, 2H, CH), 7.23 (dd, J=1.3, 4.8 Hz, 1H, CH), 7.27-7.58 (m, 10H, 10 CH), 7.84 (d, J=8.6 Hz, 1H, CH); $\delta_C$ (100 MHz, d-CDCl$_3$) 51.6, 65.4, 70.6, 96.5, 104.9, 109.5, 125.6, 126.2, 127.0, 127.1, 127.6, 128.8, 136.5, 140.3, 152.5, 161.3, 168.8 LRMS (ES+) Calculated for [C$_{26}$H$_{23}$NO$_3$S+H] 429.14. found 430.2.

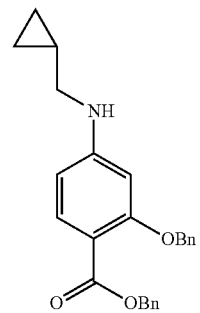 [SMILES: O=C(OCc1ccccc1)c1ccc(NCC2CC2)cc1OCc1ccccc1]

Benzyl 2-(benzyloxy)-4-((cyclopropylmethyl)amino)benzoate

Derivative 4 synthesized via cyclopropanecarbaldehyde on a 1.5 mmol scale using general procedure b (66%): $\delta_H$ (400 MHz, d-CDCl$_3$) 0.25 (dd, J=5.3 and 10.0 Hz, 2H, CH$_2$), 0.56 (dd, J=5.7, 13.0 Hz, 2H, CH$_2$), 1.05 (br, 1H, CH), 2.97 (s, 2H, CH$_2$), 4.40 (br, 1H, NH), 5.13 (s, 2H, CH$_2$), 5.33 (s, 2H, CH$_2$), 6.15 (d, J=2.0 Hz, 1H, CH), 6.19 (dd, J=8.6, 2.0 Hz, 1H, CH), 7.27-7.58 (m, 10H, 10 CH), 7.84 (d, J=8.6 Hz, 1H, CH); $\delta_C$(100 MHz, d-CDCl$_3$) 3.4, 10.4, 14.1, 48.2, 60.3, 65.7, 70.3, 96.9, 104.6, 107.9, 126.8, 127.4, 127.6, 127.9, 128.2, 128.3, 134.3, 136.7, 136.8, 153.1, 160.9, 165.7 LRMS (ES+) Calculated for [C$_{25}$H$_{25}$NO$_3$+H] 387.18. found 388.20.

21

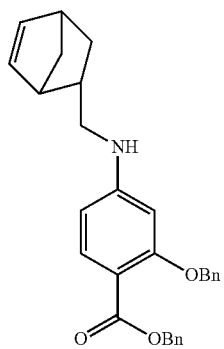 [SMILES: O=C(OCc1ccccc1)c1ccc(NCC2CC3C=CC2C3)cc1OCc1ccccc1]

Benzyl-2-(benzyloxy)-4-((bicyclo[2.2.1]hept-5-en-2-ylmethyl)amino)benzoate

Derivative 4 synthesized via bicycle [2.2.1]hept-5-ene-2-carbaldehyde on a 1.5 mmol scale via general procedure b (36%): $\delta_H$ (400 MHz, d-CDCl$_3$) 0.58-0.73 (m, 1H, CH$_2$), 1.25-1.46 (m, 2H, CH$_2$) 1.47-1.60 (m, 1H, CH$_2$), 1.85-2.03 (m, 1H, CH), 2.31 (br, 1H, CH), 2.79 (br, 1H, CH), 2.84-2.98 (m, 2H, CH$_2$) 4.38 (br, 1H, NH), 5.14 (s, 2H, CH$_2$), 5.35 (s, 2H, CH$_2$), 5.94-6.00 (m, 1H, CH), 6.20-6.27 (m, 1H, CH), 6.15 (d, J=2.0 Hz, 1H, CH), 6.19 (dd, J=8.6, 2.0 Hz, 1H, CH), 7.27-7.50 (m, 10H, 10 CH), 7.84 (d, J=8.6 Hz, 1H, CH); $\delta_C$ (100 MHz, d-CDCl$_3$) 30.2, 38.4, 42.3, 44.2, 47.4, 49.5, 65.7, 70.3, 96.9, 104.6, 107.6, 126.9, 127.5, 127.6, 127.9, 128.3, 128.4, 131.8, 134.2, 136.1, 136.7, 136.8, 137.8, 153.2, 160.9, 165.8 LRMS (ES+) Calculated for [C$_{29}$H$_{29}$NO$_3$+H] 439.21. found 440.21.

22

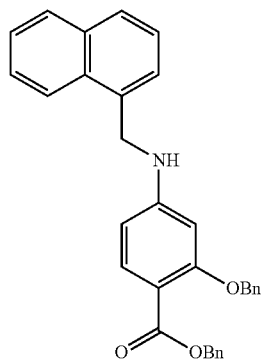

Benzyl 2-(benzyloxy)-4-(naphthalen-2-ylmethyl-amino)benzoate

Derivative 4 synthesized via 2-naphthaldehyde on a 0.9 mmol scale using general procedure c (88%): $\delta_H$ (400 MHz, d-CDCl$_3$) 4.35 (s, 2H, NH$_2$CH$_2$), 4.52 (br s, 1H, NH), 4.92 (s, 2H, CH$_2$), 5.19 (s, 2H, CH$_2$), 6.70 (d, J=2.0 Hz, 1H, CH), 6.12 (dd, J=8.6, 2.0 Hz, 1H, CH), 7.11-7.22 (m, 6H, CH), 7.25-7.30 (m, 4H, 4 CH), 7.34-7.39 (m, 2H, 2 CH), 7.61-7.75 (m, 5H, 5 CH); $\delta_C$ (100 MHz, d-CDCl$_3$) 47.1, 65.2, 69.7, 96.7, 104.4, 107.9, 124.7, 125.2, 125.3, 125.7, 126.2, 126.9, 127.0, 127.1, 127.3, 127.7, 127.8, 127.9, 132.1, 132.7, 133.7, 135.1, 136.1, 152.3, 160.3, 165.1; LRMS (ES+) Calculated for [C$_{32}$H$_{27}$NO$_3$+H]474.21. found 475.21.

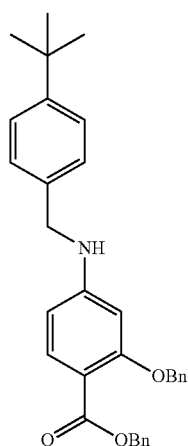 [SMILES: CC(C)(C)c1ccc(CNc2ccc(C(=O)OCc3ccccc3)c(OCc3ccccc3)c2)cc1]

Benzyl 2-(benzyloxy)-4-(4-tert-butylbenzyl)amino)benzoate

Derivative 4 synthesized via 4-tert-butylbenzaldehyde on a 0.9 mmol scale using general procedure b (96%): $\delta_H$ (400 MHz, d-CDCl$_3$) 1.19 (s, 9H, 3 CH$_3$), 4.13 (s, 2H, CH$_2$), 4.40 (br s, 1H, NH), 4.92 (s, 2H, CH$_2$), 5.17 (s, 2H, CH$_2$), 6.02 (d, J=2.0 Hz, 1H, CH), 6.06 (dd, J=8.6, 2.0 Hz, 1H, CH), 7.08-7.32 (m, 14H, 14 CH), 7.71 (d, J=8.6 Hz, 1H, CH); $\delta_C$ (100 MHz, d-CDCl$_3$) 31.0, 34.2, 47.0, 65.5, 70.1, 96.9, 104.6, 107.9, 125.3, 126.7, 126.9, 127.3, 127.4, 127.7, 128.1, 128.2, 134.1, 134.9, 136.5, 136.6, 150.2, 152.8, 160.6, 165.5; LRMS (ES+) Calculated for [C$_{32}$H$_{33}$NO$_3$+H] 480.25. found 481.26.

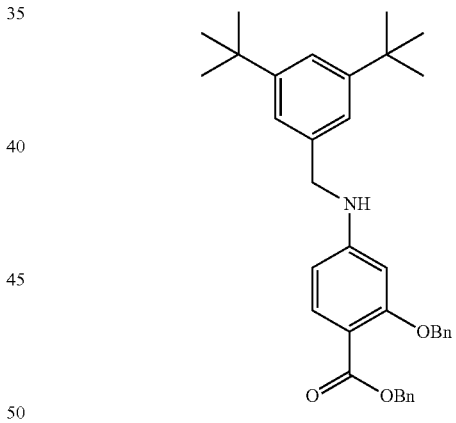

Benzyl 2-(benzyloxy)-4-(3, 5-di-tert-butylbenzyl)amino)benzoate

Derivative 4 synthesized via 3,5-di-tert-butylbenzaldehyde on a 0.9 mmol scale using general procedure b (60%): $\delta_H$ (400 MHz, d-CDCl$_3$) 1.34 (s, 18H, 6 CH$_3$), 4.30 (s, 2H, CH$_2$), 4.40 (br s, 1H, NH), 5.11 (s, 2H, CH$_2$), 5.32 (s, 2H, CH$_2$), 6.22 (d, J=2.0 Hz, 1H, CH), 6.26 (dd, J=8.6 and 2.0 Hz, 1H, CH), 7.15-7.53 (m, 13H, 13 CH), 7.87 (d, J=8.6 Hz, 1H, CH); $\delta_C$ (100 MHz, d-CDCl$_3$) 31.0, 34.2, 47.0, 65.5, 70.1, 96.9, 104.6, 107.9, 121.8, 122.4, 125.3, 126.7, 126.9, 127.3, 127.4, 127.7, 128.1, 128.2, 134.1, 134.9, 136.5, 136.6, 150.2, 152.8, 160.6, 165.5; LRMS (ES+) Calculated for [C$_{36}$H$_{41}$NO$_3$+H]535.31. found 536.30.

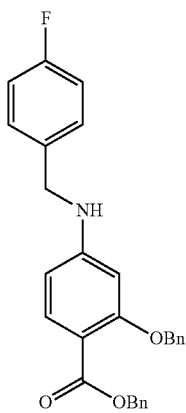 [SMILES: O=C(OCc1ccccc1)c1ccc(NCc2ccc(F)cc2)cc1OCc1ccccc1]

Benzyl 2-(benzyloxy)-4-((4-fluorobenzyl)amino)benzoate

Derivative 4 synthesized via 4-fluorobenzaldehyde on a 0.4 mmol scale using general procedure b (45%): $\delta_H$ (400 MHz, d-CDCl$_3$) 4.30 (s, 2H, CH$_2$), 4.50 (br s, 1H, NH), 5.07 (s, 2H, CH$_2$), 5.30 (s, 2H, CH$_2$), 6.14 (d, J=2.0 Hz, 1H, CH), 6.20 (dd, J=8.6 and 2.0 Hz, 1H, CH), 6.96-7.08 (m, 2H, CH), 7.22-7.40 (m, 10H, 10 CH), 7.40-7.45 (m, 2H, CH), 7.87 (d, J=8.6 Hz, 1H, CH); $\delta_C$ (100 MHz, d-CDCl$_3$) 46.9, 65.7, 70.3, 97.3, 104.8, 115.3, 115.6, 126.7, 127.5, 127.6, 127.8, 128.2, 128.3, 128.7, 128.8, 133.7, 134.2, 136.6, 152.4, 160.7, 160.8, 165.5; LRMS (ES+) Calculated for [C$_{28}$H$_{24}$FNO$_3$+H] 441.17. found 442.20.

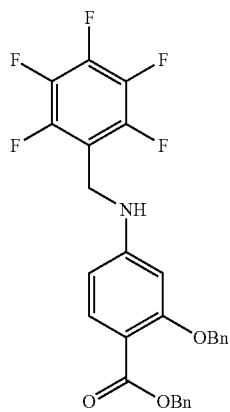 [SMILES: O=C(OCc1ccccc1)c1ccc(NCc2c(F)c(F)c(F)c(F)c2F)cc1OCc1ccccc1]

Benzyl 2-(benzyloxy)-4-(((perfluorophenyl)methyl)amino)benzoate

Derivative 4 synthesized via 2,3,4,5,6-pentafluorobenzaldehyde on a 0.4 mmol scale using general procedure b (36%): $\delta_H$ (400 MHz, d-CDCl$_3$) 4.45 (s, 2H, CH$_2$), 4.75 (br s, 1H, NH), 5.09 (s, 2H, CH$_2$), 5.27 (s, 2H, CH$_2$), 6.21 (d, J=2.0 Hz, 1H, CH), 6.22 (dd, J=8.6, 2.0 Hz, 1H, CH), 7.21-7.50 (m, 10H, 10CH), 7.80 (d, J=8.6 Hz, 1H, CH); $\delta_C$(100 MHz, d-CDCl$_3$) 13.9, 20.8, 35.0, 60.2, 65.8, 70.1, 97.0, 104.7, 109.4, 126.7, 127.5, 127.6, 128.2, 128.3, 134.3, 136.4, 136.5, 151.3, 160.7, 165.4, 171.0; LRMS (ES+) Calculated for [C$_{28}$H$_{20}$F$_5$NO$_3$+H] 513.14. found 514.20.

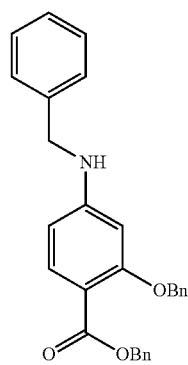 [SMILES: O=C(OCc1ccccc1)c1ccc(NCc2ccccc2)cc1OCc1ccccc1]

Benzyl 4-(benzylamino)-2-(benzyloxy)benzoate

Derivative 4 synthesized via benzaldehyde on a 1.2 mmol scale via General Procedure A (210 mg, 40%): $\delta_H$ (400 MHz, d-CDCl$_3$) 4.21 (s, 2H, CH$_2$), 4.95 (s, 2H, CH$_2$), 5.20 (s, 2H, CH$_2$), 6.03 (d, J=2.0 Hz, 1H, CH), 6.09 (dd, J=8.6, 2.1 Hz, 1H, CH), 7.15-7.34 (m, 15H, CH), 7.73 (d, J=8.6 Hz, 1H, CH); $\delta_C$(100 MHz, d-CDCl$_3$) 47.5, 66.7, 70.3, 97.2, 104.8, 108.3, 126.8, 127.2, 127.4, 127.5, 127.6, 127.9, 128.2, 128.3, 128.6, 134.2, 136.6, 136.7, 138.1, 152.8, 160.8, 165.6; LRMS (ES+) Calculated for [C$_{28}$H$_{25}$NO$_3$+H] 424.19. found 425.22.

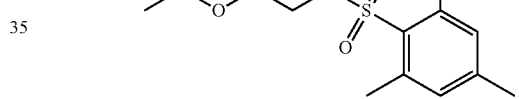

Tert-butyl 2-(N, 2, 4, 6-tetramethylphenylsulfonamido)acetate

Derivative 5 synthesized using general procedure d (77%): $\delta_H$(400 MHz, CDCl$_3$) 1.37 (s, 9H, CH$_3$) 2.30 (s, 3H, CH$_3$), 2.61 (s, 6H, CH$_3$) 2.82 (s, 3H, CH$_3$), 3.99 (s, 2H, CH$_2$), 6.95 (s, 2H, CH); $\delta_C$ (400 MHz, CDCl$_3$) 21.0, 22.9, 27.5, 35.1, 51.6, 130.6, 137.4, 141.3, 145.5, 170.2; LRMS (ES+) calculated for [C$_{16}$H$_{25}$NO$_4$S+H] 285.10. found 286.22.

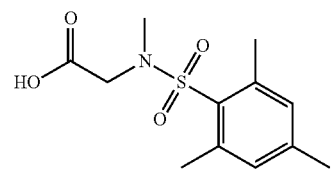 [SMILES: Cc1cc(C)c(S(=O)(=O)N(C)CC(=O)O)c(C)c1]

2-(N,2,4,6-tetramethylphenylsulfonamido)acetic Acid

Derivative 6 was synthesized via general procedure f (95%): $\delta_H$(400 MHz, CDCl$_3$) 2.32 (s, 3H, CH$_3$), 2.61 (s, 6H, CH$_3$), 2.82 (s, 3H, CH$_3$), 3.99 (s, 2H, CH$_2$), 6.95 (s, 2H, CH); $\delta_C$ (400 MHz, CDCl$_3$) 21.0, 22.9, 35.1, 51.6, 130.6, 137.4, 141.3, 145.5, 170.2; LRMS (ES+) calculated for [C$_{12}$H$_{17}$NO$_4$S+H] 271.09. found 272.28.

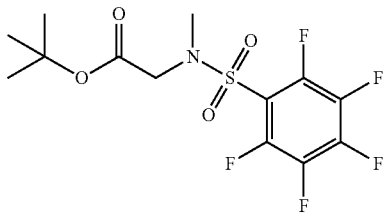 [SMILES: CN(CC(=O)OC(C)(C)C)S(=O)(=O)c1c(F)c(F)c(F)c(F)c1F]

Tert-butyl 2-(2,3,4,5,6-pentafluoro-N-methylphenyl-sulfonamido)acetate

Derivative 5 was synthesized using general procedure d (90%): δ$_H$ (400 MHz, CDCl$_3$) 1.37 (s, 9H, CH$_3$) 3.03 (s, 3H, CH$_3$), 4.10 (s, 2H, CH$_2$); δ$_C$ (400 MHz, CDCl$_3$) 27.5, 35.1, 51.6, 82.8, 115.6, 136.5, 144.8, 145.9, 167.0; LRMS (ES+) calculated for [C$_{13}$H$_{14}$F$_5$NO$_4$S+H] 376.06. found 377.09.

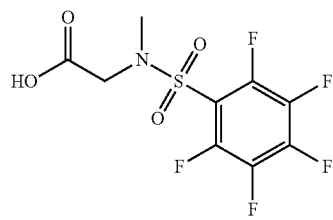 [SMILES: CN(CC(=O)O)S(=O)(=O)c1c(F)c(F)c(F)c(F)c1F]

2-(2,3,4,5,6-pentafluoro-N-methylphenylsulfona-mido)acetic acid

Derivative 6 was synthesized using general procedure f (97%): δ$_H$ (400 MHz, CDCl$_3$) 2.86 (s, 3H, CH$_3$), 4.10 (s, 2H, CH$_2$); δ$_C$ (400 MHz, CDCl$_3$) 35.5, 51.6, 115.6, 136.5, 144.8, 145.9, 167.0; LRMS (ES+) calculated for [C$_9$H$_6$F$_5$NO$_4$S+H] 320.00. found 321.05.

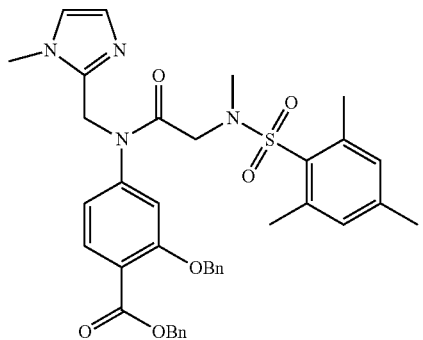

Benzyl-2-(benzyloxy)-4-(N-((1-methyl-1H-imida-zol-2-yl)methyl)-2-(N,2,4,6-tetramethylphenylsulfo-namido)acetamido)benzoate Secondary aniline 4 was coupled to mesityl derivative of 6 on a 0.16 mmol scale via general procedure g (60%): δ$_H$ (400 MHz, d-CDCl$_3$) 2.32 (s, 3H, CH$_3$), 2.62, (s, 6H, 2CH$_3$), 2.90 (s, 3H, CH$_3$), 3.39 (d, J=3.1 Hz, 3H, CH$_3$) 3.44-3.59 (m, 2H, CH$_2$), 3.92, (s, 2H, CH$_2$), 5.18 (s, 2H, CH$_2$), 5.33 (s, 2H, CH$_2$), 6.93 (dd, J=8.6 and 2.1 Hz, 1H, CH), 7.00 (s, 2H, CH), 7.27-7.55 (m, 11H, CH), 7.68 (d, J=2.0 Hz, 1H, CH), 7.89 (d, J=8.6 Hz, 1H, CH); δ$_C$ (100 MHz, d-CDCl$_3$) 21.6, 22.5, 33.4, 35.6, 48.1, 49.3, 65.6, 70.7, 104.5, 113.8, 116.2, 120.2, 126.8, 127.1, 127.6, 128.8, 130.4, 131.1, 136.3, 136.7, 137.2, 141.3, 145.2, 147.0, 152.3, 161.3, 166.5, 168.3; LRMS (ES+) Calcd for [C$_{38}$H$_{40}$N$_4$O$_6$S+H] 680.27. found 681.28.

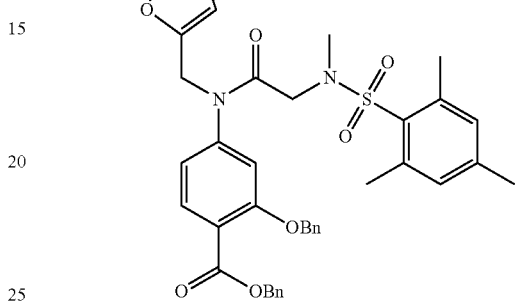

Benzyl-2-(benzyloxy)-4-(N-(furan-2-ylmethyl)-2-(N,2,4,6 tetramethylphenylsulfonamido)acetamido) benzoate Secondary aniline 4 was coupled to mesityl derivative 6 on a 1.0 mmol scale via general procedure g (30%): δ$_H$(400 MHz, d-CDCl$_3$) 2.27 (s, 3H, CH$_3$), 2.54, (s, 6H, 2CH$_3$), 2.77 (s, 3H, CH$_3$), 3.67 (s, 2H, CH$_2$), 4.77 (s, 2H, CH$_2$), 5.06 (s, 2H, CH$_2$), 5.36 (s, 2H, CH$_2$), 6.08 (d, J=2.0 Hz, 1H, CH), 6.25 (dd, J=8.6 and 2.1 Hz, 1H, CH), 6.60 (m, 2H, CH), 6.92 (s, 2H, CH), 7.27-7.49 (m, 11H, CH), 7.84 (d, J=8.6 Hz, 1H, CH); δ$_C$ (100 MHz, d-CDCl$_3$) 20.8, 22.7, 34.6, 66.9, 70.7, 109.4, 110.4, 113.6, 119.8, 126.9, 128.0, 128.1, 128.1, 128.4, 128.5, 131.7, 133.1, 135.6, 135.7, 140.4, 142.1, 142.4, 149.7, 158.8, 165.2, 166.7; LRMS (ES+) Calculated for [C$_{38}$H$_{38}$N$_2$O$_7$S+H] 666.24. found 667.24.

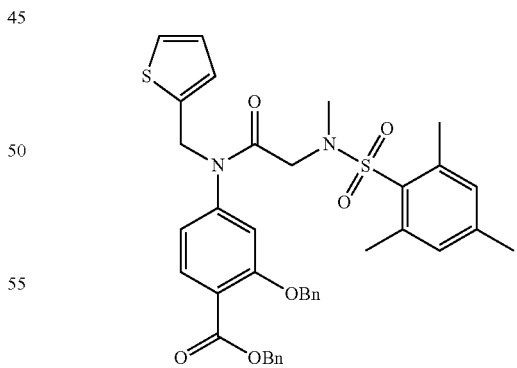

Benzyl 2-(benzyloxy)-4-(2-(N-2,4,6-tetramethylphe-nylsulfonamido)-N-(thiophen-2-ylmethyl)acetamido) benzoate Secondary aniline 4 was coupled to mesityl derivative 6 on a 0.9 mmol scale via general procedure g (24%): δ$_H$ (400 MHz, d-CDCl$_3$) 2.28 (s, 3H, CH$_3$), 2.56, (s, 6H, 2CH$_3$), 2.78

(s, 3H, CH$_3$), 3.67 (s, 2H, CH$_2$), 4.90 (s, 2H, CH$_2$), 5.03 (s, 2H, CH$_2$), 5.36 (s, 2H, CH$_2$), 6.50-6.63 (m, 2H, 2CH), 6.72 (d, J=3.1 Hz, 1H, CH), 6.86 (m, 1H, CH), 6.91 (s, 2H, CH), 7.21 (d, 1H, CH), 7.29-7.43 (m, 10H, CH), 7.84 (d, J=8.6 Hz, 1H, CH); δ$_C$ (100 MHz, d-CDCl$_3$) 20.8, 22.7, 29.6, 34.6, 47.5, 49.4, 66.9, 70.7, 113.7, 119.8, 121.0, 125.0, 126.4, 126.9, 127.7, 128.1, 128.4, 128.6, 131.8, 133.2, 135.6, 138.6, 140.5, 142.4, 144.5, 158.8, 165.2, 166.6; LRMS (ES+) Calculated for {C$_{38}$H$_{38}$N$_2$O$_6$S$_2$+H] 682.22. found 683.18.

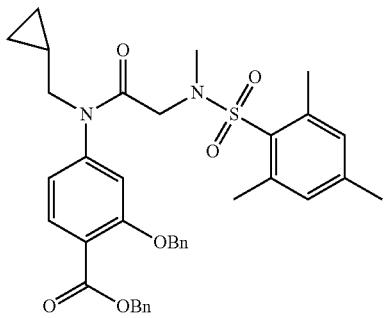 [SMILES: Cc1cc(C)c(S(=O)(=O)N(C)CC(=O)N(CC2CC2)c2ccc(C(=O)OCc3ccccc3)c(OCc3ccccc3)c2)c(C)c1]

Benzyl-2-(benzyloxy)-4-(N-(cyclopropylmethyl)-2-(N-2,4,6-tetramethylphenylsulfonamido)acetamido) benzoate Secondary aniline 4 was coupled to mesityl derivative 6 on a 0.8 mmol scale via general procedure g (34%): δ$_H$(400 MHz, d-CDCl$_3$): 0.035 (dd, J=5.1 and 10.0 Hz, 2H, CH$_2$), 0.33 (dd, J=5.3 and 12.9 Hz, 2H, CH$_2$), 1.05 (br, 1H, CH), (2.27 (s, 1H, CH$_3$), 2.56 (s, 6H, CH$_3$), 2.77 (s, 3H, CH$_3$), 3.47 (d, J=8.3 Hz, 2H, CH$_2$), 3.67 (s, 2H, CH$_2$), 5.18 (s, 2H, CH$_2$), 5.38 (s, 2H, CH$_2$), 6.77 (dd, J=1.6 and 8.0 Hz, 1H, CH), 6.81 (d, J=1.6 Hz, 1H, CH), 6.92 (s, 2H, CH), 7.25-7.46 (m, 10H), 7.89 (d, J=8.0 Hz, 1H, CH); δ$_C$ (100 MHz, d-CDCl$_3$) 3.6, 9.6, 14.1, 22.7, 34.6, 53.5, 60.2, 66.9, 70.7, 114.1, 120.1, 120.7, 126.9, 127.9, 128.1, 128.1, 128.4, 128.5, 131.7, 133.1, 135.7, 140.5, 142.2, 145.4, 158.8, 165.2, 166.4 LRMS (ES+) Calculated for [C$_{37}$H$_{40}$N$_2$O$_6$S] 640.26. found 641.24.

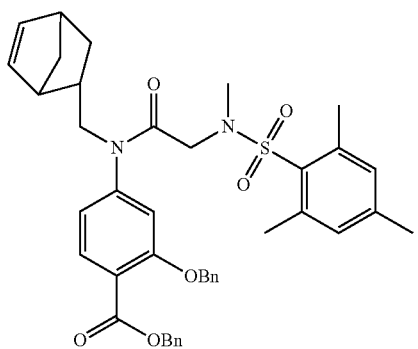 [SMILES: Cc1cc(C)c(S(=O)(=O)N(C)CC(=O)N(CC2CC3C=CC2C3)c2ccc(C(=O)OCc3ccccc3)c(OCc3ccccc3)c2)c(C)c1]

Benzyl-2-(benzyloxy)-4-(N-(bicyclo[2.2.1]hept-5-en-2-ylmethyl)-2-(N,2,4,6-tetramethylphenylsulfonamido)acetamido)benzoate Secondary aniline 4 was coupled to mesityl derivative 6 on a 0.4 mmol scale via general procedure g (25%): δ$_H$ (400 MHz, d-CDCl$_3$) 0.40 (d, J=2.7 Hz, 1H, CH), 0.78-0.94 (m, 1H, CH), 1.05-1.13 (m, 1H, CH$_2$), 1.22-1.44 (m, 4H, CH) 11.56-1.64 (m, 1H, CH), 2.05-2.13 (m, 1H, CH), 2.27 (s, 3H, CH$_3$), 2.57 (s, 6H, CH$_3$), 2.78 (s, 3H, CH$_3$), 3.68 (s, 2H, CH$_2$), 5.19 (d, J=11.2 Hz, 2H, CH), 5.38 (d, J=4.3 Hz, 2H, CH), 5.69 (dd, J=2.5 and 5.4 Hz, 1H, CH), 6.07 (dd, J=3.2, 5.7 Hz, 1H, CH), 6.68-6.78 (m, 2H, CH), 6.92 (s, 2H, CH), 7.25-7.45 (m, 10H, CH), 7.90 (d, J=8.1 Hz, CH);); δ$_C$ (100 MHz, d-CDCl$_3$) 30.3, 31.0, 38.4, 38.7, 41.6, 42.3, 44.1, 44.3, 45.1, 47.4, 48.7, 49.5, 65.7, 70.3, 96.9, 104.6, 104.6, 107.6, 126.9, 127.5, 127.6, 127.9, 128.3, 128.4, 131.8, 134.2, 134.3, 136.2, 136.8, 136.9, 137.8, 153.3, 160.9, 165.8. LRMS (ES+) Calculated for [C$_{41}$H$_{44}$N$_2$O$_6$S] 692.29. found 693.30.

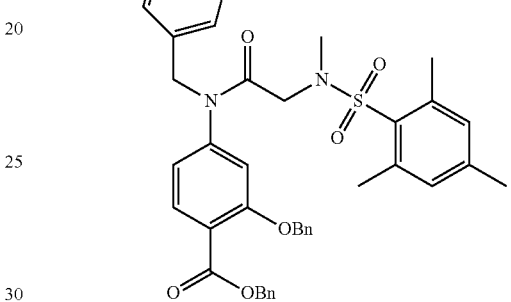

Benzyl-4-(N-benzyl-2-(N,2,4,6-tetramethylphenyl-sulfonamido)acetamido)-2-(benzyloxy)benzoate Secondary aniline 4 was coupled to mesityl derivative 6 on a 0.39 mmol scale via general procedure g (20%): δ$_H$ (400 MHz, d-CDCl$_3$): 2.28 (s, 3H, CH$_3$), 2.55 (s, 6H, 2 CH$_3$), 2.79 (s, 3H, CH$_3$), 3.68 (s, 2H, CH$_2$), 4.79 (s, 2H, CH$_2$), 4.95 (s, 2H CH$_2$), 5.34 (s, 2H, CH$_2$), 6.47 (s, 1H, CH), 6.51 (d, J=8.0 Hz, 1H, CH), 6.92 (s, 2H, CH), 7.04-7.09 (m, 2H, CH), 7.23-7.27 (m, 4H, CH), 7.29-7.36 (m, 8H, CH), 7.37-7.42 (m, 2H, CH), 7.79 (d, J=8.1 Hz, 1H, CH); δ$_C$ (100 MHz, d-CDCl$_3$) 20.8, 22.7, 34.7, 49.5, 52.9, 66.9, 70.6, 126.9, 127.6, 127.9, 128.1, 128.1, 128.4, 128.5, 128.7, 131.8, 133.1, 135.6, 136.5, 140.5, 142.4, 158.7, 165.2, 166.8. LRMS (ES+) Calculated for [C$_{40}$H$_{40}$N$_2$O$_6$S] 676.26. found 677.28.

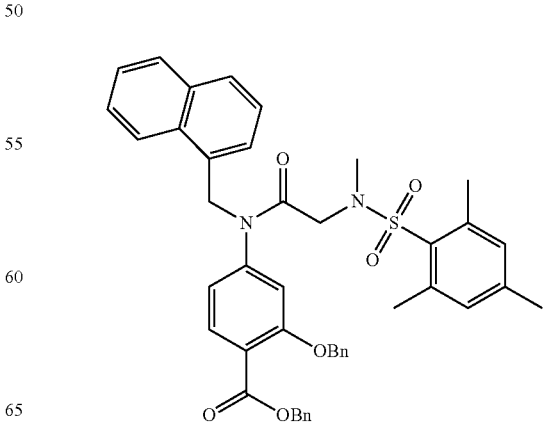

Benzyl-2-(benzyloxy)-4-(N-(napthalen-1-ylmethyl)-2-(N,2,4,6-tetramethylphenylsulfonamido)acetamido)benzoate Secondary aniline 4 was coupled to mesityl derivative 6 on a 0.39 mmol scale via general procedure g (20%): $\delta_H$(400 MHz, d-CDCl$_3$): 2.28 (s, 3H, CH$_3$), 2.55 (s, 6H, 2 CH$_3$), 2.79 (s, 3H, CH$_3$), 3.68 (s, 2H, CH$_2$), 4.79 (s, 2H, CH$_2$), 4.95 (s, 2H CH$_2$), 5.34 (s, 2H, CH$_2$), 6.47 (s, 1H, CH), 6.51 (d, J=8.0 Hz, 1H, CH), 6.92 (s, 2H, CH), 7.04-7.09 (m, 2H, CH), 7.23-7.27 (m, 4H, CH), 7.29-7.36 (m, 8H, CH), 7.37-7.42 (m, 2H, CH), 7.79 (d, J=8.1 Hz, 1H, CH); $\delta_C$ (100 MHz, d-CDCl$_3$) 20.8, 22.7, 34.7, 49.5, 52.9, 66.9, 70.6, 126.9, 127.6, 127.9, 128.1, 128.1, 128.4, 128.5, 128.7, 131.8, 133.1, 135.6, 136.5, 140.5, 142.4, 158.7, 165.2, 166.8. LRMS (ES+) Calculated for [C$_{40}$H$_{40}$N$_2$O$_6$S] 726.28. found 727.28.

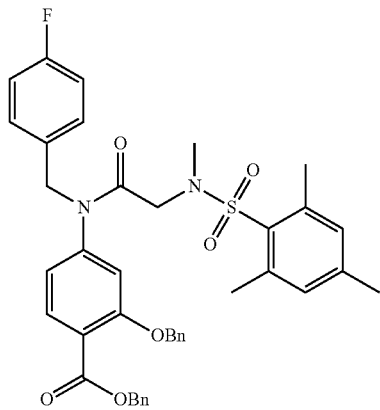 [SMILES: Cc1cc(C)c(S(=O)(=O)N(C)CC(=O)N(Cc2ccc(F)cc2)c2ccc(C(=O)OCc3ccccc3)c(OCc3ccccc3)c2)c(C)c1]

Benzyl-2-(benzyloxy)-4-(N-(4-fluorobenzyl)-2-(N,2,4,6-tetramethylphenylsulfonamido)acetamido)benzoate Secondary aniline 4 was coupled to mesityl derivative 6 on a 0.39 mmol scale via general procedure g (39%): 2.27 (s, 1H, CH$_3$), 2.54 (s, 6H, CH$_3$), 2.77 (s, 3H, CH$_3$), 3.68 (s, 2H, CH$_2$), 3.73 (s, 2H, CH$_2$), 5.01 (s, 2H, CH$_2$), 5.35 (s, 2H, CH$_2$), 6.37-6.64 (m, 2H, CH), 6.87-6.99 (m, 4H, CH), 6.98-7.10 (m, 2H, CH), 7.27-7.46 (m, 10H, CH), 7.82 (d, J=8.0 Hz, 1H, CH); $\delta_C$ (100 MHz, d-CDCl$_3$) 20.8, 22.6, 34.7, 49.5, 52.1, 66.9, 70.6, 113.7, 115.1, 115.3, 119.8, 126.8, 127.9, 128.1, 128.4, 128.5, 130.5, 131.7, 132.3, 133.1, 135.5, 140.4, 142.4, 144.6, 158.7, 165.1, 166.8; LRMS (ES+) Calculated for [C$_{40}$H$_{39}$FN$_2$O$_6$S] 694.25. found 695.25.

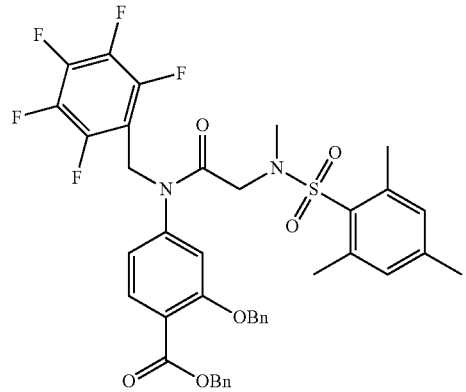 [SMILES: Cc1cc(C)c(S(=O)(=O)N(C)CC(=O)N(Cc2c(F)c(F)c(F)c(F)c2F)c2ccc(C(=O)OCc3ccccc3)c(OCc3ccccc3)c2)c(C)c1]

Benzyl-2-(benzyloxy)-4-(N-((perfluorophenyl)methyl)-2-(N,2,4,6-tetramethylphenylsulfonamido)acetamido)benzoate Secondary aniline 4 was coupled to mesityl derivative 6 on a 0.27 mmol scale via general procedure g (58%): 2.28 (s, 1H, CH$_3$), 2.53 (s, 6H, CH$_3$), 2.77 (s, 3H, CH$_3$), 3.66 (s, 2H, CH$_2$), 4.97 (s, 2H, CH$_2$), 5.12 (s, 2H, CH$_2$), 5.36 (s, 2H, CH$_2$), 6.57 (dd, J=8.6 and 2.1 Hz, 1H, CH), 6.67 (d, J=2.0 Hz, 1H, CH), 6.92 (s, 2H, CH), 7.27-7.46 (m, 10H, CH), 7.83 (d, J=8.6 Hz, 1H, CH); $\delta_C$ (100 MHz, d-CDCl$_3$) 14.0, 20.7, 22.6, 34.7, 39.9, 49.3, 67.0, 70.8, 113.3, 119.4, 121.4, 126.7, 128.0, 128.1, 128.4, 128.5, 131.7, 133.3, 135.4, 135.5, 140.4, 142.5, 143.5, 158.9, 164.9, 166.7; LRMS (ES+) Calculated for [C$_{40}$H$_{35}$F$_5$N$_2$O$_6$S] 766.21. found 767.25.

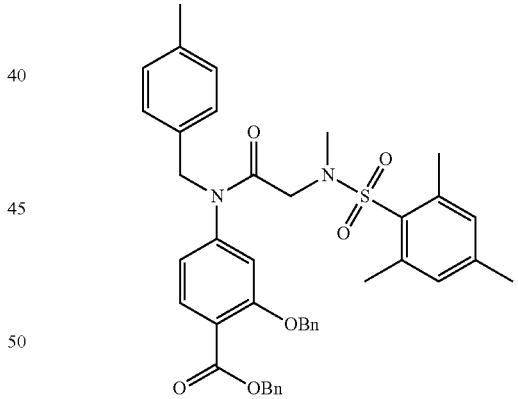

Benzyl-2-(benzyloxy)-4-(N-(4-methylbenzyl)-2-(N,2,4,6-tetramethylphenylsulfonamido)acetamido)benzoate Secondary aniline 4 was coupled to mesityl derivative 6 on a 0.39 mmol scale via general procedure g (28%): $\delta_H$(400 MHz, d-CDCl$_3$): 2.28 (s, 3H, CH$_3$), 2.31 (s, 3H, CH$_3$) 2.55 (s, 6H, 2 CH$_3$), 2.79 (s, 3H, CH$_3$), 3.66 (s, 2H, CH$_2$), 4.73 (s, 2H, CH$_2$), 4.96 (s, 2H CH$_2$), 5.34 (s, 2H, CH$_2$), 6.38-6.57 (m, 2H, 2CH), 6.89-6.98 (m, 4H, CH), 7.04 (s, 2H, CH), 7.29-7.43 (m, 10H, 10 CH), 7.78 (d, J=8.1 Hz, 1H, CH); $\delta_C$ (100 MHz, d-CDCl$_3$) 20.8, 20.9, 22.6, 34.6, 49.5, 52.5, 66.8, 70.6, 126.8, 127.9, 128.0, 128.1, 128.4, 128.5, 128.7, 129.0, 131.7, 133.0, 133.5, 135.6, 137.2, 140.4, 142.3, 158.6, 165.1, 166.6. LRMS (ES+) Calculated for [C$_{41}$H$_{42}$N$_2$O$_6$S] 690.28. found 691.28.

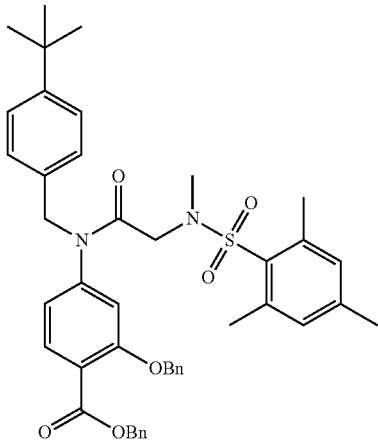 [SMILES: Cc1cc(C)c(S(=O)(=O)N(C)CC(=O)N(Cc2ccc(C(C)(C)C)cc2)c2ccc(C(=O)OCc3ccccc3)c(OCc3ccccc3)c2)c(C)c1]

Benzyl-2-(benzyloxy)-4-(N-(4-(tert-butyl)benzyl)-2-(N,2,4,6-tetramethylphenylsulfonamido)acetamido)benzoate Secondary aniline 4 was coupled to mesityl derivative 6 on a 0.39 mmol scale via general procedure g (37%): δ$_H$(400 MHz, d-CDCl$_3$): 1.28 (s, 9H, C(CH$_3$)), 2.28 (s, 3H, CH$_3$), 2.55 (s, 6H, 2 CH$_3$), 2.78 (s, 3H, CH$_3$), 3.67 (s, 2H, CH$_2$), 4.75 (s, 2H, CH$_2$), 4.91 (s, 2H CH$_2$), 5.34 (s, 2H, CH$_2$), 6.44 (d, J=2.0 Hz, 1H, CH), 6.55 (dd, J=2.0 and 8.6 Hz, 1H, CH), 6.92 (s, 2H, CH), 7.01 (d, J=8.4 Hz, 2H, CH) 7.27 (d, J=8.3 Hz, 2H, CH), 7.29-7.48 (m, 10H, 10 CH), 7.80 (d, J=8.3 Hz, 2H, CH); δ$_C$ (100 MHz, d-CDCl$_3$) 20.8, 22.6, 31.1, 34.3, 34.6, 49.5, 52.5, 66.8, 70.5, 125.2, 126.9, 127.9, 128.0, 128.1, 128.4, 128.5, 131.7, 133.0, 133.5, 135.6, 140.5, 142.3, 150.6, 158.6, 165.2, 166.6; LRMS (ES+) Calculated for [C$_{44}$H$_{48}$N$_2$O$_6$S] 732.32. found 733.36.

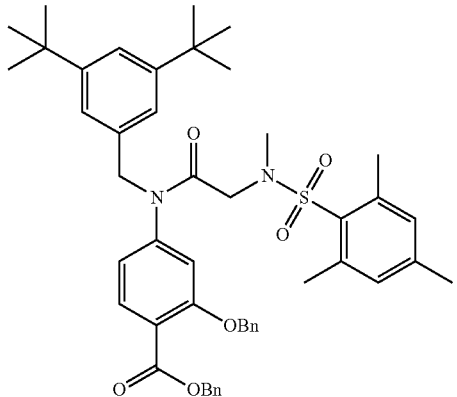 [SMILES: Cc1cc(C)c(S(=O)(=O)N(C)CC(=O)N(Cc2cc(C(C)(C)C)cc(C(C)(C)C)c2)c2ccc(C(=O)OCc3ccccc3)c(OCc3ccccc3)c2)c(C)c1]

Benzyl-2-(benzyloxy)-4-(N-(3,5-(-di-tert-butyl)benzyl)-2-(N,2,4,6-tetramethylphenylsulfonamido)acetamido)benzoate Secondary aniline 4 was coupled to mesityl derivative 6 on a 0.20 mmol scale via general procedure g (38%): δ$_H$(400 MHz, d-CDCl$_3$): 1.24 (s, 18H, 6CH$_3$), 2.04 (s, 3H, CH$_3$), 2.56 (s, 6H, 2 CH$_3$), 2.76 (s, 3H, CH$_3$), 3.70 (s, 2H, CH$_2$), 4.80 (s, 2H, CH$_2$), 4.85 (s, 2H CH$_2$), 5.34 (s, 2H, CH$_2$), 6.42 (d, J=2.0 Hz, 1H, CH), 6.56 (dd, J=2.0, 8.6 Hz, 1H, CH), 6.88-6.99 (m, 4H, CH) & 2CH), 7.27-7.44 (m, 11H, CH), 7.80 (d, J=8.31 Hz, 2H, CH); δ$_C$ (100 MHz, d-CDCl$_3$) 20.7, 22.6, 31.2, 34.4, 34.6, 49.5, 53.3, 66.8, 70.5, 121.2, 123.0, 126.8, 127.9, 128.0, 128.3, 128.4, 131.7, 132.9, 135.5, 135.6, 140.5, 142.3, 150.9, 158.6, 165.1, 166.4; LRMS (ES+) Calculated for [C$_{48}$H$_{16}$N$_2$O$_6$S] 788.39. found 789.41.

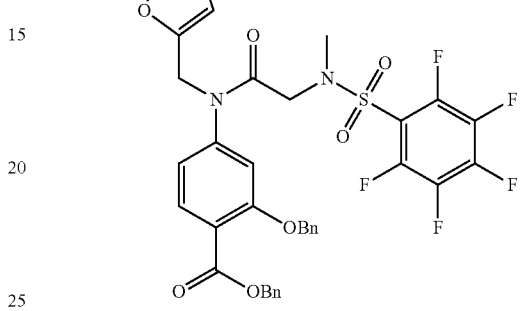

Benzyl-2-(benzyloxy)-4-(N-(furan-2-ylmethyl)-2-(2, 3,4,5,6-pentafluoro-N-methyl phenylsulfonamido) acetamido)benzoate Secondary aniline 4 was coupled to pentafluoro derivative 6 on a 0.4 mmol scale via general procedure g (31%): δ$_H$ (400 MHz, d-CDCl$_3$) 3.05 (s, 3H, CH$_3$), 3.84 (s, 2H, CH$_2$), 4.68 (s, 2H, CH$_2$), 5.08 (s, 2H, CH$_2$), 5.36 (s, 2H, CH$_2$), 6.02 (d, J=3.2 Hz, 1H, CH), 6.25 (m, 1H, CH), 6.58 (d, J=2.0 Hz, 1H, CH), 6.67 (dd, J=8.6, 2.1 Hz, 1H, CH), 7.26-7.53 (m, 11H, CH), 7.85 (d, J=8.6 Hz, 1H, CH); δ$_C$ (100 MHz, d-CDCl$_3$) 35.9, 51.6, 66.9, 70.6, 109.5, 110.3, 113.5, 119.6, 126.9, 128.0, 128.1, 128.4, 128.5, 133.2, 135.5, 142.4, 149.0, 158.7, 165.1; LRMS (ES+) Calculated for [C$_{35}$H$_{27}$F$_5$N$_2$O$_7$S+H] 714.15. found 715.16.

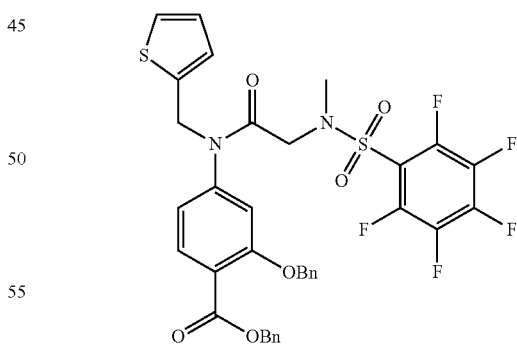

Benzyl-2-(benzyloxy)-4-(2-(N-2,3,4,5,6-pentafluoro-N-methylphenylsulfonamido)-N-(thiophen-2-ylmethyl)acetamido)benzoate Secondary aniline 4 was coupled to pentafluoro derivative 6 on a 0.3 mmol scale via general procedure g (68%): δ$_H$ (400 MHz, d-CDCl$_3$); 3.06 (s, 3H, CH$_3$), 3.87 (s, 2H, CH$_2$), 4.86 (s, 2H, CH$_2$), 5.07 (s, 2H, CH$_2$), 5.37 (s, 2H, CH$_2$), 6.60

(d, J=2.0 Hz, 1H, CH), 6.68 (d, J=2.1 Hz, 1H, CH), 6.70 (dd, J=8.6, 2.1 Hz, 1H, CH), 6.88 (m, 1H, CH), 7.25 (d, J=2.6 Hz, 1H, CH), 7.29-7.46 (m, 10H, CH), 7.88 (d, J=8.6 Hz, 1H, CH); $\delta_C$ (100 MHz, d-CDCl$_3$) 14.0, 20.8, 24.5, 35.8, 36.4, 47.4, 51.6, 60.2, 66.9, 70.6, 113.6, 119.7, 121.3, 126.1, 126.4, 126.9, 127.7, 128.0, 128.1, 128.4, 128.5, 133.2, 135.5, 137.9, 143.7, 158.7, 165.1, 165.7; LRMS (ES+) Calculated for {C$_{35}$H$_{27}$F$_5$N$_2$O$_6$S+H]730.12. found 731.12.

CH$_3$), 3.68 (s, 2H, CH$_2$), 5.19 (s, 2H, CH), 5.38 (s, 2H, CH), 5.69 (dd, J=2.5 and 5.4 Hz, 1H, CH), 6.07 (J=3.2, 5.7 Hz, 1H, CH), 6.68-6.78 (m, 2H, CH), 6.92 (s, 2H, CH), 7.25-7.45 (m, 10H, CH), 7.90 (d, J=8.1 Hz, CH);); $\delta_C$ (100 MHz, d-CDCl$_3$) 29.8, 35.9, 37.0, 41.7, 42.0, 44.2, 45.0, 49.3, 51.9, 53.4, 66.9, 70.7, 113.6, 119.4, 126.8, 126.9, 128.0, 128.1, 128.4, 128.6, 131.8, 133.2, 135.6, 137.4, 144.8, 158.7, 165.1, 165.6; LRMS (ES+) Calculated for [C$_{38}$H$_{33}$F$_5$N$_2$O$_6$S] 740.20. found 741.21.

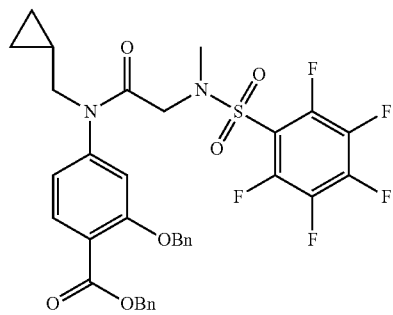 [SMILES: CN(CC(=O)N(CC1CC1)c1ccc(C(=O)OCc2ccccc2)c(OCc2ccccc2)c1)S(=O)(=O)c1c(F)c(F)c(F)c(F)c1F]

Benzyl-2-(benzyloxy)-4-(N-(cyclopropylmethyl)-2-(2,3,4,5,6-pentafluoro-N-methylphenylsulfonamido)acetamido)benzoate Secondary aniline 4 was coupled to pentafluoro derivative 6 on a 0.5 mmol scale via general procedure g (93%): $\delta_H$ (400 MHz, d-CDCl$_3$); 0.01 (dd, J=5.1 and 10.0 Hz, 2H, CH$_2$), 0.36 (dd, J=5.3 and 12.9 Hz, 2H, CH$_2$), 0.73 (br, 1H, CH), 3.04 (s, 3H, CH$_3$), 3.38 (d, J=7.19 Hz, 2H, CH$_2$), 3.86 (s, 2H, CH$_2$), 5.22 (s, 2H, CH$_2$), 5.38 (s, 2H, CH$_2$), 6.84 (d, J=1.6 Hz, 1H, CH), 6.85 (dd, J=1.6 and 8.0 Hz, 1H, CH), 7.28-7.47 (m, 10H, CH), 7.91 (d, J=8.0 Hz, 1H, CH); $\delta_C$ (100 MHz, d-CDCl$_3$) 3.4, 9.3, 14.0, 35.9, 51.7, 53.6, 66.9, 70.7, 113.9, 119.9, 126.9, 127.9, 128.1, 128.4, 128.5, 133.2, 135.5, 135.6, 144.7, 158.7, 165.1, 165.6; LRMS (ES+) Calculated for [C$_{34}$H$_{29}$F$_5$N$_2$O$_6$S] 688.17. found 689.19.

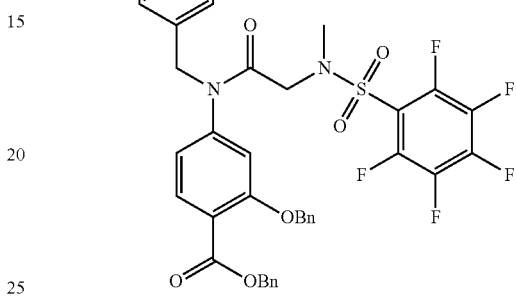

Benzyl-4-(N-benzyl-2-(2,3,4,5,6-pentafluoro-N-methylphenylsulfonamido)acetamido)-2-(benzyloxy)benzoate Secondary aniline 4 was coupled to pentafluoro derivative 6 on a 0.5 mmol scale via general procedure g (64%): $\delta_H$ (400 MHz, d-CDCl$_3$): 3.05 (s, 3H, CH$_3$), 3.87 (s, 2H, CH$_2$), 4.71 (s, 2H, CH$_2$), 4.99 (s, 2H CH$_2$), 5.35 (s, 2H, CH$_2$), 6.49 (s, 1H, CH), 6.63 (d, J=8.0 Hz, 1H, CH), 7.03 (m, 2H, CH), 7.19-7.44 (m, 12H, CH) 7.83 (d, J=8.1 Hz, 1H, CH); $\delta_C$ (100 MHz, d-CDCl$_3$) 35.8, 51.8, 52.9, 66.9, 70.6, 113.8, 119.8, 121.2, 126.9, 127.8, 128.0, 128.1, 128.3, 128.4, 128.5, 128.6, 133.2, 135.5, 135.9, 144.0, 158.6, 165.1, 165.8; LRMS (ES+) Calculated for [C$_{37}$H$_{29}$F$_5$N$_2$O$_6$S] 724.17. found 725.17.

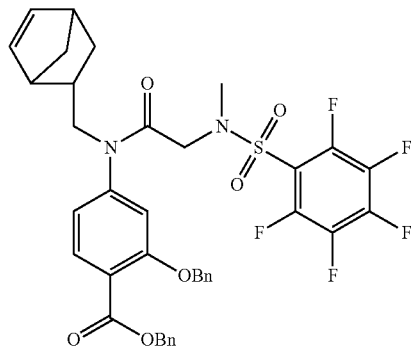 [SMILES: CN(CC(=O)N(CC1CC2C=CC1C2)c1ccc(C(=O)OCc2ccccc2)c(OCc2ccccc2)c1)S(=O)(=O)c1c(F)c(F)c(F)c(F)c1F]

Benzyl-2-(benzyloxy)-4-(N-(bicyclo[2.2.1]hept-5-en-2-ylmethyl)-2-(2,3,4,5,6-pentafluoro-N-methyl-phenylsulfonamido)acetamido)benzoate Secondary aniline 4 was coupled to pentafluoro derivative 6 on a 0.3 mmol scale via general procedure g (84%): $\delta_H$ (400 MHz, d-CDCl$_3$) 0.40 (d, J=2.7 Hz, 1H, CH$_2$), 0.78-0.94 (m, 1H, CH), 1.05-1.13 (m, 1H, CH$_2$) 1.22-1.44 (m, 4H, CH) 11.56-1.64 (m, 1H, CH), 2.05-2.13 (m, 1H, CH), 2.78 (s, 3H,

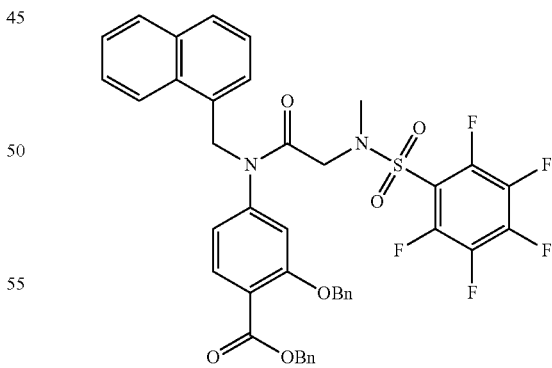

Benzyl-2-(benzyloxy)-4-(N-(napthalen-1-ylmethyl)-2-(2,3,4,5,6-pentafluoro-N-methylphenylsulfona-mido)acetamido)benzoate Secondary aniline 4 was coupled to pentafluoro derivative 6 on a 0.5 mmol scale via general procedure g (83%): $\delta_H$ (400 MHz, d-CDCl$_3$): 3.06 (s, 3H, CH$_3$), 3.90 (s, 2H, CH$_2$), 4.87 (s, 2H, CH$_2$), 4.88 (s, 2H CH$_2$), 5.33 (s, 2H, CH$_2$), 6.48 (s, 1H, CH), 6.63 (d, J=8.0 Hz, 1H, CH), 7.14-7.53 (m, 14H, CH) 7.67-7.88 (m, 3H, CH) δ$_C$ (100 MHz, d-CDCl$_3$) 35.8, 51.9, 53.0, 66.9, 70.6, 113.8, 119.8, 126.1, 126.2, 126.8, 127.5, 127.6, 127.8, 127.9, 128.1, 128.4, 132.7, 132.9, 133.2, 133.3, 135.4, 135.5, 158.7, 165.0, 166.0; LRMS (ES+) Calculated for [C$_{41}$H$_{31}$F$_5$N$_2$O$_6$S] 774.18. found 775.19.

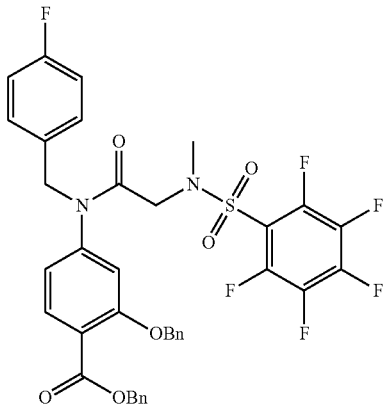

Benzyl-2-(benzyloxy)-4-(N-(4-fluorobenzyl)-2-(2,3,4,5,6-pentafluoro-N-phenylsulfonamido)acetamido)benzoate Secondary aniline 4 was coupled to pentafluoro derivative 6 on a 0.2 mmol scale via general procedure g (73%): 3.05 (s, 3H, CH$_3$), 3.88 (s, 2H, CH$_2$), 4.67 (s, 2H, CH$_2$), 5.05 (s, 2H, CH$_2$), 5.36 (s, 2H, CH$_2$), 6.53 (s, 2H, CH), 6.61 (dd, J=2.05, 8.63 Hz, 2H, CH), 6.87-7.04 (m, 4H, CH), 7.28-7.48 (m, 10H, CH), 7.84 (d, J=8.0 Hz, 1H, CH); δ$_C$ (100 MHz, d-CDCl$_3$) 35.8, 50.8, 51.8, 52.2, 67.0, 70.6, 113.7, 115.2, 115.4, 119.8, 121.3, 126.8, 128.0, 128.1, 128.4, 128.5, 130.3, 130.4, 131.7, 133.2, 135.4, 135.5, 143.8, 158.7, 161.0, 163.4, 165.0, 165.9; LRMS (ES+) Calculated for [C$_{37}$H$_{29}$F$_6$N$_2$O$_6$S] 742.16. found 743.16.

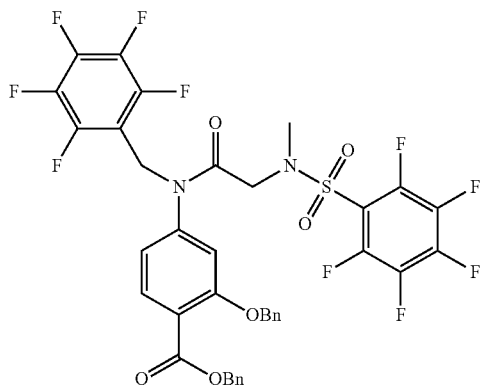 [SMILES: CN(CC(=O)N(Cc1c(F)c(F)c(F)c(F)c1F)c1ccc(C(=O)OCc2ccccc2)c(OCc2ccccc2)c1)S(=O)(=O)c1c(F)c(F)c(F)c(F)c1F]

Benzyl-2-(benzyloxy)-4-(2-(2,3,4,5,6-pentafluoro-N-methylphenylsulfonamido)-N-((perfluorophenyl)methyl)acetamido)benzoate Secondary aniline 4 was coupled to pentafluoro derivative 6 on a 0.1 mmol scale via general procedure g (74%): 3.04 (s, 3H, CH$_3$), 3.85 (s, 2H, CH$_2$), 4.88 (s, 2H, CH$_2$), 5.15 (s, 2H, CH$_2$), 5.36 (s, 2H, CH$_2$), 6.65 (d, J=2.0 Hz, 1H, CH), 6.69 (dd, J=8.6, 2.1 Hz, 1H, CH), 7.28-7.50 (m, 10H, CH), 7.87 (d, J=8.6 Hz, 1H, CH); δ$_C$ (100 MHz, d-CDCl$_3$) 35.3, 35.6, 48.3, 65.6, 70.9, 104.6, 112.2, 113.9, 115.4, 116.7, 127.1, 128.9, 131.3, 136.1, 136.2, 137.8, 141.4, 144.7, 147.3, 161.2, 166.8, 168.4; LRMS (ES+) Calculated for [C$_{37}$H$_{24}$F$_{10}$N$_2$O$_6$S] 814.12. found 815.14.

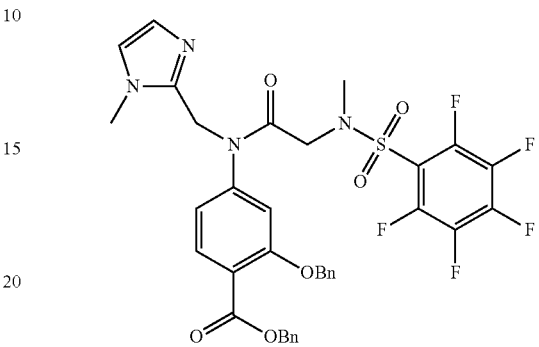

Benzyl-2-(benzyloxy)-4-(N-((1-methyl-1H-imidazol-2-yl)methyl)-2-(2,3,4,5,6-pentafluoro-N-methylphenylsulfonamido)acetamido)benzoate Secondary aniline 4 was coupled to pentafluoro derivative 6 on a 0.2 mmol scale via general procedure g (72%): δ$_H$ (400 MHz, d-CDCl$_3$) 2.28 (s, 3H, CH$_3$), 3.80 (d, J=3.1 Hz, 3H, CH$_3$), 3.20 (s, 2H, CH$_2$), 4.22 (s, 2H, CH$_2$), 4.51 (s, 2H, CH$_2$), 4.76 (s, 2H, CH$_2$), 6.26 (dd, J=8.6, 2.1 Hz, 1H, CH), 6.29 (s, 2H, CH), 6.78-6.99 (m, 10H, CH), 6.35 (s, 1H, CH), 6.41 (s, 1H, CH), 7.68 (d, J=2.0 Hz, 1H, CH), 7.44 (d, J=8.6 Hz, 1H, CH); δ$_C$ (100 MHz, d-CDCl$_3$) 33.4, 35.6, 48.1, 49.3, 65.6, 70.7, 104.5, 112.3, 113.8, 116.2, 120.2, 126.8, 127.1, 127.6, 128.8, 130.4, 131.1, 136.3, 136.7, 137.2, 144.9, 147.0, 152.3, 161.3, 166.5, 168.3; LRMS (ES+) Calcd for [C$_{35}$H$_{29}$F$_5$N$_4$O$_6$S+H] 728.17. found 729.18.

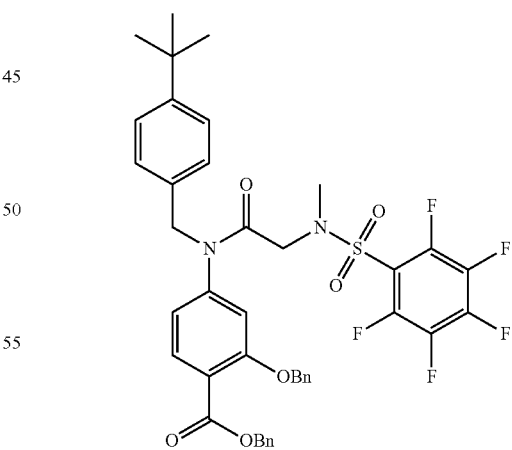

Benzyl-2-(benzyloxy)-4-(N-(4-(tert-butyl)benzyl)-2-(2,3,4,5,6-pentafluro-N-methylphenylsulfonamido)acetamido)benzoate Secondary aniline 4 was coupled to pentafluoro derivative 6 on a 0.4 mmol scale via general procedure g (98%): δ$_H$ (400 MHz, d-CDCl$_3$): 1.29 (s, 9H, C(CH$_3$)), 3.04 (s, 3H, CH$_3$), 3.85 (s, 2H, CH$_2$), 4.67 (s, 2H, CH$_2$), 4.94 (s, 2H CH$_2$), 5.34 (s, 2H, CH$_2$), 6.46 (d, J=2.0 Hz, 1H, CH), 6.65 (dd, J=2.0, 8.6 Hz, 1H, CH), 6.96 (d, J=8.7 Hz, 2H, CH), 7.27-7.42 (m, 12H, CH), 7.83 (d, J=8.3 Hz, 2H, CH); δ$_C$ (100 MHz, d-CDCl$_3$) 31.1, 34.3, 35.8, 51.8, 52.6, 66.9, 70.6, 113.8, 119.8, 125.3, 126.9, 128.0, 128.1, 128.4, 128.5, 132.9, 133.2, 135.4, 135.5, 150.8, 158.6, 165.1; LRMS (ES+) Calculated for [C$_{41}$H$_{37}$F$_5$N$_2$O$_6$S] 780.23. found 781.23.

Synthesis of the Tetrapodal Inhibitors (13a-d)

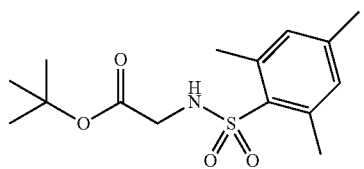 [SMILES: Cc1cc(C)c(S(=O)(=O)NCC(=O)OC(C)(C)C)c(C)c1]

tert-butyl (mesitylsulfonyl)glycinate

Derivative 9 synthesized using general procedure d (71%): δ$_H$ (400 MHz, CDCl$_3$) 1.36 (s, 9H, (CH$_3$)$_3$), 2.29 (s, 3H, CH$_3$), 2.65 (s, 6H, CH$_3$), 3.60 (d, J=5.4 Hz, 2H, CH$_2$), 5.08 (t, J=5.13 Hz, 2H, CH); δ$_C$ (400 MHz, CDCl$_3$) 20.8, 23.0, 27.7, 46.5, 81.9, 130.0, 137.4, 140.1, 145.0, 167.5; LRMS (ES+) calculated for [C$_{15}$H$_{23}$NO$_4$S+H] 313.13. found 314.11.

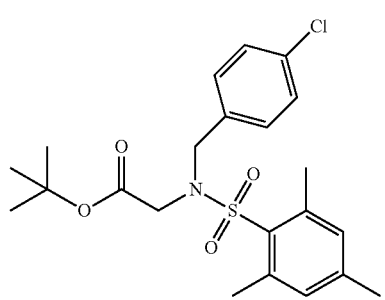 [SMILES: Cc1cc(C)c(S(=O)(=O)N(CC(=O)OC(C)(C)C)Cc2ccc(Cl)cc2)c(C)c1]

tert-butyl N-(4-chlorobenzyl)-N-(mesitylsulfonyl)glycinate

Derivative 10 synthesized using general procedure e (77%): δ$_H$ (400 MHz, CDCl$_3$) 1.34 (s, 9H, (CH$_3$)$_3$), 2.29 (s, 3H, CH$_3$), 2.63 (s, 6H, CH$_3$), 3.70 (s, 2H, CH$_2$), 4.49 (s, 2H, CH$_2$) 6.95 (s, 2H, CH), 7.08 (d, J=8.1 Hz, 2H, CH), 7.25 (d, J=8.1 Hz, 2H, CH); δ$_C$ (400 MHz, CDCl$_3$) 20.8, 23.0, 27.7, 46.5, 51.8, 81.9, 128.6, 130.0, 132.3, 134.6, 137.4, 140.1, 145.0, 167.5; LRMS (ES+) calculated for [C$_{22}$H$_{28}$ClNO$_4$S+H] 437.14. found 438.10.

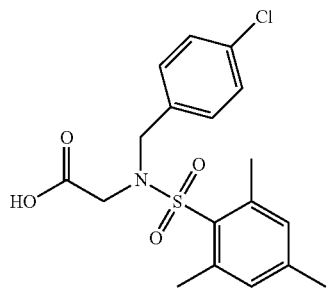 [SMILES: Cc1cc(C)c(S(=O)(=O)N(CC(=O)O)Cc2ccc(Cl)cc2)c(C)c1]

N-(4-chlorobenzyl)-N-(mesitylsulfonyl)glycine

Derivative 11 synthesized using general procedure f (90%): δ$_H$ (400 MHz, CDCl$_3$) 2.29 (s, 3H, CH$_3$), 2.63 (s, 6H, CH$_3$), 3.70 (s, 2H, CH$_2$), 4.49 (s, 2H, CH$_2$) 6.95 (s, 2H, CH), 7.08 (d, J=8.0 Hz, 2H, CH), 7.25 (d, J=8.0 Hz, 2H, CH); δ$_C$ (400 MHz, CDCl$_3$) 20.8, 23.0, 46.5, 51.8, 128.6, 130.0, 132.3, 134.6, 137.4, 140.1, 145.0, 167.5; LRMS (ES+) calculated for [C$_{18}$H$_{20}$ClNO$_4$S+H] 381.08. found 382.07.

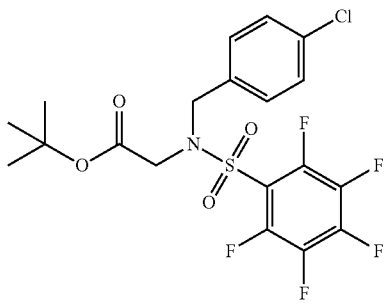 [SMILES: CC(C)(C)OC(=O)CN(Cc1ccc(Cl)cc1)S(=O)(=O)c1c(F)c(F)c(F)c(F)c1F]

tert-butyl ((perfluorophenyl)sulfonyl)glycinate

Derivative 9 synthesized using general procedure d (71%): δ$_H$ (400 MHz, CDCl$_3$) 1.40 (s, 9H, COO(CH$_3$)$_3$), 3.93 (s, 2H, CH$_2$), 5.54 (s, 1H, NH); δ$_C$ (400 MHz, CDCl$_3$) 27.5, 45.1, 82.8, 115.6, 136.5, 144.8, 145.9, 167.0; LRMS (ES+) calculated for [C$_{12}$H$_{12}$F$_5$NO$_4$S+H]361.04. found 362.09.

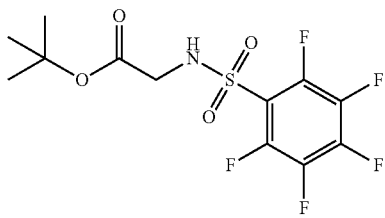 [SMILES: CC(C)(C)OC(=O)CNS(=O)(=O)c1c(F)c(F)c(F)c(F)c1F]

tert-butyl N-(4-chlorobenzyl)-N-((perfluorophenyl) sulfonyl)glycinate

Derivative 10 synthesized using general procedure e (71%): δ$_H$ (400 MHz, CDCl$_3$) 1.37 (s, 9H, (CH$_3$)$_3$), 3.93 (s, 2H, CH$_2$), 4.57 (s, 2H, CH$_2$), 7.24 (d, J=8.5 Hz, 2H, CH), 7.33 (d, J=8.5 Hz, 2H, CH); δ$_C$ (400 MHz, CDCl$_3$) 27.5, 52.5, 53.0, 81.8, 112.6, 126.5, 130.1, 132.4, 134.3, 136.5, 144.8, 145.9, 167.0; LRMS (ES+) calculated for [C₁₉H₁₇F₅ClNO₄S+H] 485.05. found 486.10.

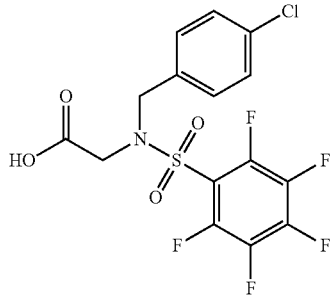 [SMILES: O=C(O)CN(Cc1ccc(Cl)cc1)S(=O)(=O)c1c(F)c(F)c(F)c(F)c1F]

N-(4-chlorobenzyl)-N-((perfluorophenyl)sulfonyl) glycine

Derivative 11 synthesized using general procedure f (92%): δ_H (400 MHz, CDCl₃) 4.13 (s, 2H, CH₂), 4.58 (s, 2H, CH₂), 7.25 (d, J=8.2 Hz, 2H, CH), 7.35 (d, J=8.2 Hz, 2H, CH); δ_C (400 MHz, CDCl₃) 52.8, 54.2, 112.6, 126.5, 130.1, 132.4, 134.3, 136.5, 144.8, 145.9, 172.0; LRMS (ES+) calculated for [C₁₅H₉F₅ClNO₄S+H] 428.99. found 429.99.

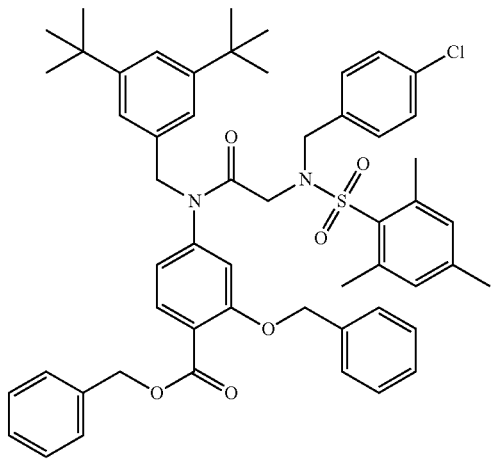 [SMILES: Cc1cc(C)c(S(=O)(=O)N(CC(=O)N(Cc2cc(C(C)(C)C)cc(C(C)(C)C)c2)c2ccc(C(=O)OCc3ccccc3)c(OCc3ccccc3)c2)Cc2ccc(Cl)cc2)c(C)c1]

Benzyl-2-(benzyloxy)-4-(2-((N-(4-chlorobenzyl)-2, 4,6-trimethylphenylsulfonamido)-N-(3,5-di-tert-butylbenzyl)acetamido)benzoate Derivative 12 synthesized using general procedure g (55%): δ_H (400 MHz, CDCl₃) 1.26 (s, 18H, (CH₃)₃), 2.31 (s, 3H, CH₃), 2.60 (s, 6H, CH₃), 3.58 (s, 2H, CH₂), 4.56 (s, 2H, CH₂), 4.75 (s, 4H, CH₂), 5.32 (s, 2H, CH₂), 6.24 (br s, 2H, CH), 6.93 (s, 2H, CH), 6.96 (s, 2H, CH), 7.03 (d, J=8.1 Hz, 2H, CH), 7.14 (d, J=8.1 Hz, 2H, CH), 6.93 (s, 2H, CH), 7.29-7.38 (m, 10H, CH), 7.70 (d, J=8.1 Hz, 1H, CH); δ_C (400 MHz, CDCl₃) 20.8, 22.8, 31.4, 34.6, 45.7, 49.5, 53.3, 66.9, 70.5, 113.5, 120.0, 121.3, 123.4, 127.0, 127.9, 128.0, 128.3, 128.4, 128.5, 130.3, 131.9, 132.6, 133.7, 135.4, 135.5, 140.3, 142.5, 150.9, 158.5, 165.2, 166.2; LRMS (ES+) calculated for [C₅₄H₅₉ClN₂O₆S+H] 898.38. found 899.39.

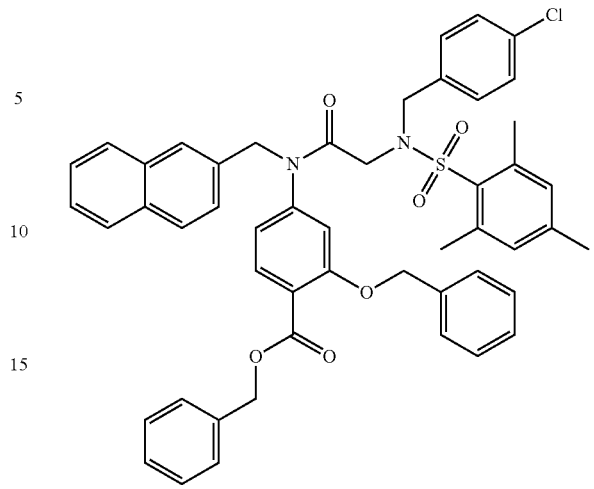

Benzyl 2-(benzyloxy)-4-(2-((N-(4-chlorobenzyl)-2, 4,6-trimethylphenylsulfonamido)-N-(napthalen-2-ylmethyl)acetamido)benzoate Derivative 12 synthesized using general procedure g (72%): δ_H (400 MHz, CDCl₃) 2.27 (s, 3H, CH₃), 2.59 (s, 6H, CH₃), 3.58 (s, 2H, CH₂), 4.62 (s, 2H, CH₂), 4.71 (s, 2H, CH₂), 4.86 (s, 2H, CH₂), 5.30 (s, 2H, CH₂), 6.21 (d, J=7.9 Hz, 1H, CH), 6.27 (s, 1H, CH), 6.94 (s, 2H, CH), 7.07 (d, J=8.5 Hz, 2H, CH), 7.16 (d, J=8.5 Hz, 2H, CH), 7.19 (d, J=8.1 Hz, 2H, CH), 7.22-7.27 (m, 2H, CH), 7.28-7.38 (m, 5H, CH), 7.42-7.53 (m, 4H, CH), 7.62-7.78 (m, 4H, CH), 7.82 (d, J=8.5 Hz, 1H, CH); δ_C (400 MHz, CDCl₃) 20.8, 22.8, 45.6, 49.9, 52.9, 66.9, 70.5, 126.0, 126.2, 126.8, 127.5, 127.6, 127.8, 128.0, 128.1, 128.2, 128.3, 128.4, 128.6, 130.1, 131.8, 132.5, 132.6, 132.9, 133.6, 133.8, 135.3, 135.5, 140.3, 142.5, 158.6, 165.1, 166.6; LRMS (ES+) calculated for [C₅₀H₄₅ClN₂O₆S+H] 836.27. found 837.28.

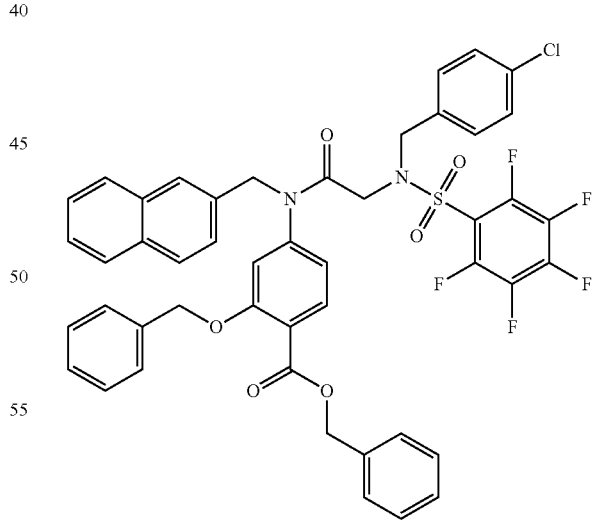

Benzyl 2-(benzyloxy)-4-(2-((N-(4-chlorobenzyl)-2, 3,4,5,6-pentafluorophenyl)sulfonamido)-N-(naptha-len-2-ylmethyl)acetamido)benzoate Derivative 12 synthesized using general procedure g (61%): δ_H (400 MHz, CDCl₃) 3.77 (s, 2H, CH₂), 4.67 (s, 2H, CH$_2$), 4.73 (s, 2H, CH$_2$), 4.83 (s, 2H, CH$_2$), 5.29 (s, 2H, CH$_2$), 6.31 (d, 1H, CH), 6.39 (d, J=8.3 Hz, 1H, CH), 7.13-7.23 (m, 5H, CH), 7.23-7.29 (m, 5H, CH), 7.29-7.36 (m, 5H, CH), 7.41 (s, 1H, CH), 7.45-7.54 (m, 2H, CH), 7.64-7.75 (m, 2H, CH), 7.78 (d, J=8.4 Hz, 1H, CH), 7.81-7.89 (m, 1H, CH); δ$_C$ (400 MHz, CDCl$_3$) 47.5, 50.5, 53.0, 66.9, 70.6, 113.2, 119.5, 121.3, 126.1, 126.3, 126.9, 127.5, 127.9, 128.1, 128.3, 128.4, 128.9, 129.9, 132.7, 132.9, 133.1, 133.2, 134.3, 135.2, 135.4, 143.7, 158.7, 165.0, 165.8; LRMS (ES+) calculated for [C$_{47}$H$_{34}$ClF$_5$N$_2$O$_6$S+H] 884.17. found 885.19.

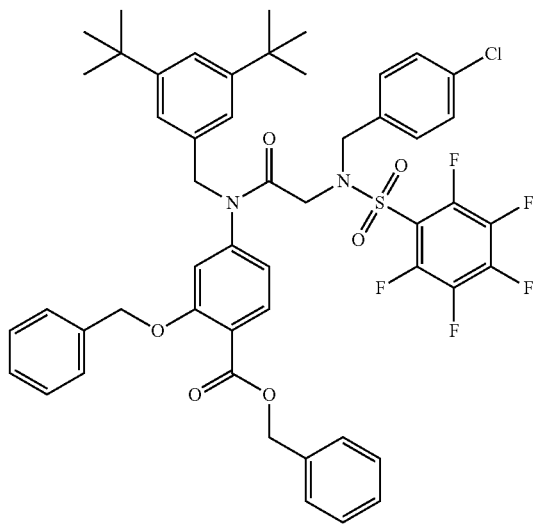 [SMILES: CC(C)(C)c1cc(CN(C(=O)CN(Cc2ccc(Cl)cc2)S(=O)(=O)c2c(F)c(F)c(F)c(F)c2F)c2ccc(C(=O)OCc3ccccc3)c(OCc3ccccc3)c2)cc(C(C)(C)C)c1]

Benzyl-2-(benzyloxy)-4-(2-((N-(4-chlorobenzyl)-2, 3,4,5,6-pentafluorophenyl)sulfonamido)-N-(3, 5-di-tert-butylbenzyl)acetamido)benzoate Derivative 12 synthesized using general procedure g (61%): δ$_H$ (400 MHz, CDCl$_3$) 1.25 (s, 18H, (CH$_3$)$_3$), 3.75 (s, 2H, CH$_2$), 4.63 (s, 2H, CH$_2$), 4.70 (s, 2H, CH$_2$), 4.76 (s, 2H, CH$_2$), 5.30 (s, 2H, CH$_2$), 6.25 (s, 1H, CH), 6.33 (d, J=8.1 Hz, 1H, CH), 6.85 (s, 2H, CH), 7.17 (d, J=8.5 Hz, 2H, CH), 7.25 (d, J=8.5 Hz, 2H, CH), 7.28-7.37 (m, 12H, CH), 7.78 (d, J=8.1 Hz, 1H, CH); δ$_C$ (400 MHz, CDCl$_3$) 31.1 34.5, 47.6, 50.3, 53.3, 111.3, 116.2, 117.2, 118.9, 121.6, 123.0, 128.9, 129.9, 132.0, 132.5, 134.3, 134.4, 136.4, 138.9, 143.5, 145.0, 145.9, 146.8, 151.0, 162.7, 165.3, 172.2; LRMS (ES+) calculated for [C$_{51}$H$_{48}$ClF$_5$N$_2$O$_6$S+H] 946.28. found 947.30.

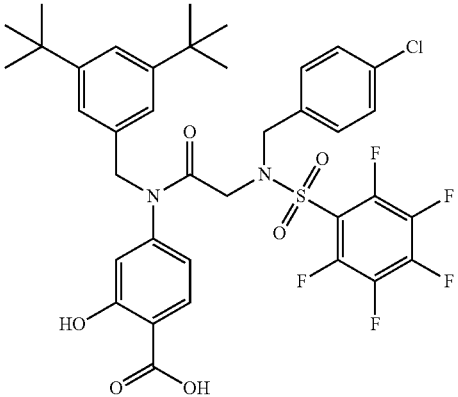 [SMILES: CC(C)(C)c1cc(CN(C(=O)CN(Cc2ccc(Cl)cc2)S(=O)(=O)c2c(F)c(F)c(F)c(F)c2F)c2ccc(C(=O)O)c(O)c2)cc(C(C)(C)C)c1]

4-(2-((N-(4-chlorobenzyl)-2,3,4,5,6-pentafluorophenyl)sulfonamido)-N-(3,5-di-tert-butylbenzyl)acetamido)-2-hydroxybenzoic Acid Derivative 13a synthesized using general procedure h (76%): δ$_H$ (400 MHz, CDCl$_3$) 1.25 (s, 18H, (CH$_3$)$_3$), 3.80 (s, 2H, CH$_2$), 4.61 (s, 2H, CH$_2$), 4.73 (s, 2H, CH$_2$), 6.25 (s, 1H, CH), 6.36 (s, 1H, CH), 6.88 (s, 2H, CH), 7.15 (d, J=8.5 Hz, 2H, CH), 7.24 (d, J=8.5 Hz, 2H, CH), 7.31 (s, 1H, CH), 7.75 (d, J=8.5 Hz, 1H, CH); δ$_C$ (400 MHz, CDCl$_3$) 31.1, 34.5, 47.6, 50.3, 121.6, 128.7, 128.9, 129.9, 132.5, 134.4, 151.0, 162.7, 172.4; LRMS (ES+) calculated for [C$_{37}$H$_{36}$ClF$_5$N$_2$O$_6$S+H] 766.19. found 765.18; HPLC (I), (II) tR=48.22 min (95.25%).

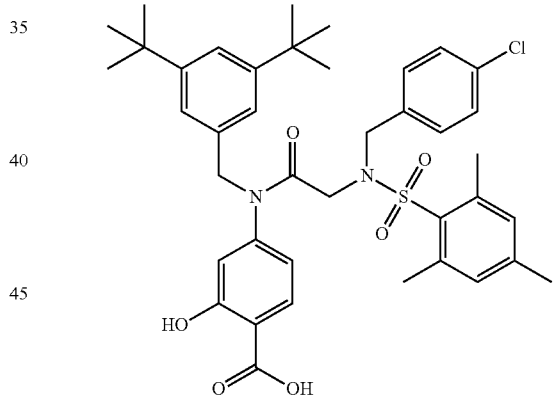

4-(2-((N-(4-chlorobenzyl)-2,4,6-trimethylphenyl)sulfonamido)-N-(3,5-di-tert-butylbenzyl)acetamido)-2-hydroxybenzoic Acid Derivative 13b synthesized using general procedure h (59%): δ$_H$ (400 MHz, CDCl$_3$) 1.25 (s, 18H, (CH$_3$)$_3$), 2.29 (s, 3H, CH$_3$), 2.60 (s, 6H, CH$_3$) 3.59 (s, 2H, CH$_2$), 4.60 (s, 2H, CH$_2$), 4.72 (s, 2H, CH$_2$), 6.11 (s, 1H, CH), 6.25 (s, 1H, CH), 6.92 (s, 2H, CH), 6.96 (s, 2H, CH), 7.05 (d, J=8.3 Hz, 2H, CH), 7.14 (d, J=8.3 Hz, 2H, CH), 7.31 (s, 1H, CH), 7.73 (d, J=8.3 Hz, 1H, CH); δ$_C$ (400 MHz, CDCl$_3$) 20.6, 20.8, 22.7, 31.2, 34.5, 45.6, 49.6, 53.3, 117.1, 118.9, 121.4, 123.2, 128.6, 130.2, 131.9, 132.4, 133.6, 133.7, 134.8, 140.3, 142.6, 147.3, 150.8, 162.6, 166.1, 173.1, 177.4; LRMS (ES+) calculated for [C$_{40}$H$_{47}$ClN$_2$O$_6$S+H] 718.28. found 717.3; HPLC (I) tR=32.08 min (97.63%), (II) tR=49.69 min (97.12%).

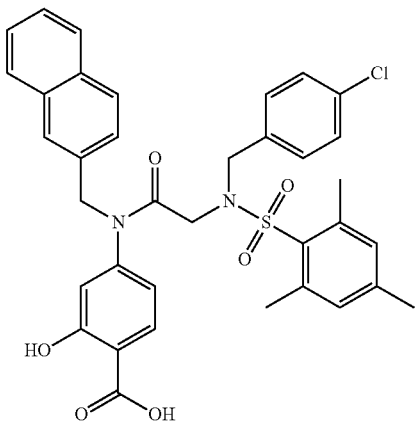 [SMILES: Cc1cc(C)c(S(=O)(=O)N(CC(=O)N(Cc2ccc3ccccc3c2)c2ccc(C(=O)O)c(O)c2)Cc2ccc(Cl)cc2)c(C)c1]

4-(2-((N-(4-chlorobenzyl)-2,4,6-trimethylphenyl)sulfonamido)-N-(naphthalene-2-ylmethyl)acetamido)-2-hydroxybenzoic Acid Derivative 13c synthesized using general procedure h (72%): $\delta_H$ (400 MHz, CDCl$_3$) 2.34 (s, 3H, CH$_3$) 2.63 (s, 6H, CH$_3$) 3.88 (s, 2H, CH$_2$), 4.40 (s, 2H, CH$_2$), 4.90 (s, 2H, CH$_2$), 6.31 (s, 1H, CH), 6.51 (s, 1H, CH), 7.03 (s, 2H, CH), 7.08 (d, J=8.3 Hz, 2H, CH) 7.20 (d, J=8.3 Hz, 2H, CH), 7.44-7.49 (m, 2H, CH), 7.67-7.93 (m, 5H, CH); $\delta_C$ (400 MHz, CDCl$_3$) 21.0, 23.0, 47.5, 50.5, 53.0, 107.0, 107.2, 110.7, 125.1, 126.0, 127.6, 1270, 127.3, 128.6, 130.1, 131.7, 132.5, 133.7, 134.2, 135.2, 137.7, 141.1, 143.8, 145.1, 148.3, 163.1, 166.9, 173.2 LRMS (ES+) calculated for [C$_{36}$H$_{33}$ClN$_2$O$_6$S+H] 656.17. found 655.20. HPLC (I) tR=# min (#%), (II) tR=# min (#%). Fill in the blanks

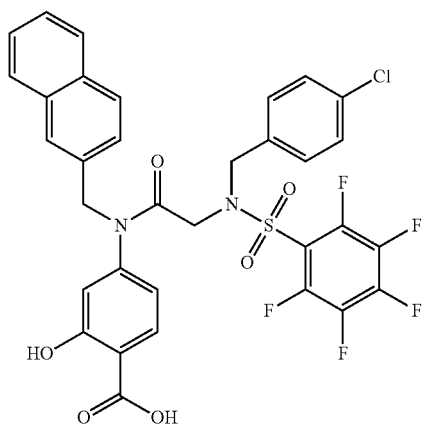 [SMILES: O=C(O)c1ccc(N(Cc2ccc3ccccc3c2)C(=O)CN(Cc2ccc(Cl)cc2)S(=O)(=O)c2c(F)c(F)c(F)c(F)c2F)cc1O]

4-(2-((N-(4-chlorobenzyl)-2,3,4,5,6-pentafluorophenyl)sulfonamido)-N-(-naphthalene-2-ylmethyl)acetamido)-2-hydroxybenzoic Acid Derivative 13d synthesized using general procedure h (61%): $\delta_H$ (400 MHz, CDCl$_3$) 3.88 (s, 2H, CH$_2$), 4.66 (s, 2H, CH$_2$), 4.90 (s, 2H, CH$_2$), 6.31 (s, 1H, CH), 6.51 (s, 1H, CH), 7.15-7.36 (m, 4H, CH), 7.41-7.57 (m, 3H, CH), 7.67-7.93 (m, 5H, CH); $\delta_C$ (400 MHz, CDCl$_3$) 47.5, 50.5, 53.1, 66.9, 70.6, 113.2, 119.6, 121.2, 126.2, 126.3, 126.9, 127.5, 127.6, 127.8, 127.9, 128.1, 128.4, 128.6, 128.9, 129.9, 132.7, 132.9, 133.1, 133.2, 134.3, 135.2, 135.4, 143.7, 158.7, 165.0, 165.8; LRMS (ES+) calculated for [C$_{33}$H$_{22}$ClF$_5$N$_2$O$_6$S+H]704.08. found 703.09; HPLC (I) tR=26.58 min (94.41%), (II) tR=41.17 min (84.06%).

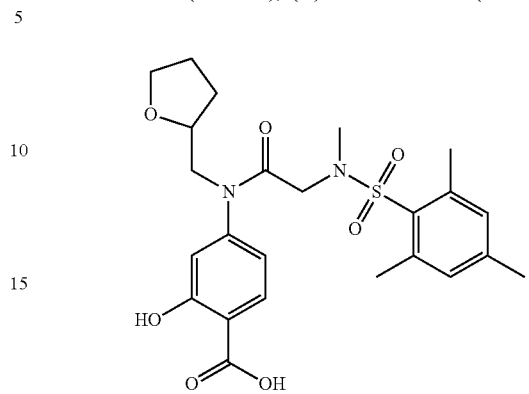

2-(hydroxy)-4-(N-(tetrahydrofuran-2-yl)methyl)-2-(N, 2,4,6 tetramethylphenylsulfonamido)acetamido) benzoic Acid Derivative 8a hydrogenated on a 0.3 mmol scale via general procedure h (95%): $\delta_H$ (400 MHz, d-CDCl$_3$) 1.79-2.04 (m, 4H, 2CH$_2$), 2.29 (s, 3H, CH$_3$(Ph)), 2.57 (s, 6H, 2CH$_3$(Ph)), 2.82 (s, 3H, CH$_3$NSO$_2$), 3.61-3.79 (m, 2H, COCH$_2$), 3.80-3.89 (m, 4H, NHCH$_2$ THF, O—CH$_2$), 4.02-4.17 (m, 1H, CH), 6.72 (d, J=8.3 Hz, 1H, CH (Ph)), 6.79 (s, 1H, CH (Ph)), 6.93 (s, 2H, CH), 7.83 (d, J=8.3 Hz, 1H, CH); $\delta_C$ (100 MHz, d-CDCl$_3$) 21.1, 22.9, 25.4, 29.3, 29.8, 34.9, 49.9, 53.3, 68.1, 117.1, 119.1, 131.7, 132.1, 132.3, 140.8, 142.9, 148.0, 163.1; HRMS (ES+) Calculated for [C$_{24}$H$_{30}$N$_2$O$_7$S+H] 490.18. found 491.20; HPLC (I) tR=16.45 min (96.95%), (II) tR=24.99 min (96.49%).

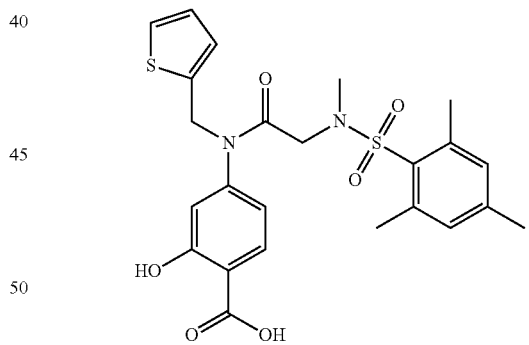

2-(hydroxy)-4-(2-((N, 2,4,6 tetramethylphenylsulfonamido)-N-(thiophen-2-ylmethyl)acetamido)benzoic Acid Derivative 8b hydrogenated on a 0.2 mmol scale via general procedure h (82%); $\delta_H$ (400 MHz, d-CDCl$_3$) 2.28 (s, 3H, CH$_3$(Ph)), 2.57 (s, 6H, 2CH$_3$), 2.85 (s, 3H, CH$_3$NSO$_2$), 3.79 (s, 2H, COCH$_2$), 4.94 (s, 2H, CH$_2$Ar), 6.48 (d, 1H, J=8.3 Hz, CH), 6.58 (s, 1H, CH), 6.77 (d, 1H, J=3.1 Hz, CH), 6.85-6.87 (m, 1H, CH), 6.93 (s, 2H, CH), 7.21 (d, 1H, J=5.3 Hz, CH), 7.88 (d, 1H, J=8.4 Hz, CH); $\delta_C$ (100 MHz, d-CDCl$_3$): 20.8, 22.6, 29.5, 34.6, 47.6, 49.5, 118.8, 125.9, 126.4, 127.5, 131.4, 131.8, 132.4, 138.3, 140.6, 142.6, 165.2; HRMS (ES+) Calculated for [C$_{24}$H$_{26}$N$_2$O$_6$S$_2$+H] 502.12. found 503.1; HPLC (I) tR=18.77 min (87.95%), (II) tR=29.19 min (87.95%).

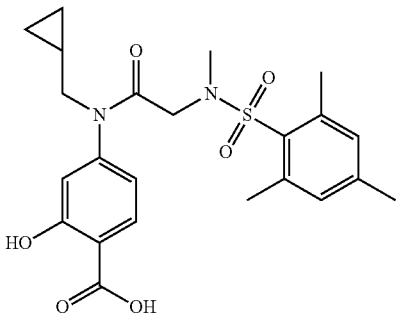 [SMILES: Cc1cc(C)c(S(=O)(=O)N(C)CC(=O)N(CC2CC2)c2ccc(C(=O)O)c(O)c2)c(C)c1]

4-(N-(cyclopropylmethyl)-2-((N,2,4,6 tetramethylphenyl)sulfonamido)-acetamido)-2-benzoic Acid Derivative 8d hydrogenated on a 0.3 mmol scale via general procedure h (90%); δ$_H$ (400 MHz, d-CDCl$_3$) 0.05-0.18 (m, 2H, CH$_2$), 0.37-0.49 (m, 2H, CH$_2$), 0.77-0.97 (m, 1H, CH), 2.28 (s, 3H, CH$_3$), 2.57 (s, 6H, CH$_3$), 2.83 (s, 3H, CH$_3$), 3.53 (d, J=71.2 Hz, 2H), 3.79 (s, 2H, CH$_2$), 6.71 (d, J=8.4 Hz, 1H CH), 6.77 (d, J=1.4 Hz, 1H, CH), 6.94 (s, 2H, CH), 7.94 (d, J=8.4 Hz, 1H, CH); δ$_C$ (100 MHz, d-CDCl$_3$): 3.6, 9.6, 20.6, 20.8, 22.6, 29.5, 34.7, 49.5, 53.6, 111.9, 117.2, 119.2, 131.5, 131.8, 132.3, 140.6, 142.6, 147.9, 162.9, 166.7, 172.7, 177.3; HRMS (ES+) Calculated for [C$_{23}$H$_{26}$N$_2$O$_6$S+H] 460.17. found 461.2; HPLC (I) tR=18.10 min (93.12%), (II) tR=27.83 min (93.25%).

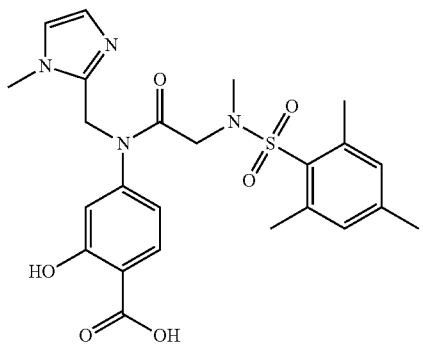

2-hydroxy-4-(N-((1-methyl-1H-imidazol-2-yl)methyl)-2-((N,2,4,6 tetramethylphenyl)sulfonamido)-acetamido)benzoic Acid Derivative 8c hydrogenated on a 0.15 mmol scale via general procedure h (40%); δ$_H$ (400 MHz, d-CDCl$_3$) 2.28 (s, 3H, CH$_3$), 2.50 (s, 6H, CH$_3$), 2.81 (s, 3H, CH$_3$), 3.78 (s, 2H, CH$_2$), 4.06 (s, 2H, CH$_2$), 6.40 (d, J=8.4 Hz, 1H, CH), 6.46 (s, 1H, CH), 6.91 (s, 2H, CH), 7.00 (s, 1H, CH), 7.25 (s, 1H, CH), 7.65 (d, J=8.2 Hz, 1H, CH); δ$_C$ (100 MHz, d-CDCl$_3$): 20.8, 22.6, 33.1, 34.6, 47.8, 49.5, 106.0, 113.2, 120.5, 127.1, 131.4, 131.9, 138.2, 140.6, 142.9, 147.3, 152.4, 164.8, 166.9, 171.8; HRMS (ES+) Calculated for [C$_{24}$H$_{28}$N$_4$O$_6$S+H] 500.17. found 501.20; HPLC (I) tR=10.65 min (98.04%), (II) tR=15.79 min (83.06%).

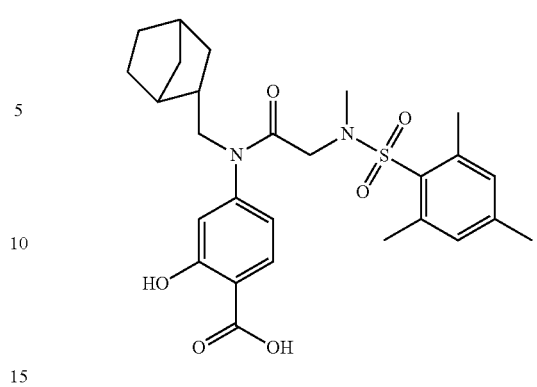

4-(N-(bicycle[2.2.1]heptan-2-ylmethyl)-2-((N,2,4,6 tetramethylphenyl)sulfonamido)-acetamido)-2-hydroxybenzoic Acid Derivative 8e hydrogenated on a 0.14 mmol scale via general procedure h (35%); δ$_H$ (400 MHz, d-CDCl$_3$) 0.78-1.06 (m, 2H, CH$_2$), 1.07-1.22 (m, 2H, CH$_2$), 1.29-1.60 (m, 3H, CH$_2$, CH), 1.82-2.04 (m, 2H, CH), 2.22 (s, 3H, CH$_3$), 2.47 (s, 6H, CH$_3$), 2.70 (s, 3H, CH$_3$), 3.45 (s, 2H, CH$_2$), 3.63 (s, 2H, CH$_2$), 3.81 (s, 2H, CH$_2$), 6.51 (d, J=8.0 Hz, 1H, CH), 6.64 (s, 1H, CH), 6.86 (s, 2H, CH), 7.85 (d, J=8.0 Hz, 1H, CH); δ$_C$(100 MHz, d-CDCl$_3$): 20.8, 22.5, 22.6, 29.7, 34.3, 34.4, 36.7, 38.7, 39.6, 51.3, 131.5, 131.8, 137.2, 140.4, 142.5, 148.3, 164.4, 166.2, 171.3; HRMS (ES+) Calculated for [C$_{27}$H$_{34}$N$_2$O$_6$S+H] 514.21. found 515.20; HPLC (I) tR=22.48 min (99.40%), (II) tR=35.27 min (96.56%).

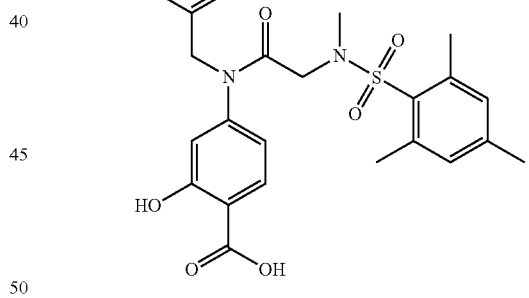

4-(N-benzyl-2-((N,2,4,6 tetramethylphenyl)sulfonamido)-acetamido)-2-hydroxybenzoic Acid Derivative 8g hydrogenated on a 0.07 mmol scale via general procedure h (75%); δ$_H$ (400 MHz, d-CDCl$_3$) 2.29 (s, 3H, CH$_3$), 2.57 (s, 6H, CH$_3$), 2.87 (s, 3H, CH$_3$), 3.81 (s, 2H, CH$_2$), 4.82 (s, 2H, CH$_2$), 6.41 (d, J=8.1 Hz, 1H, CH), 6.54 (s, 1H, CH), 6.94 (s, 2H, CH), 7.06-7.16 (m, 2H, CH), 7.18-7.25 (m, 3H, CH), 7.84 (d, J=8.5 Hz, 1H, CH); δ$_C$(100 MHz, d-CDCl$_3$): 20.8, 22.6, 34.6, 49.6, 52.9, 118.8, 127.6, 128.4, 131.6, 131.8, 136.2, 140.5, 142.5, 166.8; HRMS (ES+) Calculated for [C$_{26}$H$_{28}$N$_2$O$_6$S+H] 496.17. found 497.17; HPLC (I) tR=19.17 min (98.29%), (II) tR=29.81 min (97.35%).

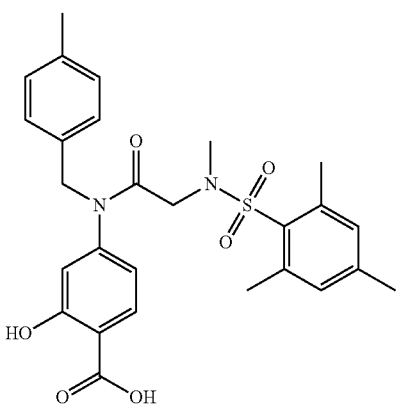 [SMILES: Cc1ccc(CN(C(=O)CN(C)S(=O)(=O)c2c(C)cc(C)cc2C)c2ccc(C(=O)O)c(O)c2)cc1]

2-hydroxy-4-(N-(4-methylbenzyl)-2-((N,2,4,6-tetramethylphenyl)sulfonamido)-acetamido)benzoic Acid Derivative 8f hydrogenated on a 0.04 mmol scale via general procedure h (85%); $\delta_H$ (400 MHz, d-CDCl$_3$) 2.30 (s, 3H, CH$_3$), 2.57 (s, 6H, CH$_3$), 2.87 (s, 3H, CH$_3$), 3.79 (s, 2H, CH$_2$), 4.77 (s, 2H, CH$_2$), 6.41 (d, J=8.5 Hz, 1H, CH), 6.52 (s, 1H, CH), 6.93 (s, 2H, CH), 6.98 (d, J=8.3 Hz, 2H, CH), 7.04 (d, J=8.3 Hz, 2H, CH), 7.82 (d, J=8.3 Hz, 1H, CH); $\delta_C$ (100 MHz, d-CDCl$_3$): 20.8, 20.9, 22.6, 31.7, 34.6, 36.8, 49.5, 52.6, 116.7, 118.7, 128.3, 129.0, 131.5, 131.7, 132.0, 133.2, 137.2, 140.5, 142.5, 147.1, 162.7, 163.3, 166.7, 171.8; HRMS (ES+) Calculated for [C$_{26}$H$_{28}$N$_2$O$_6$S+H] 510.18. found 511.20; HPLC (I) tR=20.32 min (95.53%), (II) tR=31.81 min (93.81%).

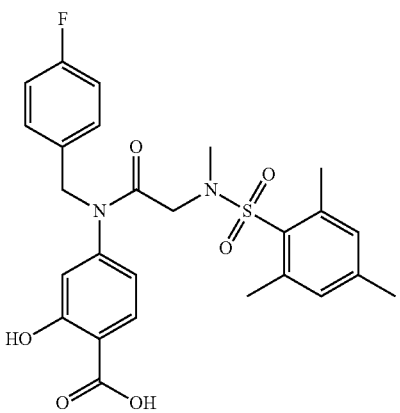 [SMILES: Cc1cc(C)c(S(=O)(=O)N(C)CC(=O)N(Cc2ccc(F)cc2)c2ccc(C(=O)O)c(O)c2)c(C)c1]

4-(N-(4-fluorobenzyl)-2-((N,2,4,6-tetramethylphenyl)sulfonamido)-acetamido)-2-hydroxybenzoic Acid Derivative 8h hydrogenated on a 0.1 mmol scale via general procedure h (89%); $\delta_H$ (400 MHz, d-CDCl$_3$): 2.29 (s, 3H, CH$_3$), 2.57 (s, 6H, CH$_3$), 2.86 (s, 3H, CH$_3$), 3.82 (s, 2H, CH$_2$), 4.79 (s, 2H, CH$_2$), 6.43 (d, J=8.3 Hz, 1H, CH), 6.55 (s, 1H, CH), 6.84-7.01 (m, 4H, CH), 7.02-7.17 (m, 2H, CH), 7.85 (d, J=8.3 Hz, 1H, CH); $\delta_C$ (100 MHz, d-CDCl$_3$): 20.8, 22.6, 29.5, 34.8, 49.6, 52.2, 111.7, 115.2, 115.4, 116.9, 118.9, 130.2, 130.3, 131.4, 131.8, 132.0, 132.3, 140.5, 142.6, 147.2, 160.9, 162.8, 163.4, 166.8, 171.8; HRMS (ES+) Calculated for [C$_{26}$H$_{27}$FN$_2$O$_6$S+H]514.16. found 515.20; HPLC (I) tR=19.48 min (96.92%), (II) tR=30.84 min (92.79%).

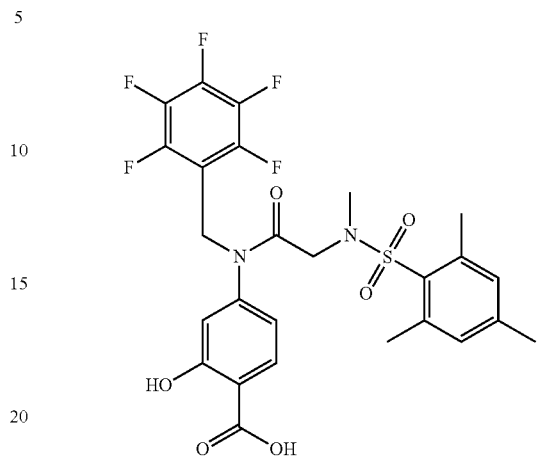

2-hydroxy-4-(N-((perfluorophenyl)methyl)-2-((N,2,4,6-tetramethylphenyl)sulfonamido)-acetamido)benzoic Acid Derivative 8i hydrogenated on a 0.16 mmol scale via general procedure h (90%); 6H (400 MHz, d-DMSO): 2.24 (s, 3H, CH$_3$), 2.40 (s, 6H, CH$_3$), 2.73 (s, 3H, CH$_3$), 3.71 (s, 2H, CH$_2$), 4.93 (s, 2H, CH$_2$), 6.60 (d, J=8.5 Hz, 1H, CH), 6.79 (s, 1H, CH), 6.97 (s, 2H, CH), 7.76 (d, J=8.4 Hz, 1H, CH); $\delta_C$ (100 MHz, d-DMSO): 20.8, 22.6, 34.6, 36.8, 49.5, 115.4, 131.6, 136.4, 141.3, 145.3, 162.9, 166.7, 172.7; HRMS (ES+) Calculated for [C$_{26}$H$_{23}$F$_5$N$_2$O$_6$S+H] 586.12. found 587.10; HPLC (I) tR=20.63 min (99.83%), (II) tR=32.50 min (98.56%).

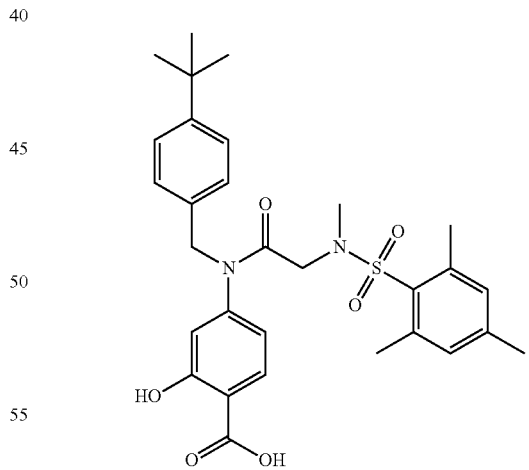

4-(N-(4-(tert-butyl)benzyl)-2-((N,2,4,6-tetramethylphenyl)sulfonamido)-acetamido)-2-hydroxybenzoic Acid Derivative 8k hydrogenated on a 0.08 mmol scale via general procedure h (40%); $\delta_H$ (400 MHz, d-CDCl$_3$): 1.29 (s, 9H, CH$_3$), 2.29 (s, 3H, CH$_3$), 2.57 (s, 6H, CH$_3$), 2.86 (s, 3H, CH$_3$), 3.81 (s, 2H, CH$_2$), 4.79 (s, 2H, CH$_2$), 6.47 (d, J=8.5 Hz, 1H, CH), 6.57 (s, 1H, CH), 6.94 (s, 2H, CH), 7.03 (d, J=8.2 Hz, 2H, CH), 7.27 (d, J=8.2 Hz, 2H, CH), 7.84 (d, J=8.4 Hz, 1H, CH); δ$_C$(100 MHz, d-CDCl$_3$): 20.5, 20.8, 22.6, 31.1, 34.3, 34.6, 49.5, 52.7, 116.8, 118.9, 125.3, 127.9, 131.5, 131.7, 132.2, 133.1, 140.5, 142.5, 150.5, 162.7, 166.7, 173.0, 177.0; HRMS (ES+) Calculated for [C$_{30}$H$_{36}$F$_5$N$_2$O$_6$S+H] 552.23. found 553.20; HPLC (I) tR=23.33 min (98.57%), (II) tR=37.15 min (98.89%).

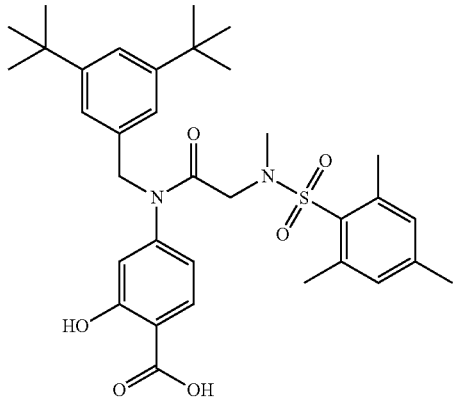 [SMILES: Cc1cc(C)c(S(=O)(=O)N(C)CC(=O)N(Cc2cc(C(C)(C)C)cc(C(C)(C)C)c2)c2ccc(C(=O)O)c(O)c2)c(C)c1]

4-(N-(3,5-di-tert-butylbenzyl)-2-((N,2,4,6-tetramethylphenyl)sulfonamido)-acetamido)-2-hydroxybenzoic Acid Derivative 81 hydrogenated on a 0.07 mmol scale via general procedure h (65%); δ$_H$ (400 MHz, d-CDCl$_3$): 1.24 (s, 18H, CH$_3$), 2.28 (s, 3H, CH$_3$), 2.58 (s, 6H, CH$_3$), 2.81 (s, 3H, CH$_3$), 3.83 (s, 2H, CH$_2$), 4.83 (s, 2H, CH$_2$), 6.46 (d, J=8.4 Hz, 1H, CH), 6.55 (s, 1H, CH), 6.93 (s, 2H, CH), 6.95 (s, 2H, CH), 7.28 (s, 1H, CH), 7.83 (d, J=8.4 Hz, 1H, CH); δ$_C$(100 MHz, d-CDCl$_3$): 20.5, 20.8, 22.6, 31.2, 34.4, 34.5, 49.5, 53.4, 121.3, 122.9, 131.4, 131.7, 132.0, 135.0, 140.5, 142.5, 150.8, 162.7, 177.1; HRMS (ES+) Calculated for [C$_{34}$H$_{44}$N$_2$O$_6$S+H] 608.29. found 609.30; HPLC (I) tR=26.49 min (99.72%), (II) tR=42.87 min (98.62%).

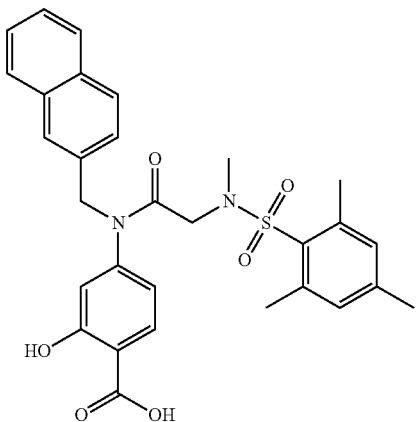 [SMILES: Cc1cc(C)c(S(=O)(=O)N(C)CC(=O)N(Cc2ccc3ccccc3c2)c2ccc(C(=O)O)c(O)c2)c(C)c1]

2-hydroxy-4-(N-(napthalen-2-ylmethyl)-2-((N,2,4,6-tetramethylphenyl)sulfonamido)-acetamido)benzoic Acid Derivative 8j hydrogenated on a 0.09 mmol scale via general procedure h (40%); δ$_H$ (400 MHz, d-CDCl$_3$): 2.24 (s, 3H, CH$_3$), 2.57 (s, 6H, CH$_3$), 2.89 (s, 3H, CH$_3$), 3.84 (s, 2H, CH$_2$), 4.99 (s, 2H, CH$_2$), 6.42 (d, J=8.2 Hz, 1H, CH), 6.58 (s, 1H, CH), 6.91 (s, 2H, CH), 7.27 (s, 1H, CH), 7.38-7.50 (m, 2H, CH), 7.54 (s, 1H, CH), 7.68-7.88 (m, 4H, CH); δ$_C$(100 MHz, d-CDCl$_3$): 20.5, 20.7, 22.6, 34.7, 49.6, 53.1, 111.8, 116.8, 118.9, 125.9, 126.1, 127.5, 127.6, 128.3, 131.4, 131.8, 132.2, 132.6, 133.0, 133.6, 140.5, 142.5 147.4, 162.8, 167.0, 172.5, 177.0; HRMS (ES+) Calculated for [C$_{30}$H$_{30}$N$_2$O$_6$S+H] 546.18. found 547.20; HPLC (I) tR=21.21 min (97.90%), (II) tR=33.46 min (95.26%).

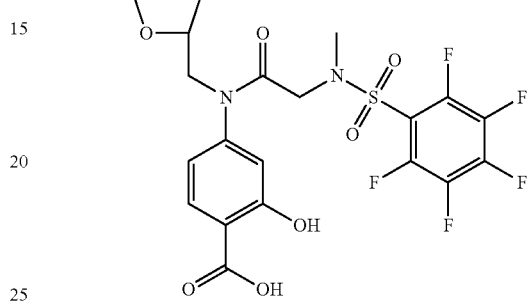

2-hydroxy-4-(2-((2,3,4,5,6-pentafluoro-N-methylphenyl)sulfonamido)-N-((tetrahydrofuran-2-yl)methyl)acetamido)benzoic Acid Derivative 8m hydrogenated on a 0.1 mmol scale via general procedure h (70%); δ$_H$ (400 MHz, d-CDCl$_3$): 1.41-1.60 (m, 1H, CH), 1.79-2.01 (m, 3H, CH$_2$, CH), 3.07 (s, 3H, CH$_3$), 3.67 (d, J=6.5 Hz, 2H, CH$_2$), 3.71-3.89 (m, 2H, CH$_2$), 3.93-4.21 (m, 2H, CH$_2$), 6.80 (d, J=8.2 Hz, 1H, CH), 6.89 (s, 1H, CH), 7.95 (d, J=8.3 Hz, 1H, CH); δ$_C$ (100 MHz, d-CDCl$_3$): 20.5, 25.2, 28.8, 31.7, 35.7, 36.8, 52.0, 52.9, 67.7, 116.7, 118.6, 132.3, 146.9, 162.9, 163.3, 171.9, 176.1; HRMS (ES+) Calculated for [C$_{21}$H$_{19}$F$_5$N$_2$O$_7$S+H] 538.08. found 539.10; HPLC (I) tR=24.63 min (97.67%), (II) tR=26.45 min (95.84%).

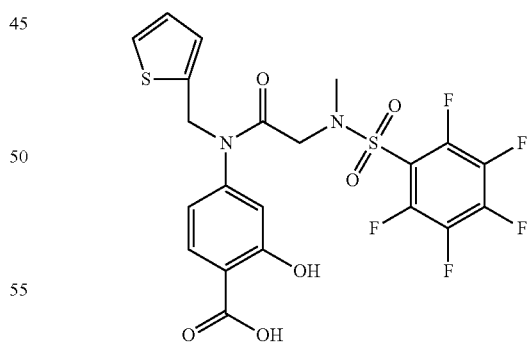

2-hydroxy-4-(2-((2,3,4,5,6-pentafluoro-N-methylphenyl)sulfonamide)-N-(thiophen-2-ylmethyl)acetamido)benzoic Acid Derivative 8n hydrogenated on a 0.1 mmol scale via general procedure h (95%): δ$_H$ (400 MHz, d-CDCl$_3$) 3.03 (s, 3H, CH$_3$), 3.97 (s, 2H, CH$_2$), 4.83 (s, 2H, CH$_2$), 6.52 (d, J=8.3 Hz, 1H, CH), 6.65 (s, 1H, CH), 6.68 (s, 1H, CH), 6.78-6.85 (m, 1H, CH), 7.17 (d, J=5.4 Hz, 1H, CH), 7.87 (d, J=8.4 Hz, 1H, CH); δ$_C$ (100 MHz, d-CDCl$_3$) 20.5, 22.6, 29.3, 29.6, 31.6, 32.3, 34.2, 35.9, 47.8, 52.0, 52.2, 112.1, 117.1, 119.0, 126.3, 126.6, 127.6, 132.7, 137.8, 146.8, 147.1, 163.1, 163.2, 165.7, 172.5, 176.5; HRMS (ES+) Calculated for [C$_{21}$H$_{15}$F$_5$N$_2$O$_6$S$_2$+H]550.03. found 551.0; HPLC (I) tR=26.91 min (64.94%), (II) tR=30.17 min (92.72%).

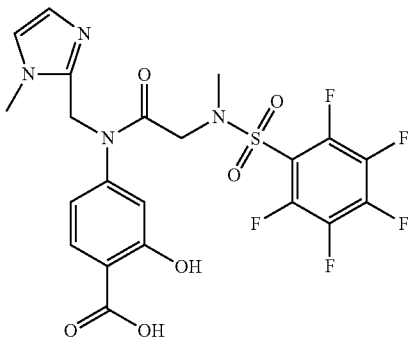 [SMILES: CN(CC(=O)N(Cc1nccn1C)c1ccc(C(=O)O)c(O)c1)S(=O)(=O)c1c(F)c(F)c(F)c(F)c1F]

2-hydroxy-4-(N-((1-methyl-1H-imidazol-2-yl) methyl)-2-((2,3,4,5,6-pentafluoro-N-methylphenyl) sulfonamido)acetamido)benzoic Acid Derivative 8o hydrogenated on a 0.16 mmol scale via general procedure h (54%): δ$_H$ (400 MHz, d-DMSO) 2.94 (s, 3H, CH$_3$), 3.60 (s, 3H, CH$_3$), 3.61 (s, 2H, CH$_2$), 4.99 (s, 2H, CH$_2$), 6.64 (s, 1H, CH), 6.78 (s, 1H, CH), 7.18 (s, 1H, CH), 7.37 (s, 1H, CH), 7.72 (s, 1H, CH); δ$_C$ (100 MHz, d-DMSO); 33.1, 34.6, 47.8, 49.5, 106.0, 113.2, 120.5, 127.1, 131.4, 131.9, 138.2, 140.6, 142.9, 147.3, 152.4, 164.8, 166.9, 171.8; HRMS (ES+) Calculated for [C$_{21}$H$_{17}$F$_5$N$_4$O$_6$S$_2$+H] 548.08. found 549.10; HPLC (I) tR=17.52 min (74.54%), (II) tR=15.87 min (79.92%).

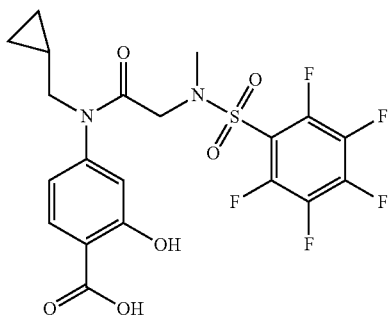 [SMILES: CN(CC(=O)N(CC1CC1)c1ccc(C(=O)O)c(O)c1)S(=O)(=O)c1c(F)c(F)c(F)c(F)c1F]

4-(N-(cyclopropylmethyl)-2-((2,3,4,5,6-pentafluoro-N-methylphenyl)sulfonamido)acetamido)-2-hydroxybenzoic Acid Derivative 8p hydrogenated on a 0.4 mmol scale via general procedure h (87%): δ$_H$ (400 MHz, d-CDCl$_3$) 0.04-0.18 (m, 2H, CH$_2$), 0.40-0.59 (m, 2H, CH$_2$), 0.78-1.00 (m, 1H, CH), 3.07 (s, 3H, CH$_3$), 3.49 (d, J=7.2 Hz, 2H, CH$_2$), 4.04 (s, 2H, CH$_2$), 6.83 (s, 1H, CH), 6.90 (s, 1H, CH), 8.00 (d, J=8.3 Hz, 1H, CH); δ$_C$ (100 MHz, d-CDCl$_3$): 3.5, 9.4, 20.5, 35.8, 52.0, 53.8, 111.9, 117.2, 119.1, 132.6, 147.4, 163.0, 165.7, 172.9; HRMS (ES+) calculated for [C$_{20}$H$_{17}$F$_5$N$_2$O$_6$S$_2$+H] 508.07. found 509.10; HPLC (I) tR=26.33 min (97.61%), (II) tR=29.31 min (96.90%).

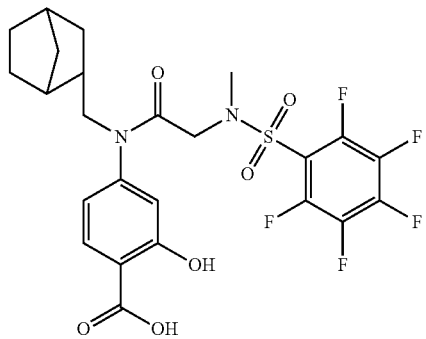 [SMILES: CN(CC(=O)N(CC1CC2CCC1C2)c1ccc(C(=O)O)c(O)c1)S(=O)(=O)c1c(F)c(F)c(F)c(F)c1F]

4-(N-(bicycle[2.2.1]heptan-2-ylmethyl)-2-((2,3,4,5, 6-pentafluoro-N-methylphenyl)sulfonamido)acetamido)-2-hydroxybenzoic Acid Derivative 8q hydrogenated on a 0.3 mmol scale via general procedure h (66%): δ$_H$ (400 MHz, d-CDCl$_3$) 0.40-0.61 (m, 1H, CH), 0.85-1.07 (m, 2H, CH$_2$), 1.08-1.27 (m, 3H, CH$_2$, CH), 1.28-1.45 (m, 2H, CH$_2$), 1.72-1.90 (m, 1H, CH), 1.99 (s, 1H, CH$_2$), 2.07 (s, 1H, CH$_2$), 2.94 (s, 3H, CH$_3$), 3.48-3.70 (m, 2H, CH$_2$), 4.00 (s, 2H, CH$_2$), 6.83 (d, J=8.4 Hz, 1H, CH), 6.91 (s, 1H, CH), 7.86 (d, J=8.2 Hz, 1H, CH); δ$_C$ (100 MHz, d-CDCl$_3$): 28.2, 29.4, 34.3, 34.4, 37.7, 38.7, 39.6, 42.6, 48.9, 113.2, 131.5, 131.8, 137.2, 140.4, 142.5, 148.3, 164.4, 166.2, 171.3; HRMS (ES+) calculated for [C$_{24}$H$_{23}$F$_5$N$_2$O$_6$S+H] 562.12. found 563.10; HPLC (I) tR=30.77 min (98.73%), (II) tR=36.21 min (99.12%).

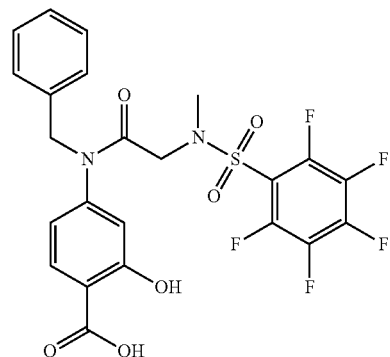 [SMILES: CN(CC(=O)N(Cc1ccccc1)c1ccc(C(=O)O)c(O)c1)S(=O)(=O)c1c(F)c(F)c(F)c(F)c1F]

4-(N-(benzyl-2-((2,3,4,5,6-pentafluoro-N-methylphenyl)sulfonamido)acetamido)-2-hydroxybenzoic Acid Derivative 8s hydrogenated on a 0.3 mmol scale via general procedure h (87%): δ$_H$ (400 MHz, d-CDCl$_3$) 3.10 (s, 3H, CH$_3$), 4.06 (s, 2H, CH$_2$), 4.78 (s, 2H, CH$_2$), 6.55 (d, J=8.6 Hz, 1H, CH), 6.69 (s, 1H, CH), 7.04-7.16 (m, 2H, CH), 7.26-7.32 (m, 3H, CH), 7.89 (d, J=8.4 Hz, 1H, CH); δ$_C$ (100 MHz, d-CDCl$_3$): 29.6, 30.3, 35.9, 50.8, 52.2, 53.2, 111.9, 115.8, 117.1, 119.1, 128.0, 128.4, 128.6, 132.2, 132.6, 135.7, 139.1, 143.5, 146.1, 147.1, 163.1, 166.0, 172.3; HRMS (ES+) calculated for [C$_{23}$H$_{17}$F$_5$N$_2$O$_6$S+H] 544.07. found 545.10; HPLC (I) tR=19.74 min (97.50%), (II) tR=30.90 min (96.37%).

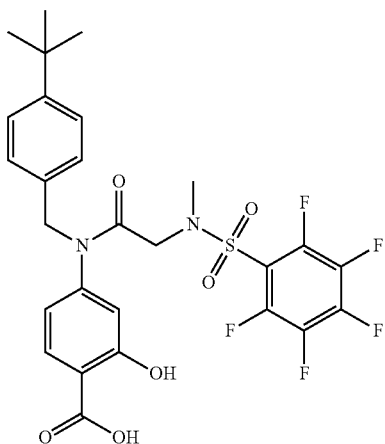 [SMILES: CN(CC(=O)N(Cc1ccc(C(C)(C)C)cc1)c1ccc(C(=O)O)c(O)c1)S(=O)(=O)c1c(F)c(F)c(F)c(F)c1F]

4-(N-(4-tert-butyl)benzyl)-2-((2,3,4,5,6-pentafluoro-N-methylphenyl)sulfonamido)acetamido)-2-hydroxybenzoic Acid Derivative 8w hydrogenated on a 0.4 mmol scale via general procedure h (92%): $\delta_H$ (400 MHz, d-CDCl$_3$) 1.29 (s, 9H, CH$_3$), 3.10 (s, 3H, CH$_3$), 4.08 (s, 2H, CH$_2$), 4.76 (s, 2H, CH$_2$), 6.59 (d, J=8.4 Hz, 1H, CH), 6.72 (s, 1H, CH), 7.01 (d, J=8.1 Hz, 2H, CH), 7.29 (d, J=8.15 Hz, 2H, CH), 7.90 (d, J=8.4 Hz, 1H, CH); $\delta_C$ (100 MHz, d-CDCl$_3$): 31.1, 32.0, 34.3, 35.8, 37.1, 52.1, 52.9, 116.9, 118.8, 125.4, 127.9, 132.50, 150.8, 162.92, 165.9, 172.4; HRMS (ES+) calculated for [C$_{27}$H$_{25}$F$_5$N$_2$O$_6$S+H] 600.14. found 601.10; HPLC (I) tR=23.68 min (98.12%), (II) tR=37.81 min (98.08%).

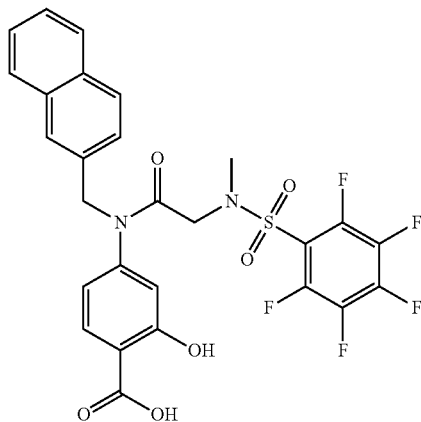 [SMILES: CN(CC(=O)N(Cc1ccc2ccccc2c1)c1ccc(C(=O)O)c(O)c1)S(=O)(=O)c1c(F)c(F)c(F)c(F)c1F]

2-hydroxy-4-(N-(naphthalene-2-ylmethyl)-2-((2,3,4,5,6-pentafluoro-N-methylphenyl)sulfonamide)acetamido)benzoic Acid Derivative 8v hydrogenated on a 0.4 mmol scale via general procedure h (73%): $\delta_H$ (400 MHz, d-CDCl$_3$) 3.10 (s, 3H, CH$_3$), 4.09 (s, 2H, CH$_2$), 4.95 (s, 2H, CH$_2$), 6.54 (d, J=8.4 Hz, 1H, CH), 6.72 (s, 1H, CH), 7.23 (s, 1H, CH), 7.40-7.56 (m, 3H, CH), 7.67-7.94 (m, 4H, CH); $\delta_C$ (100 MHz, d-CDCl$_3$): 20.6, 35.7, 52.1, 53.1, 118.9, 125.8, 126.0, 126.1, 127.5, 127.6, 128.5, 132.5, 132.7, 133.0, 133.1, 162.8, 166.1, 177.5; HRMS (ES+) calculated for [C$_{27}$H$_{19}$F$_5$N$_2$O$_6$S+H] 594.09. found 595.10; HPLC (I) tR=21.64 min (90.45%), (II) tR=34.27 min (88.02%).

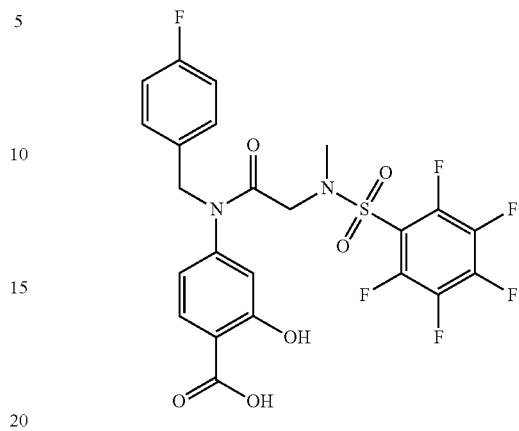

4-(N-(4-fluorobenzyl)-2-((2,3,4,5,6-pentafluoro-N-methylphenyl)sulfonamide)acetamido)-2-hydroxybenzoic Acid Derivative 8t hydrogenated on a 0.15 mmol scale via general procedure h (63%): $\delta_H$ (400 MHz, d-CDCl$_3$) 3.09 (s, 3H, CH$_3$), 4.05 (s, 2H, CH$_2$), 4.75 (s, 2H, CH$_2$), 6.54 (d, J=8.53 Hz, 1H, CH), 6.68 (s, 1H, CH), 6.90-7.03 (m, 2H, CH), 7.03-7.12 (m, 2H, CH), 7.92 (d, J=8.50 Hz, 1H, CH); $\delta_C$ (100 MHz, d-CDCl$_3$): 20.5, 29.6, 35.9, 52.0, 52.2, 52.4, 112.1, 115.5, 115.7, 117.1, 117.6, 119.1, 120.4, 129.6, 130.3, 130.4, 131.7, 132.7, 146.9, 147.0, 161.2, 163.1, 163.6, 165.9, 172.7, 176.5; HRMS (ES+) calculated for [C$_{23}$H$_{16}$F$_6$N$_2$O$_6$S+H] 562.06. found 563.10. HPLC (I) tR=19.99 min (98.87%), (II) tR=31.40 min.

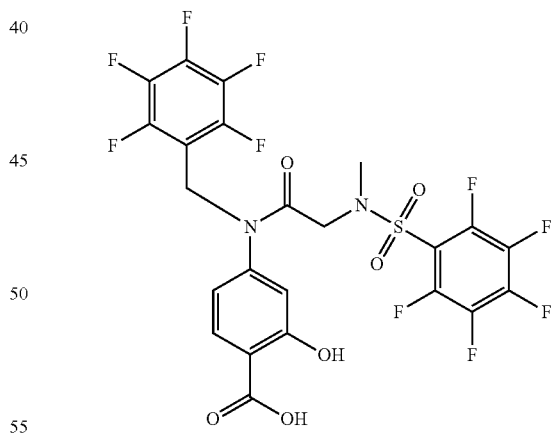

2-hydroxy-4-(2-((2,3,4,5,6-pentafluoro-N-methylphenyl)sulfonamide)-N-((perflurophenyl)methyl)acetamido)benzoic Acid Derivative 8u hydrogenated on a 0.07 mmol scale via general procedure h (89%): $\delta_H$ (400 MHz, d-CDCl$_3$) 3.06 (s, 3H, CH$_3$), 4.01 (s, 2H, CH$_2$), 4.94 (s, 2H, CH$_2$), 6.62 (d, J=8.34 Hz, 1H, CH), 6.73 (s, 1H, CH), 7.95 (d, J=8.52 Hz, 1H, CH); $\delta_C$ (100 MHz, d-CDCl$_3$): 29.6, 30.8, 31.3, 35.8, 40.0, 52.0, 58.3, 61.4, 109.0, 112.9, 115.6, 116.8, 118.4, 125.9, 133.0, 136.1, 136.3, 136.5, 138.5, 138.6, 138.9, 142.5, 143.5, 144.0, 145.0, 146.0, 146.5, 163.1, 165.9, 171.5, 173.4; HRMS (ES+) calculated for [$C_{23}H_{12}F_{10}N_2O_6S$+H] 634.03. found 635.0; HPLC (I) tR=20.88 min (98.71%), (II) tR=33.06 min (98.39%).

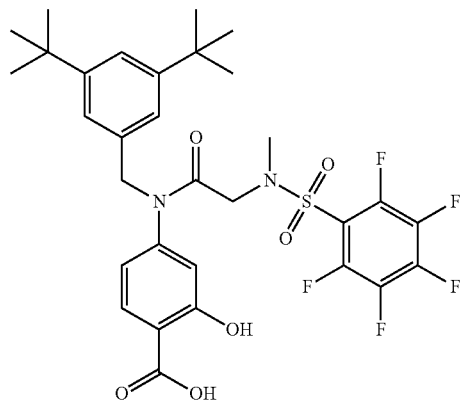 [SMILES: CN(CC(=O)N(Cc1cc(C(C)(C)C)cc(C(C)(C)C)c1)c1ccc(C(=O)O)c(O)c1)S(=O)(=O)c1c(F)c(F)c(F)c(F)c1F]

4-(N-(3,5-di-tert-butyl benzyl)-2-((2, 3,4,5,6-pentafluoro-N-methylphenyl)sulfonamide)acetamido)-2-hydroxybenzoic Acid Derivative 8x hydrogenated on a 0.07 mmol scale via general procedure h (89%): $\delta_H$ (400 MHz, d-CDCl$_3$) 3.06 (s, 3H, CH$_3$), 4.01 (s, 2H, CH$_2$), 4.94 (s, 2H, CH$_2$), 6.62 (d, J=8.34 Hz, 1H, CH), 6.73 (s, 1H, CH), 7.95 (d, J=8.52 Hz, 1H, CH); $\delta_C$(100 MHz, d-CDCl$_3$): 29.6, 30.8, 31.3, 35.8, 40.0, 52.0, 58.3, 61.4, 109.0, 112.9, 115.6, 116.8, 118.4, 125.9, 133.0, 136.1, 136.3, 136.5, 138.5, 138.6, 138.9, 142.5, 143.5, 144.0, 145.0, 146.0, 146.5, 163.1, 165.9, 171.5, 173.4; HRMS (ES+) calculated for [$C_{23}H_{12}F_{10}N_2O_6S$+H] 634.03. found 635.0; HPLC (I) tR=26.48 min (99.42%), (II) tR=43.39 min (98.62%).

Other compounds of the disclosure were synthesized according to Scheme 2:

Scheme 2:

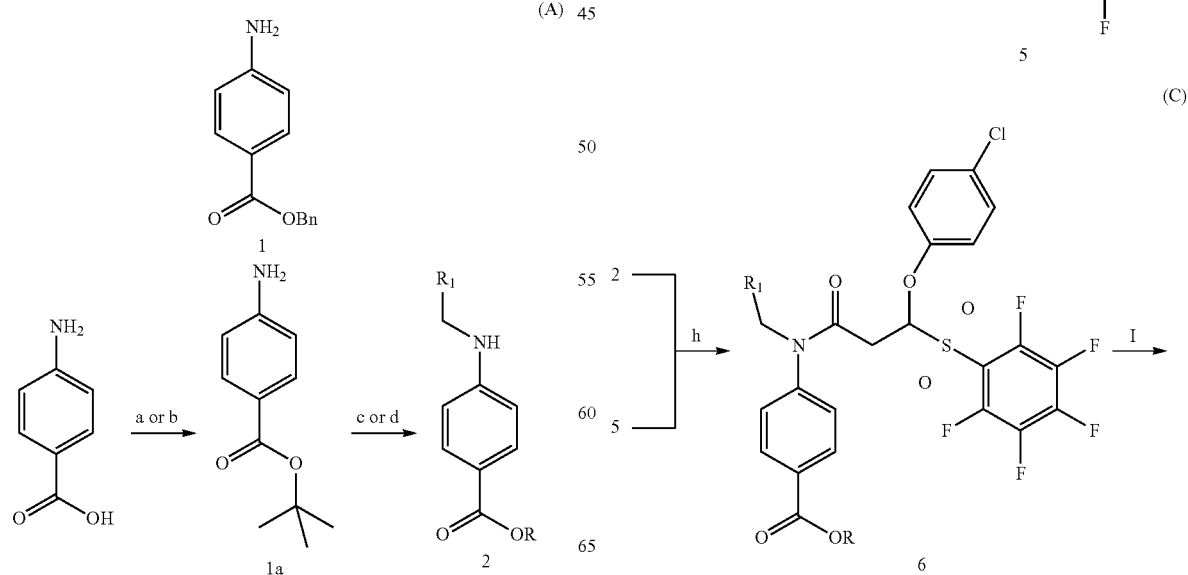

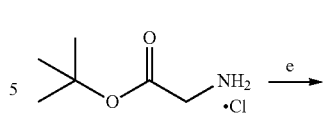

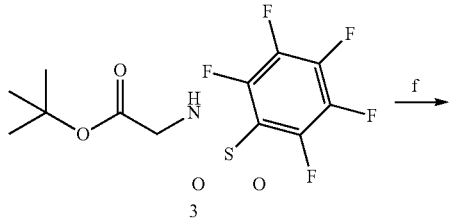

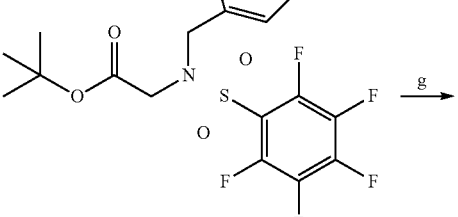

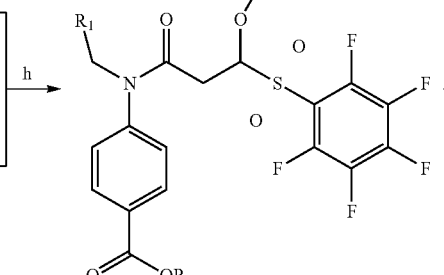

-continued

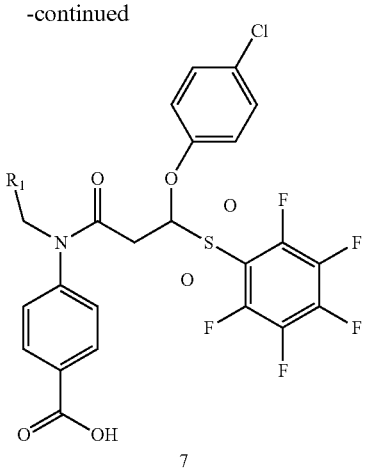

7

(A) a) i) K'OBu, BnBr, DMF, 0° C. ⟶ RT., 1 h;
then K'OBu, BnBr, DMF, 0° C. ⟶ RT, 16 h, 60%;
b) SOCl₂, t-butanol, DCM, 0° C. ⟶ RT, 83%;
c) 1) Aldehyde, AcOH, 3Å Mol. sieves, CH₃OH, 45° C., 2 h;
2) NaCNBH₃, 45° C., 16 h, 56-96%;
d) Aldehyde, 3Å Mol. sieves, CH₂Cl₂, NaOAc, Na(OAc)₃BH, RT, 16 h, 82%;
e) d) C₆F₅SO₂Cl, K₂CO₃, CH₃CN, 16 h, 0° C. ⟶ RT, 60-77%;
f) 1) p-Cl(C₆H₆)BnBr, Cs₂CO₃, DMF, R.T., N₂, 2 h, 70%;
g) CH₂Cl₂:TFA 1:1, RT, 1 h, 90%;
h) PPh₃Cl₂, CHCl₃, 30 min, 100° C. microwave assisted heating, 20-98%;
i) H₂, Pd/C, 1:1 THF/CH₃OH, 3-10 h, RT, 35-95%.
ia) 1:1 TFA/DCM, 30 min, r.t. DMF = N,N-dimethylformamide, TFA = trifluoroacetic acid.

General Procedure a (Dibenzylation of Salicylic Acid).

To a stirred solution of 4-aminosalicylic acid (1.0 eq) in DMF (0.1 M) at 0° C. was added KO'Bu (1.2 eq). After 15 min, benzyl bromide (1.2 eq) was added drop-wise. The suspension was allowed to stir at room temperature for a further 4 h before the reaction vessel was again cooled to 0° C. Once again, KO'Bu (1.2 eq) was added prior to the dropwise addition of benzyl bromide (1.2 eq). The reaction was left to stir overnight before quenching with H₂O. The solution was then repeatedly extracted with ethyl acetate and the organic phases combined. The organics were then washed with H₂O and brine then concentrated, dried over Na₂SO₄ and concentrated in vacuo. The resulting residue was purified using the Biotage Isolera automated column chromatographer with a 4:1 Hexanes/EtOAc gradient under reduced pressure.

General Procedure b (t-Butyl Protection of Salicylic Acid).

4-aminobenzoic acid was suspended in SOCl₂ (2.0 eq.) at 25° C. The suspension was refluxed for 2 h. SOCl₂ was removed under reduced pressure, the last traces by azeotrope with CHCl₃ (×3). The resulting acid chloride was dissolved in CH₂Cl₂ and a solution of t-butanol in CH₂Cl₂ was added to the stirred solution which was cooled to 0° C. A solid white precipitate was formed—the hydrochloride salt was quenched with 1.0M KOH and extracted with EtOAC (×4).

General Procedure c (Reductive Amination Using Sodium Cyanoborohydride).

To a solution of protected 4-amino salicylic acid 1/1a (1.0 eq) and acetic acid (1.5 eq) stirred in anhydrous CH₃OH (0.1 M) with 3 Å mol. sieves was added the aldehyde (1.0 eq). The solution was heated to 45° C. for 3 hr and then allowed to cool to rt. Next, NaCNBH₃ (1.3 equiv) was added portion-wise and the reaction was allowed to stir at rt overnight. The reaction was diluted with CH₂Cl₂, filtered and concentrated in vacuo. The concentrate was purified using the Biotage Isolera automated column chromatographer using a gradient of Hexanes/EtOAc to furnish secondary anilines 2.

General Procedure d (Reductive Amination Using Sodium Triacetoxyborohydride).

To a solution of protected 4-amino salicylic acid 1/1a (1.2 eq) and acetic acid (1.2 eq) stirred in anhydrous dichloroethane (0.1 M) with 3 Å mol. sieves was added the aldehyde (1.0 eq). The solution was then stirred at rt for 5 min after which Na(OAc)₃BH (1.5 eq) was added and left to stir at rt overnight. The reaction was diluted with CH₂Cl₂, filtered and concentrated in vacuo. The concentrate was purified using the Biotage Isolera automated column chromatographer using a gradient of Hexanes/EtOAc to furnish secondary aniline derivatives 2.

General Procedure e (Sulfonylation of Glycine and Sarcosine t-Butyl Ester).

A solution of amino acid t-butyl ester (1 eq) and K₂CO₃ (1.1 eq) were dissolved in anhydrous acetonitrile and cooled to 0° C. before sulfonyl chloride (1 eq) was added. The resultant solution was allowed to stir overnight at rt. The reaction was concentrated in vacuo and residue was dissolved in CH₂Cl₂. The organics were combined and then washed sequentially with 0.1 M HCl, saturated NaHCO₃ and brine. The organics were then dried over Na₂SO₄ and concentrated in vacuo to furnish derivatives 3 with no further purification.

General Procedure f (Alkylation of Sulfonamide).

A solution of 3 (1 eq) and Cs₂CO₃ (1.3 eq) were dissolved in anhydrous DMF followed by the addition of p-ClBnBr (1 eq). The resultant solution was allowed to stir for 2 h at r.t. The reaction was quenched with H₂O and then repeatedly extracted with ethyl acetate. The organic phases were combined and washed with H₂O, brine, dried over Na₂SO₄ and concentrated in vacuo. The resulting residue was purified using the Biotage Isolera automated column chromatographer with a 2:1 Hexanes/EtOAc gradient under reduced pressure to provide compound 4.

General Procedure g (t-Butyl Ester Deprotection).

A solution of amino acid t-butyl ester (1 eq) was dissolved in TFA and immediately diluted with CH₂Cl₂ in a 1:1 mixture (0.1 M) solution. The resultant solution was allowed to stir for 1 h and then co-evaporated with CH₃OH (3×) and CHCl₃ (3×). The resultant residue was carried forward with no purification to yield compounds 5.

General Procedure h (PPh₃Cl₂ Peptide Coupling).

To a stirred solution of carboxylic acid (5) (1.1 eq) in CHCl₃ (0.1 M) was added PPh₃Cl₂ (2.5 eq). The reaction was allowed to stir 5 min at rt or until complete dissolvation, followed by the drop-wise addition of the secondary aniline 2 (1.0 eq). The reaction mixture was then heated in a microwave at 100° C. for 30 min. The reaction mixture was allowed to cool to rt followed by sequential washing with saturated NaHCO₃ and brine. The organic layers were then dried over Na₂SO₄ and concentrated in vacuo. The concentrate was absorbed directly onto silica for column chromatography purification using a gradient of hexanes and EtOAc to furnish derivatives 6.

General Procedure i (Hydrogenolysis of the Benzyl Ester and Benzyl Ether).

The benzyl protected salicylic acid, 6 (1 eq) were dissolved in a stirred solution of CH₃OH/THF (1:2, 0.1 M). The solution was thoroughly degassed before the careful addition of 10% Pd/C (10 mg/mmol). H₂ gas was bubbled through the solvent for 5 min before the solution was put under an atmosphere of H₂ gas and stirred continuously for 2-5 h, monitoring completion of reaction via TLC. The H₂ gas was evacuated and the reaction filtered through celite to remove Pd catalyst and concentrated in vacuo. The resulting residue was adsorbed onto silica and columned using a Biotage Isolera in a gradient of $CH_2Cl_2$, $CH_3OH$ and 1% acetic acid to provide final molecule series 7.

General Procedure i (Acid Deprotection of t-Butyl Functional Groups).

The t-butyl protected salicylic acid, was dissolved with 1:1 ration of TFA/DCM and stirred for 30 min. The crude solution was concentrated down in vacuo. The resulting residue was adsorbed onto silica and columned using a Biotage Isolera in a gradient of $CH_2Cl_2$, $CH_3OH$ and 1% acetic acid to provide final molecule series 7.

Intermediate Characterization Data

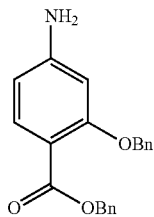 [SMILES: Nc1ccc(C(=O)OCc2ccccc2)c(OCc2ccccc2)c1]

Benzyl 4-amino-2-(benzyloxy)benzoate (Scheme 2-1)

Compound 1 was synthesized according to general procedure a, yielding the final product as an orange solid (47%): $\delta_H$ (400 MHz, d-$CDCl_3$) 5.07 (s, 2H, $CH_2$), 5.21 (s, 2H, $CH_2$), 5.99 (br s, 2H, $NH_2$), 6.18 (dd, J=8.6 and 1.8 Hz, 1H, CH)), 6.32 (d, J=1.7 Hz, 1H, CH), 7.28-7.38 (8H, m, CH), 7.47 (d, J=7.2 Hz, 2H, CH), 7.60 (d, J=8.6 Hz, 1H, CH); $\delta_C$ (400 MHz, $CDCl_3$) 65.8, 70.2, 99.1, 106.7, 109.0, 126.8, 127.5, 127.7, 127.9, 128.3, 128.4, 134.3, 136.6, 136.7, 152.2, 160.7, 165.7; LRMS (ESI+) calculated for $C_{21}H_{19}NO_3$ $[M+H]^+$ 333.2. found 333.2.

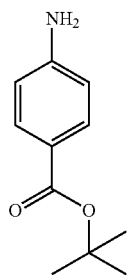

Tert-butyl 4-aminobenzoate (1a)

Derivative 1a synthesized according to general procedure b on (83%): $^1$H NMR (400 MHz, DMSO-$d_6$) δ 1.06-1.19 (m, 7H), 1.39 (s, 1H), 1.46 (s, 16H), 1.52 (d, J=3.6 Hz, 3H), 1.88 (s, 1H), 1.96 (s, 6H), 4.00 (q, J=7.1 Hz, 4H), 5.82 (d, J=15.3 Hz, 4H), 6.47-6.55 (m, 4H), 7.50-7.59 (m, 4H), 7.79-7.98 (m, 2H). $^{13}$C NMR (101 MHz, DMSO-$d_6$) δ 28.16, 28.30, 79.14, 112.80, 117.95, 119.36, 119.66, 129.89, 131.18, 153.37, 165.58. LRMS (ESI+) calculated for $C_{11}H_{16}NO_2$ $[M+H]^+$ 194.11. found 194.15.

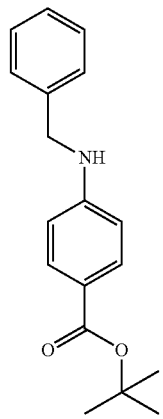 [SMILES: CC(C)(C)OC(=O)c1ccc(NCc2ccccc2)cc1]

Tert-butyl 4-(benzylamino)benzoate (2a)

Derivative 2a synthesized according to general procedure c on (67%): $^1$H NMR (400 MHz, Chloroform-d) δ 1.62 (s, 9H), 4.37 (d, J=5.3 Hz, 2H), 4.76 (t, J=5.7 Hz, 1H), 6.54-6.63 (m, 2H), 7.26-7.41 (m, 5H), 7.84-7.94 (m, 2H). $^{13}$C NMR (101 MHz, Chloroform-d) δ 28.27, 47.41, 79.74, 111.50, 120.25, 127.19, 127.26, 128.61, 131.25, 138.56, 151.50, 166.14. LRMS (ESI+) calculated for $C_{18}H_{22}NO_2$ $[M+H]^+$ 284.15. found 284.16.

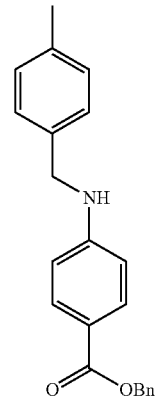 [SMILES: Cc1ccc(CNc2ccc(C(=O)OCc3ccccc3)cc2)cc1]

Benzyl 4-((4-methylbenzyl)amino)benzoate (2b)

Derivative 2b synthesized according to general procedure c on (80%): $^1$H NMR (400 MHz, Chloroform-d) δ 1.50-1.57 (m, 1H), 2.36 (s, 3H), 4.33 (d, J=4.7 Hz, 2H), 4.57 (d, J=5.4 Hz, 1H), 5.30 (d, J=14.9 Hz, 6H), 6.55-6.63 (m, 2H), 7.17 (d, J=7.9 Hz, 2H), 7.24 (d, J=7.9 Hz, 2H), 7.29-7.43 (m, 3H), 7.45 (dt, J=6.1, 1.6 Hz, 2H), 7.88-7.97 (m, 2H). $^{13}$C NMR (101 MHz, Chloroform-d) δ 20.97, 47.24, 53.36, 65.83, 111.51, 118.22, 127.26, 127.84, 128.37, 129.31, 131.58, 135.17, 136.58, 137.06, 151.83, 166.50. LRMS (ESI+) calculated for $C_{22}H_{22}NO_2$ $[M+H]^+$ 332.15. found 332.17.

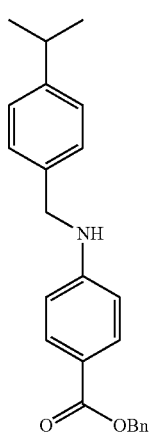 [SMILES: CC(C)c1ccc(CNc2ccc(C(=O)OCc3ccccc3)cc2)cc1]

Benzyl 4-((4-isopropylbenzyl)amino)benzoate (2c)

Derivative 2c synthesized according to general procedure c on (76%): $^1$H NMR (400 MHz, Chloroform-d) δ 1.26 (d, J=7.0 Hz, 6H), 2.91 (hept, J=6.9 Hz, 1H), 4.34 (s, 2H), 4.53 (s, 1H), 5.32 (s, 2H), 6.59 (dd, J=8.5, 1.2 Hz, 2H), 7.22 (d, J=7.9 Hz, 2H), 7.24-7.40 (m, 4H), 7.44 (d, J=7.9 Hz, 2H), 7.88-7.95 (m, 2H). $^{13}$C NMR (101 MHz, Chloroform-d) δ 23.87, 33.68, 47.31, 65.82, 111.48, 118.30, 126.69, 127.39, 127.81, 127.84, 128.35, 131.59, 135.47, 136.56, 148.18, 151.76. LRMS (ESI+) calculated for $C_{24}H_{26}NO_2$ $[M+H]^+$ 360.18. found 360.18.

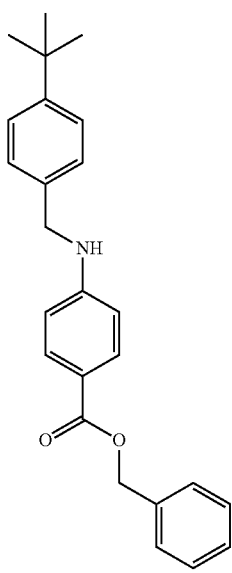 [SMILES: CC(C)(C)c1ccc(CNc2ccc(C(=O)OCc3ccccc3)cc2)cc1]

Benzyl 4-((4-(tert-butyl)benzyl)amino)benzoate (2d)

Derivative 2d synthesized according to general procedure c: $^1$H NMR (400 MHz, Chloroform-d) δ 1.34 (s, 9H), 4.35 (s, 2H), 5.33 (s, 2H), 6.56-6.63 (m, 2H), 7.23-7.48 (m, 9H), 7.89-7.96 (m, 2H). $^{13}$C NMR (101 MHz, Chloroform-d) δ 31.23, 34.41, 47.21, 65.82, 111.49, 118.29, 125.56, 127.13, 127.82, 127.85, 128.36, 131.60, 135.13, 151.79, 166.46. LRMS (ESI+) calculated for $C_{25}H_{28}NO_2$ $[M+H]^+$ 374.20. found 374.22.

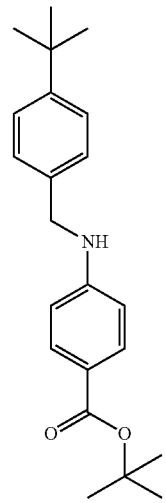 [SMILES: CC(C)(C)OC(=O)c1ccc(NCc2ccc(C(C)(C)C)cc2)cc1]

Tert-butyl 4-((4-(tert-butyl)benzyl)amino)benzoate (2d)

Derivative 2d synthesized according to general procedure c on (71%): $^1$H NMR (400 MHz, Methanol-d$_4$) δ 1.29 (s, 5H), 1.54 (s, 5H), 4.32 (s, 1H), 6.56 (d, J=8.7 Hz, 1H), 7.26 (d, J=8.1 Hz, 1H), 7.35 (d, J=8.3 Hz, 1H), 7.62-7.70 (m, 1H). LRMS (ESI+) calculated for $C_{25}H_{28}NO_2$ $[M+H]^+$ 331.22. found 331.24.

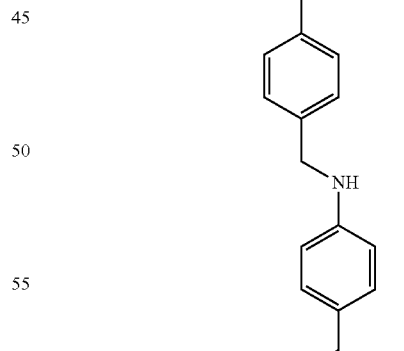

Benzyl 4-((4-(trifluoromethyl)benzyl)amino)benzoate (2e)

Derivative 2e synthesized according to general procedure c on (71%): LRMS (ESI+) calculated for $C_{22}H_{19}F_3NO_2$ $[M+H]^+$ 386.13. found 386.15.

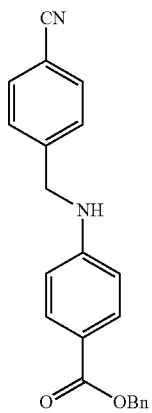 [SMILES: N#Cc1ccc(CNc2ccc(C(=O)OCc3ccccc3)cc2)cc1]

Benzyl 4-((4-cyanobenzyl)amino)benzoate (2f)

Derivative 2f synthesized according to general procedure d on (60%): $^1$H NMR (400 MHz, Chloroform-d) δ 1.24 (t, J=7.2 Hz, 1H), 2.02 (s, 1H), 4.10 (q, J=7.1 Hz, 1H), 4.41 (d, J=4.4 Hz, 2H), 4.72 (s, 1H), 5.12 (t, J=6.0 Hz, 1H), 5.27 (s, 2H), 6.52 (d, J=8.4 Hz, 2H), 7.23-7.46 (m, 8H), 7.54 (dd, J=8.1, 5.6 Hz, 3H), 7.85 (d, J=8.4 Hz, 2H). $^{13}$C NMR (101 MHz, Chloroform-d) δ 14.07, 46.77, 63.75, 65.90, 110.75, 111.65, 118.61 (d, J=19.5 Hz), 126.87, 127.50, 127.85 (d, J=15.2 Hz), 128.41, 131.58, 132.02, 132.33, 136.38, 144.38, 151.46, 166.51. LRMS (ESI+) calculated for $C_{22}H_{19}N_2O_2$ [M+H]$^+$ 343.13. found 343.14.

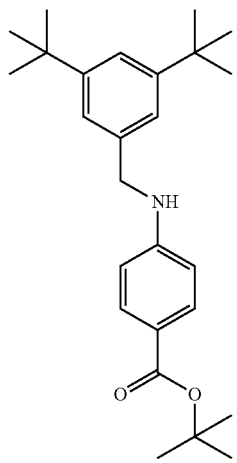

Tert-butyl 4-((3,5-di-tert-butylbenzyl)amino)benzoate (2g)

Derivative 2g synthesized according to general procedure d on (85%): $^1$H NMR (400 MHz, Chloroform-d) δ 1.47 (s, 18H), 1.68 (s, 9H), 4.43 (d, J=5.1 Hz, 2H), 4.67 (t, J=5.3 Hz, 1H), 6.66-6.73 (m, 2H), 7.32 (d, J=1.8 Hz, 2H), 7.50 (t, J=1.8 Hz, 1H), 7.93-8.00 (m, 2H). $^{13}$C NMR (101 MHz, Chloroform-d) δ 28.34, 31.49, 34.82, 48.43, 79.64, 111.45, 120.27, 121.47, 121.90, 131.32, 137.58, 151.18, 151.74, 166.15. LRMS (ESI+) calculated for $C_{26}H_{38}NO_2$ [M+H]$^+$ 396.28. found 396.30.

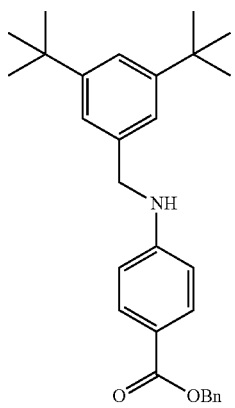 [SMILES: CC(C)(C)c1cc(CNc2ccc(C(=O)OCc3ccccc3)cc2)cc(C(C)(C)C)c1]

Benzyl 4-((3,5-di-tert-butylbenzyl)amino)benzoate (2g)

Derivative 2g synthesized according to general procedure d on (60%): $^1$H NMR (400 MHz, Chloroform-d) δ 1.26 (d, J=7.0 Hz, 6H), 2.91 (hept, J=6.9 Hz, 1H), 4.34 (s, 2H), 5.32 (s, 2H), 6.59 (dd, J=8.5, 1.2 Hz, 2H), 7.22 (d, J=7.9 Hz, 2H), 7.24-7.40 (m, 4H), 7.44 (d, J=7.9 Hz, 2H), 7.88-7.95 (m, 2H). $^{13}$C NMR (101 MHz, Chloroform-d) δ 23.87, 33.68, 47.31, 65.82, 111.48, 118.30, 126.69, 127.39, 127.81, 127.84, 128.35, 131.59, 135.47, 136.56, 148.18, 151.76. LRMS (ESI+) calculated for $C_{29}H_{36}NO_2$ [M+H]$^+$ 430.26. found 430.28.

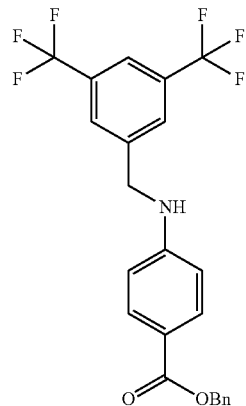 [SMILES: O=C(OCc1ccccc1)c1ccc(NCc2cc(C(F)(F)F)cc(C(F)(F)F)c2)cc1]

Benzyl 4-((3,5-bis(trifluoromethyl)benzyl)amino)benzoate (2h)

Derivative 2h synthesized according to general procedure c on (41%): $^1$H NMR (400 MHz, Chloroform-d) δ 4.53 (d, J=5.8 Hz, 2H), 4.71 (t, J=5.9 Hz, 1H), 5.31 (s, 2H), 6.52-6.61 (m, 2H), 7.27-7.39 (m, 3H), 7.39-7.46 (m, 2H), 7.80 (s, 3H), 7.87-7.96 (m, 2H). $^{13}$C NMR (101 MHz, Chloroform-d) δ 46.80, 65.99, 111.75, 119.52, 121.39, 127.01, 127.86, 127.89, 128.37, 131.66, 132.13, 136.35, 141.29, 150.87, 166.27. LRMS (ESI+) calculated for $C_{23}H_{18}F_6NO_2$ [M+H]$^+$ 454.12. found 454.15.

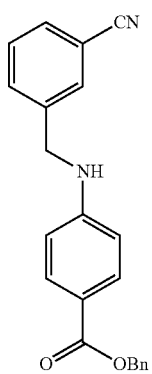 [SMILES: N#Cc1cccc(CNc2ccc(C(=O)OCc3ccccc3)cc2)c1]

Benzyl 4-((3-cyanobenzyl)amino)benzoate (2i)

Derivative 2i synthesized according to general procedure d on (83%): $^1$H NMR (400 MHz, Chloroform-d) δ 1.24 (q, J=7.6, 7.1 Hz, 1H), 3.49 (d, J=7.9 Hz, 1H), 4.38 (d, J=5.7 Hz, 3H), 4.67 (d, J=2.9 Hz, 3H), 5.14 (d, J=4.9 Hz, 2H), 5.26 (s, 3H), 6.49-6.57 (m, 3H), 7.23-7.39 (m, 5H), 7.34-7.43 (m, 5H), 7.44-7.63 (m, 11H), 7.80-7.88 (m, 3H). $^{13}$C NMR (101 MHz, Chloroform-d) δ 46.40, 63.43, 65.96, 111.68, 111.95, 112.33, 118.40, 127.78, 127.94, 128.42, 129.06, 129.42, 129.96, 130.36, 130.76, 130.89, 130.99, 131.49, 131.60, 136.33, 140.30, 142.65, 151.50, 166.67. LRMS (ESI+) calculated for $C_{22}H_{19}N_2O_2$ [M+H]$^+$ 343.13. found 343.16.

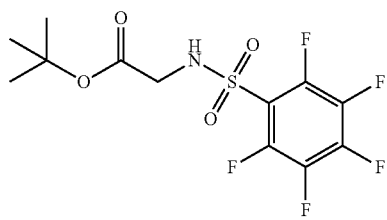 [SMILES: CC(C)(C)OC(=O)CNS(=O)(=O)c1c(F)c(F)c(F)c(F)c1F]

tert-butyl ((perfluorophenyl)sulfonyl)glycinate (3)

Derivative 3 synthesized using general procedure e (71%): δ$_H$ (400 MHz, CDCl$_3$) 1.40 (s, 9H, COO(CH$_3$)$_3$), 3.93 (s, 2H, CH$_2$), 5.54 (s, 1H, NH); δ$_C$ (400 MHz, CDCl$_3$) 27.5, 45.1, 82.8, 115.6, 136.5, 144.8, 145.9, 167.0; LRMS (ESI+) calculated for $C_{12}H_{12}F_5NO_4S$ [M+H]$^+$ 361.0. found 362.1.

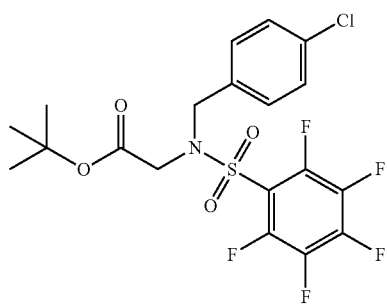 [SMILES: CC(C)(C)OC(=O)CN(Cc1ccc(Cl)cc1)S(=O)(=O)c1c(F)c(F)c(F)c(F)c1F]

tert-butyl N-(4-chlorobenzyl)-N-((perfluorophenyl)sulfonyl)glycinate (4)

Derivative 4 synthesized using general procedure f (71%): δ$_H$ (400 MHz, CDCl$_3$) 1.37 (s, 9H, (CH$_3$)$_3$), 3.93 (s, 2H, CH$_2$), 4.57 (s, 2H, CH$_2$), 7.24 (d, J=8.5 Hz, 2H, CH), 7.33 (d, J=8.5 Hz, 2H, CH); δ$_C$ (400 MHz, CDCl$_3$) 27.5, 52.5, 53.0, 81.8, 112.6, 126.5, 130.1, 132.4, 134.3, 136.5, 144.8, 145.9, 167.0; LRMS (ESI+) calculated for $C_{19}H_{17}F_5ClNO_4S$ [M+H]$^+$ 485.0. found 486.1.

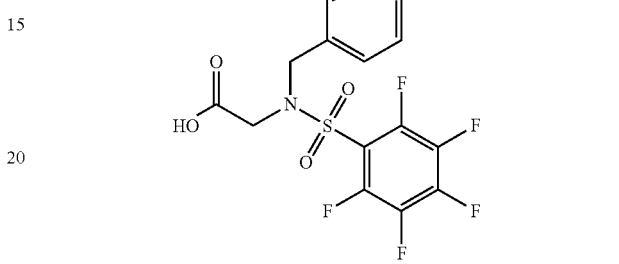

N-(4-chlorobenzyl)-N-((perfluorophenyl)sulfonyl) glycine (5)

Derivative 5 synthesized using general procedure g (92%): δ$_H$ (400 MHz, CDCl$_3$) 4.13 (s, 2H, CH$_2$), 4.58 (s, 2H, CH$_2$), 7.25 (d, J=8.2 Hz, 2H, CH), 7.35 (d, J=8.2 Hz, 2H, CH); δ$_C$ (400 MHz, CDCl$_3$) 52.8, 54.2, 112.6, 126.5, 130.1, 132.4, 134.3, 136.5, 144.8, 145.9, 172.0; LRMS (ESI+) calculated for $C_{15}H_9F_5ClNO_4S$ [M+H]$^+$ 428.9. found 429.9.

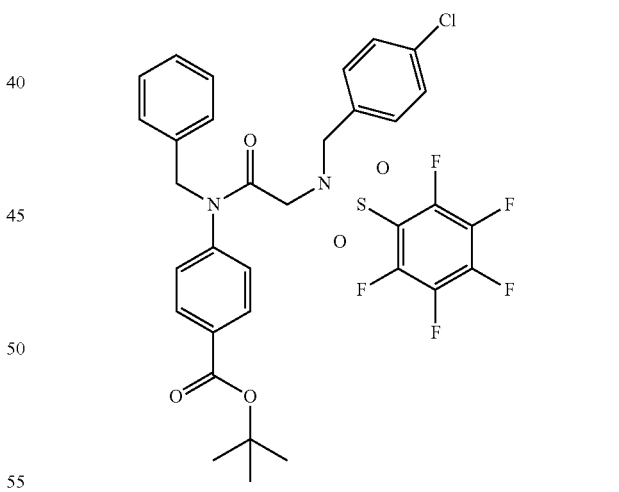

tert-butyl 4-(N-benzyl-2-((N-(4-chlorobenzyl)-2,3,4,5,6-pentafluorophenyl)sulfonamido)acetamido)benzoate (6a)

Derivative 6a synthesized using general procedure h (61%): $^1$H NMR (400 MHz, Chloroform-d) δ 1.25 (s, 3H), 1.56 (s, 27H), 2.04 (s, 1H), 3.72 (s, 3H), 4.65 (s, 4H), 4.72 (s, 6H), 6.79 (d, J=8.0 Hz, 6H), 7.02 (dd, J=6.5, 2.9 Hz, 6H), 7.18 (d, J=8.4 Hz, 6H), 7.23-7.31 (m, 16H), 7.88 (d, J=8.1 Hz, 6H). $^{13}$C NMR (101 MHz, Chloroform-d) δ 27.93, 47.57, 50.51, 53.13, 81.66, 127.67, 127.85, 128.45, 128.57, 128.93, 129.89, 131.07, 132.72, 135.74, 143.14, 164.22, 165.62. LRMS (ESI+) calculated for C$_{33}$H$_{29}$F$_5$ClN$_2$O$_5$S [M+H]$^+$ 695.14. found 695.16.

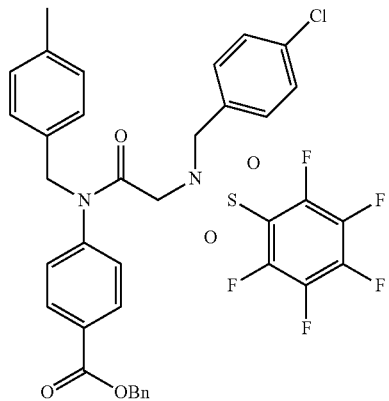

Benzyl 4-(2-((N-(4-chlorobenzyl)-2,3,4,5,6-pentafluorophenyl)sulfonamido)-N-(4-methylbenzyl)acetamido)benzoate (6b)

Derivative 6b synthesized using general procedure h (68%): $^1$H NMR (400 MHz, Chloroform-d) δ 1.27 (t, J=7.1 Hz, 2H), 2.05 (s, 1H), 2.33 (s, 5H), 3.73 (d, J=8.3 Hz, 2H), 4.13 (q, J=7.1 Hz, 1H), 4.68 (d, J=12.0 Hz, 5H), 5.34 (s, 3H), 6.83 (d, J=8.1 Hz, 3H), 6.91 (d, J=7.8 Hz, 3H), 7.08 (d, J=7.8 Hz, 3H), 7.16-7.23 (m, 3H), 7.23-7.47 (m, 11H), 7.98 (d, J=8.2 Hz, 3H). $^{13}$C NMR (101 MHz, Chloroform-d) δ 20.98, 47.62, 50.54, 52.87, 66.97, 127.97, 128.16, 128.31, 128.51, 128.55, 128.94, 129.14, 129.91, 130.46, 131.34, 132.66, 132.76, 134.25, 135.46, 137.66, 143.77, 164.96, 165.49. LRMS (ESI+) calculated for C$_{37}$H$_{29}$ClF$_5$N$_2$O$_5$S [M+H]$^+$ 743.13. found 743.15.

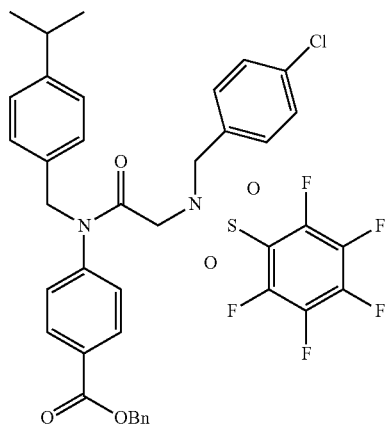

Benzyl-4-(2-((N-(4-chlorobenzyl)-2,3,4,5,6-pentafluorophenyl)sulfonamido)-N-(4-isopropylbenzyl)acetamido)benzoate (6c)

Derivative 6c synthesized using general procedure h (55%): $^1$H NMR (400 MHz, Chloroform-d) δ 0.88 (dt, J=11.6, 7.3 Hz, 1H), 1.25 (d, J=6.9 Hz, 12H), 2.90 (p, J=6.9 Hz, 2H), 3.73 (s, 2H), 4.68 (d, J=13.2 Hz, 6H), 5.35 (s, 4H), 6.82 (d, J=8.1 Hz, 3H), 6.95 (d, J=7.9 Hz, 3H), 7.11-7.21 (m, 7H), 7.26 (d, J=3.1 Hz, 4H), 7.29-7.47 (m, 9H), 7.98 (d, J=8.1 Hz, 3H). $^{13}$C NMR (101 MHz, Chloroform-d) δ 23.78, 33.65, 47.61, 50.50, 52.93, 66.99, 126.51, 127.95, 128.17, 128.32, 128.52, 128.56, 128.94, 129.93, 130.46, 131.34, 132.69, 132.97, 135.45, 143.87, 148.66, 164.99, 165.47. LRMS (ESI+) calculated for C$_{39}$H$_{33}$ClF$_5$N$_2$O$_5$S [M+H]$^+$ 771.16. found 771.17.

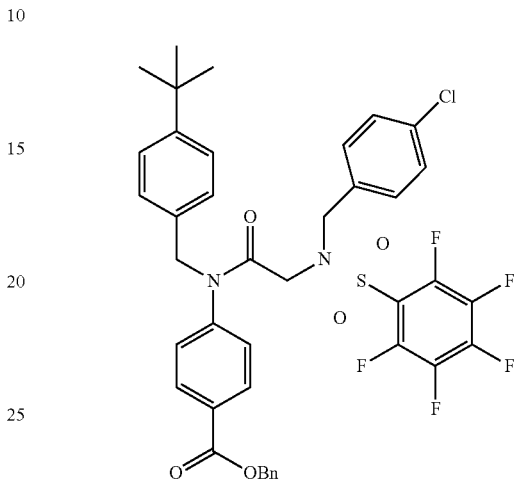

Benzyl-4-(N-(4-(tert-butyl)benzyl)-2-((N-(4-chlorobenzyl)-2,3,4,5,6-pentafluorophenyl)sulfonamido) acetamido)benzoate (6d)

Derivative 6d synthesized using general procedure h (71%): $^1$H NMR (400 MHz, Chloroform-d) δ 1.31 (d, J=1.3 Hz, 10H), 3.72 (s, 1H), 4.67 (d, J=13.0 Hz, 4H), 5.34 (s, 2H), 6.82 (d, J=8.0 Hz, 2H), 6.95 (d, J=7.9 Hz, 2H), 7.18 (d, J=8.0 Hz, 3H), 7.24-7.37 (m, 7H), 7.37-7.42 (m, 4H), 7.44 (d, J=1.9 Hz, 1H), 7.98 (d, J=8.1 Hz, 2H). $^{13}$C NMR (101 MHz, Chloroform-d) δ 31.14, 34.41, 47.59, 50.48, 52.85, 67.00, 125.35, 127.93, 128.17, 128.24, 128.33, 128.52, 128.94, 129.93, 131.35, 132.57, 132.66, 134.27, 135.42, 143.90, 165.00, 165.45. LRMS (ESI+) calculated for C$_{40}$H$_{35}$ClF$_5$N$_2$O$_5$S [M+H]$^+$ 785.18. found 785.21.

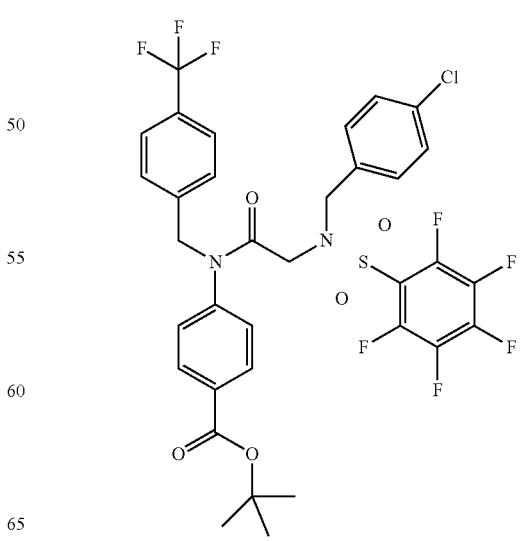

tert-butyl-4-(2-((N-(4-chlorobenzyl)-2,3,4,5,6-pentafluorophenyl)sulfonamido)-N-(4-(trifluoromethyl)benzyl)acetamido)benzoate (6e)

Derivative 6e synthesized using general procedure h (77%): $^1$H NMR (400 MHz, Chloroform-d) δ 1.57 (s, 5H), 3.75 (s, 1H), 4.63 (s, 1H), 4.77 (s, 1H), 6.83 (d, J=8.1 Hz, 1H), 7.18 (dd, J=8.2, 4.0 Hz, 2H), 7.27 (d, J=9.0 Hz, 2H), 7.55 (d, J=8.0 Hz, 1H), 7.92 (d, J=8.2 Hz, 1H). $^{13}$C NMR (101 MHz, Chloroform-d) δ 27.92, 47.60, 50.51, 52.76, 77.06, 81.81, 125.44, 125.48, 127.50, 128.78, 128.97, 129.84, 131.31, 132.59, 132.68, 134.36, 139.71, 142.91, 166.03. LRMS (ESI+) calculated for $C_{34}H_{28}ClF_8N_2O_5S$ [M+H]$^+$ 763.12. found 763.15.

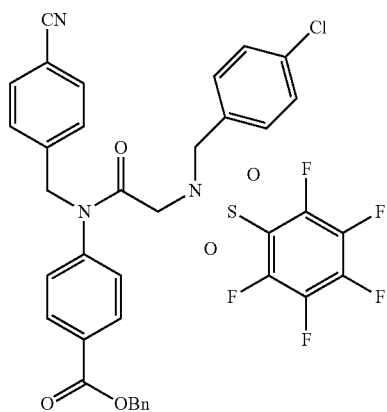

Benzyl-4-(2-((N-(4-chlorobenzyl)-2,3,4,5,6-pentafluorophenyl)sulfonamido)-N-(4-cyanobenzyl)acetamido)benzoate (6f)

Derivative 6f synthesized using general procedure h (60%): $^1$H NMR (400 MHz, Chloroform-d) δ 1.25 (t, J=7.1 Hz, 1H), 2.04 (s, 1H), 3.77 (s, 1H), 4.62 (s, 2H), 4.78 (s, 2H), 5.34 (s, 2H), 6.86 (d, J=8.1 Hz, 2H), 7.17 (dd, J=8.4, 2.6 Hz, 4H), 7.24-7.30 (m, 2H), 7.30-7.45 (m, 5H), 7.55-7.62 (m, 2H), 7.97-8.05 (m, 2H). $^{13}$C NMR (101 MHz, Chloroform-d) δ 47.67, 50.55, 52.85, 67.10, 127.65, 128.19, 128.37, 128.53, 128.99, 129.09, 129.82, 130.92, 131.67, 132.33, 132.51, 134.40, 135.32, 140.93, 143.34, 164.71, 166.16. LRMS (ESI+) calculated for $C_{37}H_{26}ClF_5N_3O_5S$ [M+H]$^+$ 754.11. found 754.15.

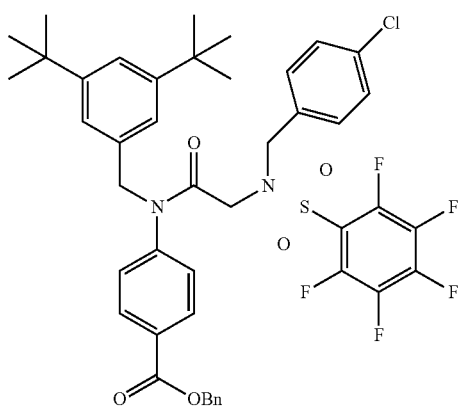

Benzyl-4-(2-((N-(4-chlorobenzyl)-2,3,4,5,6-pentafluorophenyl)sulfonamido)-N-(3,5-di-tert-butylbenzyl)acetamido)benzoate (6g)

Derivative 6g synthesized using general procedure h (84%): $^1$H NMR (400 MHz, Chloroform-d) δ 0.82-0.93 (m, 1H), 1.24-1.37 (m, 25H), 3.71 (s, 2H), 4.62 (s, 2H), 4.74 (s, 3H), 5.35 (s, 3H), 6.75 (d, J=8.0 Hz, 3H), 6.85 (s, 3H), 7.15 (d, J=8.1 Hz, 3H), 7.24 (d, J=8.1 Hz, 4H), 7.29-7.46 (m, 10H), 7.94 (d, J=8.0 Hz, 3H). $^{13}$C NMR (101 MHz, Chloroform-d) δ 31.18, 34.56, 47.70, 50.27, 53.34, 66.94, 121.51, 123.13, 128.05, 128.09, 128.28, 128.51, 128.92, 129.97, 131.11, 132.59, 134.31, 134.47, 135.47, 150.98, 165.27. LRMS (ESI+) calculated for $C_{44}H_{43}ClF_5N_2O_5S$ [M+H]$^+$ 841.24. found 841.27.

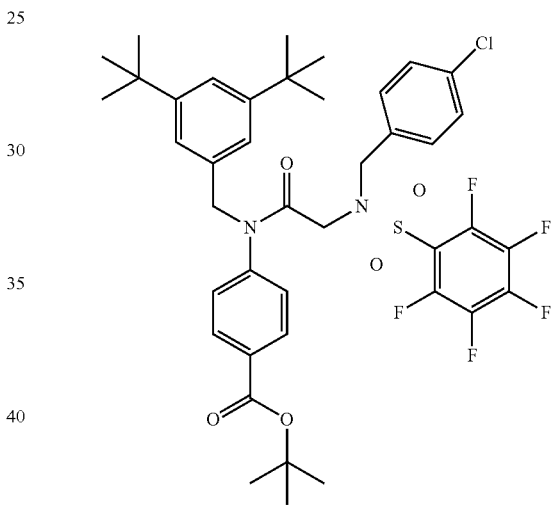

tert-butyl 4-(2-((N-(4-chlorobenzyl)-2,3,4,5,6-pentafluorophenyl)sulfonamido)-N-(3, 5-di-tert-butylbenzyl)acetamido)benzoate (6g)

$^1$H NMR (400 MHz, Chloroform-d) δ $^1$H NMR (400 MHz, Chloroform-d) δ 1.24 (s, 18H), 1.56 (s, 9H), 3.52-3.87 (m, 2H), 4.61 (s, 2H), 4.74 (d, J=12.3 Hz, 2H), 6.71 (d, J=8.0 Hz, 2H), 6.81-6.87 (m, 2H), 7.14 (d, J=8.5 Hz, 2H), 7.20-7.34 (m, 3H), 7.84 (d, J=8.0 Hz, 2H). $^{13}$C NMR (101 MHz, Chloroform-d) δ 27.94, 31.16, 34.55, 47.68, 50.26, 53.34, 81.60, 121.45, 123.10, 127.83, 128.91, 129.97, 130.81, 132.22, 132.62, 134.28, 134.55, 150.92, 164.26, 165.33. LRMS (ESI+) calculated for $C_{41}H_{45}ClF_5N_2O_5S$ [M+H]$^+$ 807.26. found 807.29.

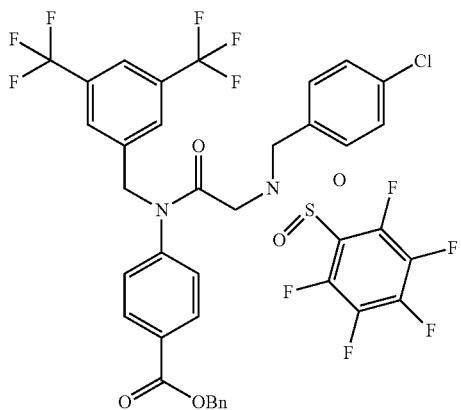

Benzyl-4-(N-(3,5-bis(trifluoromethyl)benzyl)-2-((N-(4-chlorobenzyl)-2,3,4,5,6-pentafluorophenyl)sulfonamido)acetamido)benzoate (6h)

Derivative 6h synthesized using general procedure h (89%): $^1$H NMR (400 MHz, Chloroform-d) δ 0.81-0.94 (m, 1H), 1.21-1.32 (m, 3H), 2.04 (s, 1H), 3.46 (s, 1H), 3.79 (s, 3H), 4.13 (dt, J=14.3, 7.6 Hz, 1H), 4.55 (d, J=17.3 Hz, 2H), 4.62 (s, 4H), 4.87 (s, 5H), 5.32 (d, J=18.0 Hz, 6H), 6.86 (d, J=8.1 Hz, 5H), 7.17 (d, J=8.3 Hz, 6H), 7.23-7.33 (m, 7H), 7.33-7.46 (m, 15H), 7.57 (s, 5H), 7.81 (d, J=9.5 Hz, 4H), 7.90 (d, J=8.6 Hz, 1H), 8.02 (d, J=8.2 Hz, 5H). $^{13}$C NMR (101 MHz, Chloroform-d) δ 46.75, 47.54, 50.35, 52.41, 65.94, 67.11, 111.72, 119.44, 121.50, 121.87, 124.21, 127.04, 127.51, 127.84, 128.14, 128.35, 128.39, 128.42, 128.52, 129.03, 129.82, 131.07, 131.45, 131.62, 131.79, 132.12, 132.40, 134.48, 135.32, 138.44, 143.28, 164.65, 166.42. LRMS (ESI+) calculated for $C_{38}H_{25}ClF_{11}N_2O_5S$ [M+H]$^+$ 865.09. found 865.12.

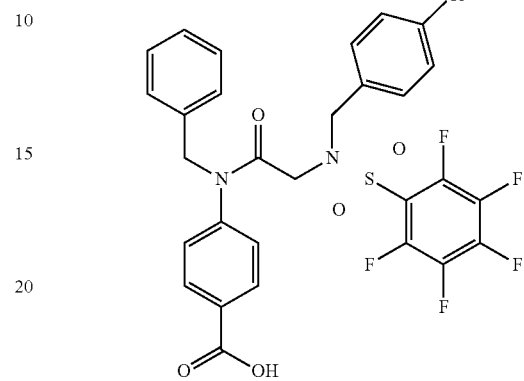

Benzyl-4-(2-((N-(4-chlorobenzyl)-2,3,4,5,6-pentafluorophenyl)sulfonamido)-N-(3-cyanobenzyl)acetamido)benzoate (6i)

Derivative 6i synthesized using general procedure h (63%): $^1$H NMR (400 MHz, Chloroform-d) δ 1.20-1.29 (m, 2H), 2.03 (s, 2H), 3.77 (s, 2H), 4.11 (q, J=7.1 Hz, 1H), 4.62 (s, 2H), 4.76 (s, 3H), 5.34 (s, 3H), 6.85 (d, J=8.1 Hz, 3H), 7.18 (d, J=8.2 Hz, 3H), 7.28 (d, J=8.3 Hz, 3H), 7.30-7.46 (m, 12H), 7.58 (dq, J=7.8, 1.2 Hz, 2H), 8.00 (d, J=8.2 Hz, 3H). $^{13}$C NMR (101 MHz, Chloroform-d) δ 47.66, 50.48, 52.47, 67.08, 112.71, 127.66, 128.16, 128.34, 128.52, 129.00, 129.46, 129.83, 130.90, 131.62, 131.67, 131.83, 132.51, 132.81, 134.37, 135.35, 136.39, 137.35, 143.34, 164.71, 166.15. LRMS (ESI+) calculated for $C_{37}H_{26}ClF_5N_3O_5S$ [M+H]$^+$ 754.11. found 754.14.

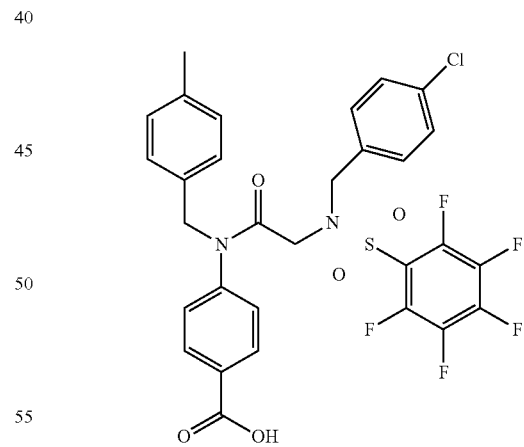

4-(N-benzyl-2-((N-(4-chlorobenzyl)-2,3,4,5,6-pentafluorophenyl)sulfonamido)acetamido)benzoic acid (7a)

Derivative 7a synthesized using general procedure i (45%): $^1$H NMR (400 MHz, Chloroform-d) δ 3.75 (s, 2H), 4.65 (s, 2H), 4.74 (s, 2H), 6.68-6.90 (m, 2H), 6.90-7.14 (m, 2H), 7.19 (d, J=8.2 Hz, 2H), 7.26-7.41 (m, 5H), 7.98 (d, J=8.1 Hz, 2H), 11.25 (s, 1H). $^{13}$C NMR (101 MHz, Chloroform-d) δ 20.66, 47.64, 50.50, 53.22, 127.86, 127.96, 128.04, 128.47, 128.52, 128.64, 128.80, 128.96, 129.93, 131.83, 131.99, 132.61, 134.33, 135.52, 143.38, 143.46, 144.33, 165.69, 170.43.

4-(2-((N-(4-chlorobenzyl)-2,3,4,5,6-pentafluorophenyl)sulfonamido)-N-(4-methylbenzyl)acetamido)benzoic acid (7b)

Derivative 7b synthesized using general procedure i (53%): $^1$H NMR (400 MHz, Chloroform-d) δ 2.11 (s, 6H), 2.33 (s, 3H), 3.74 (s, 1H), 4.70 (s, 4H), 6.77 (d, J=8.1 Hz, 1H), 6.80-6.95 (m, 3H), 7.08 (d, J=7.7 Hz, 2H), 7.16-7.35 (m, 5H), 7.96 (dd, J=22.4, 8.1 Hz, 2H). $^{13}$C NMR (101 MHz, Chloroform-d) δ 20.64, 20.97, 47.62, 50.51, 51.04, 52.87, 128.03, 128.34, 128.51, 128.67, 128.78, 128.95, 129.14, 129.92, 131.66, 131.79, 132.57, 133.98, 137.64, 144.46, 165.70, 170.35, 177.40. HRMS (ESI−) calculated for [$C_{30}H_{21}ClF_5N_2O_6S$]⁻ 651.0785. found 651.0791.

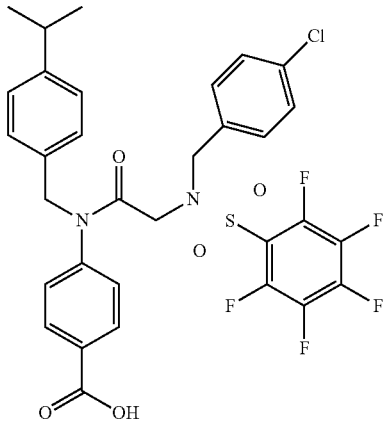

4-(2-((N-(4-chlorobenzyl)-2,3,4,5,6-pentafluorophenyl)sulfonamido)-N-(4-isopropylbenzyl)acetamido)benzoic acid (7c)

Derivative 7c synthesized using general procedure i (69%): ¹H NMR (400 MHz, Chloroform-d) δ 1.24 (dd, J=11.6, 7.0 Hz, 7H), 2.06 (d, J=18.9 Hz, 2H), 2.80-2.94 (m, 1H), 3.47 (s, 6H), 3.72 (s, 1H), 4.11 (q, J=7.1 Hz, 1H), 4.63 (s, 2H), 4.68 (s, 2H), 6.81 (d, J=8.1 Hz, 1H), 6.94 (dd, J=7.9, 4.0 Hz, 2H), 7.15 (dd, J=19.3, 8.0 Hz, 3H), 7.23-7.33 (m, 2H), 7.88-8.00 (m, 2H). ¹³C NMR (101 MHz, Chloroform-d) δ 14.00, 20.59, 20.87, 23.74, 33.63, 47.62, 50.48, 50.50, 52.97, 53.26, 60.33, 77.08, 116.11, 116.26, 126.49, 127.93, 128.53, 128.66, 128.75, 128.93, 129.94, 130.22, 131.55, 131.67, 132.63, 132.88, 134.29, 136.40, 138.94, 142.39, 143.43, 144.13, 144.99, 146.04, 148.68, 165.54, 169.00, 171.22, 176.02. HRMS (ESI−) calculated for [$C_{32}H_{25}ClF_5N_2O_5S$]⁻ 679.1098. found 679.1105.

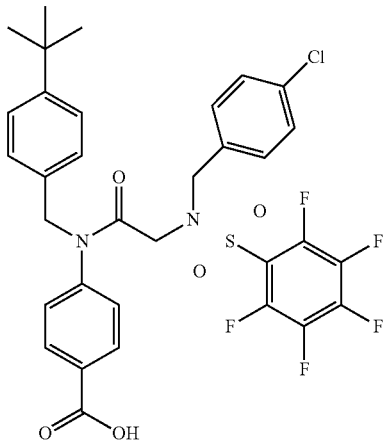

4-(N-(4-(tert-butyl)benzyl)-2-((N-(4-chlorobenzyl)-2,3,4,5,6-pentafluorophenyl)sulfonamido)acetamido)benzoic acid (7d)

Derivative 7d synthesized using general procedure i (63%): ¹H NMR (400 MHz, Chloroform-d) δ 1.30 (s, 9H), 3.65-3.82 (s, 2H), 4.65 (s, 2H), 4.69 (s, 2H), 6.84 (d, J=7.1 Hz, 2H), 6.95 (d, J=7.8 Hz, 2H), 7.17 (s, 2H), 7.27 (dd, J=13.5, 7.9 Hz, 5H), 7.97 (s, 1H), 10.22 (s, 1H). ¹³C NMR (101 MHz, Chloroform-d) δ 31.12, 34.39, 47.63, 50.48, 52.95, 116.12, 125.35, 127.95, 128.22, 128.93, 129.96, 131.79, 132.49, 132.65, 134.27, 143.50, 144.24, 165.61. HRMS (ESI−) calculated for [$C_{33}H_{27}ClF_5N_2O_5S$]⁻ 693.1255. found 693.1270.

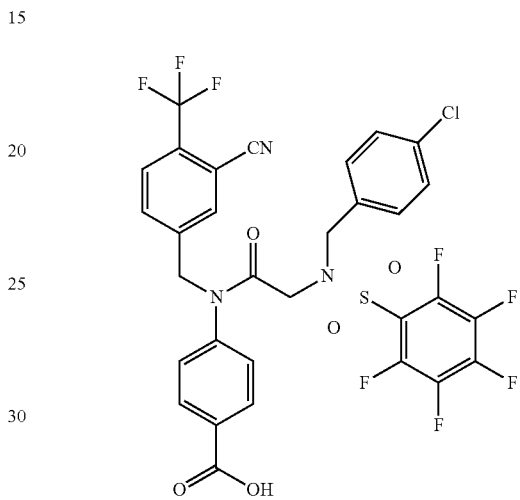

4-(2-((N-(4-chlorobenzyl)-2,3,4,5,6-pentafluorophenyl)sulfonamido)-N-(4-(trifluoromethyl)benzyl)acetamido)benzoic acid (7e)

Derivative 7e synthesized using general procedure i (95%): ¹H NMR (400 MHz, Methanol-d₄) δ 3.87 (s, 2H), 4.61 (s, 2H), 4.86 (s, 2H) 7.02 (d, J=8.0 Hz, 2H), 7.21-7.35 (m, 7H), 7.58 (d, J=7.9 Hz, 2H), 7.95 (dd, J=8.4, 1.5 Hz, 2H). ¹³C NMR (101 MHz, MeOD) δ 47.91, 50.61, 52.16, 124.91, 124.95, 127.68, 128.45, 128.68, 129.83, 130.94, 131.03, 131.09, 131.18, 131.50, 133.29, 133.78, 140.61, 166.49, 166.83. HRMS (ESI−) calculated for [$C_{30}H_{18}ClF_8N_2O_5S$]⁻ 705.0503. found 705.0513.

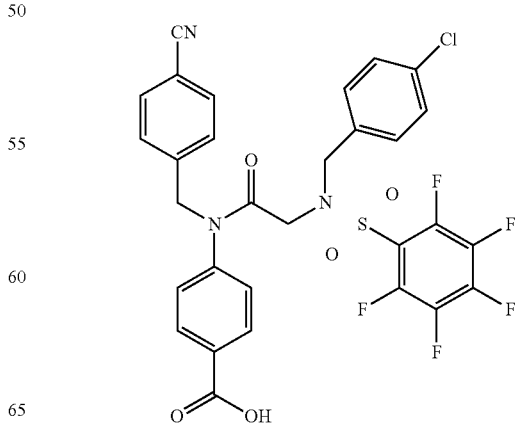

4-(2-((N-(4-chlorobenzyl)-2,3,4,5,6-pentafluorophenyl)sulfonamido)-N-(4-cyanobenzyl)acetamido)benzoic acid (7f)

Derivative 7f synthesized using general procedure i (54%): $^1$H NMR (400 MHz, Chloroform-d) δ 0.86 (t, J=10.5 Hz, 4H), 1.25 (s, 10H), 1.42 (s, 2H), 2.10 (s, 7H), 3.78 (s, 3H), 4.59-4.67 (m, 4H), 4.78 (s, 4H), 6.80 (d, J=8.0 Hz, 2H), 6.89 (d, J=7.9 Hz, 3H), 7.18 (dd, J=8.4, 2.4 Hz, 7H), 7.29 (dd, J=18.1, 10.1 Hz, 12H), 7.59 (d, J=7.9 Hz, 6H), 7.77 (s, 1H), 7.99 (dd, J=22.5, 7.9 Hz, 6H). $^{13}$C NMR (101 MHz, Chloroform-d) δ 20.72, 22.53, 29.54, 47.66, 50.54, 51.04, 52.90, 77.07, 112.00, 116.09, 118.14, 127.68, 128.48, 128.61, 128.83, 129.00, 129.05, 129.85, 131.97, 132.10, 132.33, 132.36, 132.45, 133.78, 134.46, 136.37, 138.95, 140.85, 140.97, 143.44, 143.83, 145.95, 166.22, 166.32, 169.86, 177.13. HRMS (ESI−) calculated for [$C_{30}H_{18}ClF_5N_3O_5S$]$^-$ 662.0581. found 662.0590.

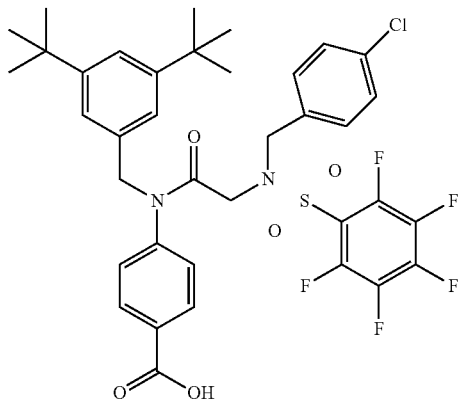

4-(2-((N-(4-chlorobenzyl)-2,3,4,5,6-pentafluorophenyl)sulfonamido)-N-(3,5-di-tert-butylbenzyl)acetamido)benzoic acid (7g)

Derivative 7g synthesized using general procedure i (78%): $^1$H NMR (400 MHz, Chloroform-d) δ 1.24 (d, J=1.1 Hz, 10H), 4.62 (s, 1H), 4.75 (s, 1H), 6.77 (d, J=8.0 Hz, 1H), 6.85 (s, 1H), 7.15 (d, J=8.1 Hz, 1H), 7.18-7.28 (m, 2H), 7.28-7.34 (m, 1H), 7.96 (d, J=8.0 Hz, 1H). $^{13}$C NMR (101 MHz, Chloroform-d) δ 31.32, 34.72, 47.87, 50.42, 53.54, 77.21, 121.73, 123.33, 128.41, 129.09, 130.15, 131.74, 132.69, 134.51, 146.24, 151.19, 165.39, 169.84. HRMS (ESI−) calculated for [$C_{37}H_{35}ClF_5N_2O_5S$]$^-$ 749.1881. found 749.1902.

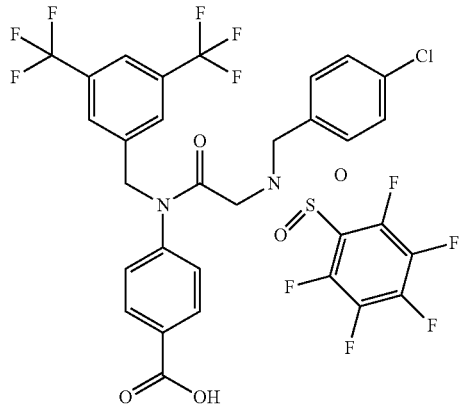

4-(N-(3,5-bis(trifluoromethyl)benzyl)-2-((N-(4-chlorobenzyl)-2,3,4,5,6-pentafluorophenyl)sulfonamido)acetamido)benzoic acid (7h)

Derivative 7h synthesized using general procedure i (86%): $^1$H NMR (400 MHz, Chloroform-d) δ 2.12 (s, 6H), 3.81 (s, 4H), 4.64 (d, J=10.9 Hz, 5H), 4.88 (d, J=2.9 Hz, 6H), 6.78 (d, J=8.1 Hz, 3H), 6.89 (d, J=8.1 Hz, 3H), 7.14-7.25 (m, 6H), 7.25-7.35 (m, 8H), 7.56 (d, J=1.6 Hz, 6H), 7.82 (d, J=6.8 Hz, 4H), 8.01 (dd, J=26.3, 8.2 Hz, 6H). $^{13}$C NMR (101 MHz, Chloroform-d) δ 20.61, 47.54, 50.36, 50.88, 52.40, 52.46, 111.76, 121.48, 121.90, 124.19, 127.66, 128.43, 128.53, 128.61, 128.88, 129.04, 129.85, 130.07, 131.83, 132.12, 132.26, 132.33, 133.66, 138.28, 138.35, 143.90, 144.00, 166.47, 166.56, 170.12, 177.61. HRMS (ESI−) calculated for [$C_{31}H_{17}ClF_{11}N_2O_5S$]$^-$ 773.0377. found 773.0387.

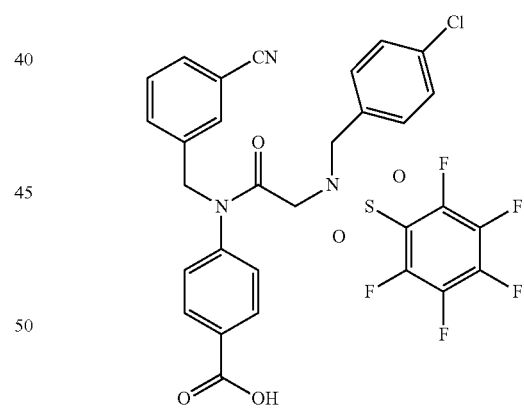

4-(2-((N-(4-chlorobenzyl)-2,3,4,5,6-pentafluorophenyl)sulfonamido)-N-(3-cyanobenzyl)acetamido)benzoic acid (7i)

Derivative 7i synthesized using general procedure i (67%): $^1$H NMR (400 MHz, DMSO-$d_6$) δ 3.96 (s, 2H), 4.55 (s, 2H), 4.84 (s, 2H), 7.25 (t, J=7.6 Hz, 4H), 7.35 (d, J=8.1 Hz, 2H), 7.39-7.51 (m, 2H), 7.58 (s, 1H), 7.69 (dt, J=7.4, 1.6 Hz, 1H), 7.88 (d, J=8.1 Hz, 2H), 13.10 (s, 1H). $^{13}$C NMR (101 MHz, DMSO-$d_6$) δ 28.27, 49.34, 51.31, 51.79, 111.72, 118.86, 128.32, 128.78, 128.29 129.88, 130.35, 131.01, 131.08, 131.11, 131.09, 131.57, 132.90, 133.09, 134.44, 138.51, 166.58, 166.69. HRMS (ESI–) calculated for [$C_{30}H_{18}ClF_5N_3O_5S$]⁻ 662.0581. found 662.0581.

Example 2: DiscoverX Kinase Screen

Figure 1:
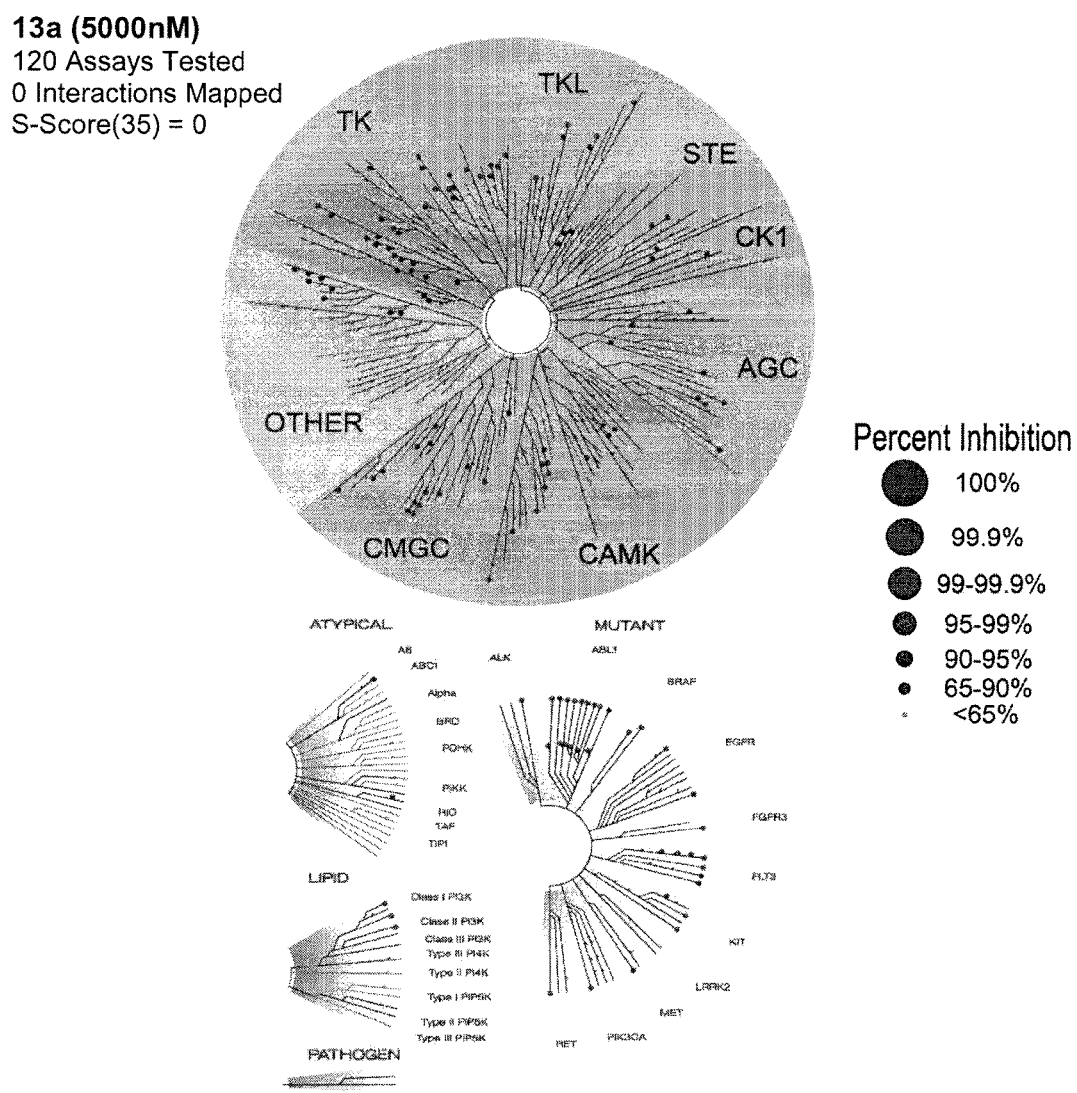
FIG. 1 is a Treespot dendogram demonstrating that a compound of the disclosure does not inhibit the tested kinases (a hit is defined as >35% inhibition)

KINOMEscan kinase profiling was performed as previously described (Fabian et al., 2005; Karaman et al., 2008). For most assays, kinase-tagged T7 phage strains were grown in parallel in 24-well blocks in an *E. coli* host derived from the BL21 strain. *E. coli* were grown to log-phase and infected with T7 phage from a frozen stock (multiplicity of infection=0.4) and incubated with shaking at 32° C. until lysis (90-150 minutes). The lysates were centrifuged (6,000×g) and filtered (0.2 μm) to remove cell debris. The remaining kinases were produced in HEK-293 cells and subsequently tagged with DNA for qPCR detection as previously described (Wodicka et al., 2010). Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining kinases, liganded affinity beads, and test compounds in 1× binding buffer (20% SeaBlock, 0.17×PBS, 0.05% Tween 20, 6 mM DTT). 13a was prepared as 40× stocks in 100% DMSO and directly diluted into the assay. All reactions were performed in polypropylene 384-well plates in a final volume of 0.04 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR and the data presented as % Ctrl (FIG. 1). Data for 13a is also depicted on a TreeSpot dendogram for simplicity (FIG. 1).

Discussion

To determine the selectivity of 13a for STAT5, off-target kinase activity was screened as a possible alternative target for an effector of STAT5 phosphorylation. 13a was assessed against 120 representative kinases covering the diversity of the kinase families (DiscoveRx). Ultrasensitive quantitative PCR (qPCR) was used to measure levels of immobilized kinases after treatment with 13a at 5 μM. 13a showed negligible effects against the bank of kinases and in particular, against upstream STAT5 activating kinases, JAK 1/2, ABL, and FLT-3. These data indicate that the inhibition of STAT5 phosphorylation is due to the interaction with STAT5's SH2 domain and not through inhibition of upstream kinases.

Example 3: Surface Plasmon Resonance (SPR) Studies

Figure 2:
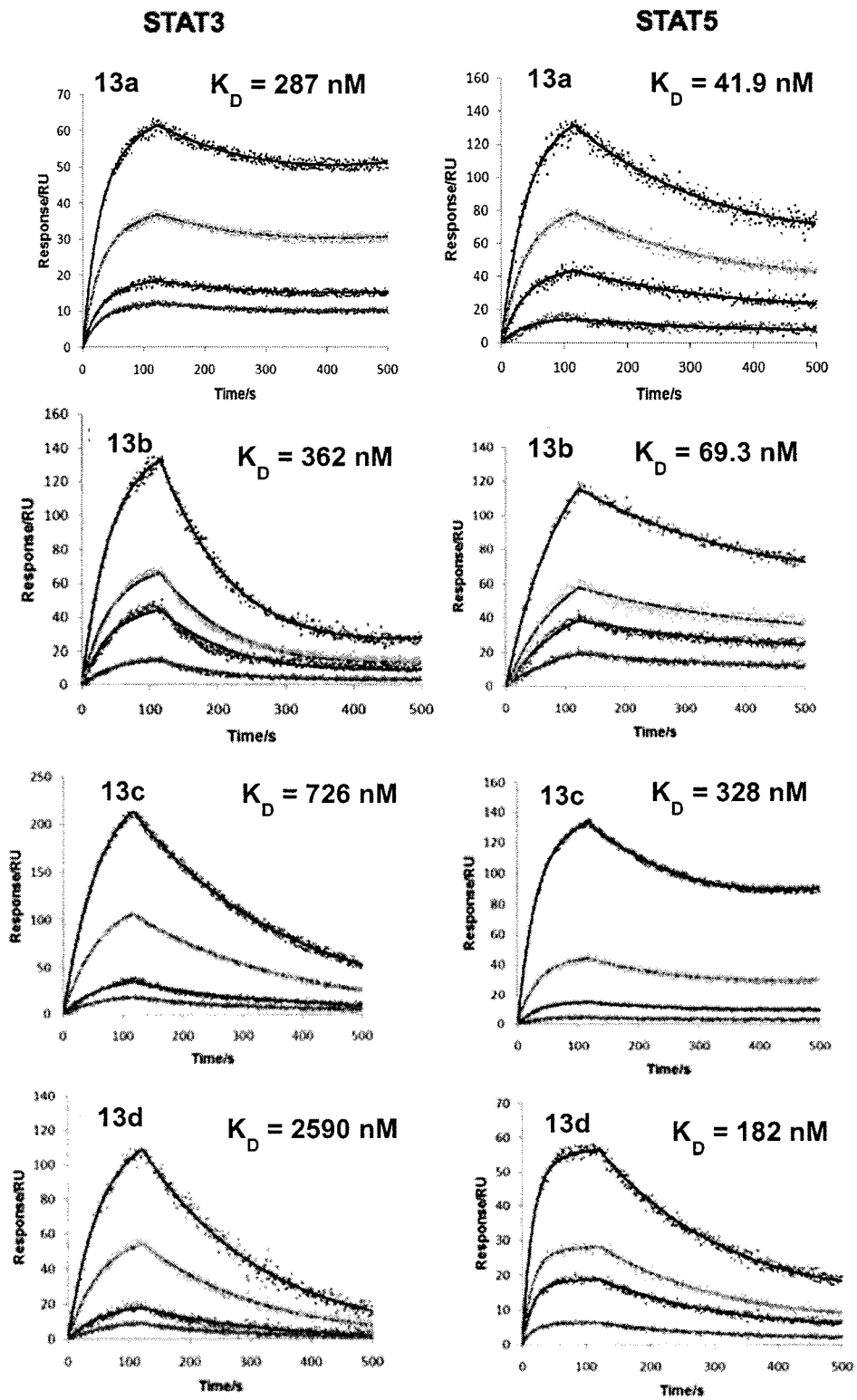
FIG. 2 shows Surface Plasmon Resonance (SPR) curves displaying the binding affinities of compounds of the disclosure against the STAT3 and STAT5 proteins.

Interactions of His-tagged STAT3 and STAT5 with small molecules were investigated using SPR spectroscopy. The binding experiments were carried on a ProteOn XPR36 (Bio-Rad) biosensor at 25° C. using the HTE sensor chip (Bio-Rad, Ontario, Canada). The flow cells of the sensor chip were loaded with a nickel solution at 30 μL/min for 120 s to saturate the Tris-NTA surface with Ni(II) ions. Purified His-tagged STAT3 and STAT5 (SignalChem, British Columbia, Canada) in PBST buffer (PBS with 0.005% (v/v) Tween-20 and 0.001% DMSO pH 7.4) was injected in the first and second channels of the chip respectively, in the vertical direction at a flow rate of 25 μg/μL for 300 s, which attained, on average, ~8000 resonance unit (RU). After a wash with PBST buffer, compounds (13a-d) binding to the immobilized proteins was monitored by injecting a range of concentrations along with a blank at a flow rate of 100 μL/min for 200 s for each of these compounds. When the injection of the compounds was completed, running buffer was allowed to flow over the immobilized substrates for the non-specifically bound inhibitors to dissociate for 600 s. Following dissociation of the compounds, the chip surface was regenerated with an injection of 1 M NaCl at a flow rate of 100 μL/min for 18 s. Interspot channel reference was used for non-specific binding corrections and the blank channel used with each analyte injection served as a double reference to correct for possible baseline drift. Data were analysed using ProteOn Manager Software version 3.1. The Langmuir 1:1 binding model was used to determine the $K_D$ values. Control experiments have already been reported that validates this protocol. Binding experiments were performed at multiple concentrations, 13b,d (5, 1.67, 0.56, 0.19 μM, the top line being 5) and 13c (10, 3.3, 1.1, 0.37 μM, the top line being 10) in FIG. 2.

Discussion

SPR binding experiments were conducted to measure the kinetic association and dissociation using a ProteOn XPR36 (Biorad) with full-length His-tagged, STAT5 and STAT3 (SignalChem) immobilized on a biosensor chip. Inhibitors exhibited nanomolar binding affinities for STAT5, and selectivity for the STAT5 instead of the STAT3 protein. Compound 13a exhibited the most potent $K_D$ ($k_{off}/k_{on}$) of 41.9±4 nM with 7-fold selectivity for STAT5 vs. STAT3, $K_D$=287±29 nM.

Example 4: Fluorescence Polarization Assay

Binding of compounds of the disclosure to the STAT5b SH2 domain was assessed using fluorescence polarization assays similar to those previously reported.[15] Analogous assays were also performed with STAT3 protein to determine the specificity of the compounds (13a-d). Fluorescence assays were performed in flat black 384-well plates (Corning) and fluorescence polarization measurements were taken with the Infinite M1000 machine (Tecan, Crailsheim, Germany). The buffer conditions for all assays were 20 mM HEPES, 50 mM NaCl, 1 mM EDTA, 2 mM dithiothreitol, pH 7.5 and the final DMSO concentration in the wells was kept constant at 10%.

Figure 3:
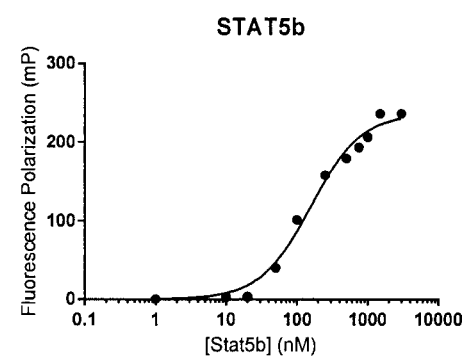
FIG. 3 are calibration curves for wildtype STAT5b and STAT3 protein using fluoresceinated-phosphopeptides (5-FAM-pYLPQTC and 5-FAM-GpYLVLDKW for STAT3 and STAT5B, respectively)
Figure 3:
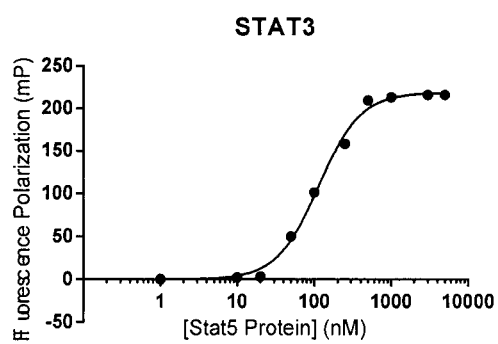

Calibration curves for the wildtype STAT3 and STAT5b proteins were derived by incubating a 10 nM final concentration of fluoresceinated-phosphopeptide (5-FAM-pYLPQTC (SEQ ID NO:1) and 5-FAM-GpYLVLDKW (SEQ ID NO:2) for STAT3 and STAT5B, respectively), which are known to bind the SH2 domains, with increasing concentrations of protein (as shown in FIG. 3). The point at which 80% of the fluoresceinated-phosphopeptide was bound was used as the optimal protein concentration required for the competitive fluorescent polarization assays.

For the STAT5b fluorescence polarization assays, the 5-FAM-GpYLVLDKW (SEQ ID NO:2) peptide and STAT5b protein were first incubated for 30 minutes at room temperature. Compounds were titrated at concentrations ranging from 1->60,000 nM and incubated for a further 15 minutes at which point fluorescence polarization measurements were taken in triplicate. The final well concentrations of the fluoresceinated-phosphopeptide and STAT5B were 10 nM and 250 nM, respectively. The same protocol was used for the analogous STAT3 FP assays, except that the 5-FAM-pYLPQTC (SEQ ID NO:1) peptide was used as a probe and the final STAT3 concentration was 150 nM in each well.

The resulting fluorescence polarization measurements were normalized and plotted against compound concentration on a logarithmic scale. The raw data was fitted with a standard dose-normalized response inhibition curve using GraphPad Prism 6 software. The $IC_{50}$ values were converted to $K_i$ values using Equation 1, which corrects for protein concentration and is a more accurate determination of inhibitory constants in a fluorescence polarization assay than the Cheng-Pruskoff equation.[15] All inhibitory constants and calculated $K_i$ values are summarized in Table 1.

$$K_i = \frac{IC_{50}}{1 + \frac{[Peptide]}{K_d} + \frac{[Protein]}{K_d}}$$

Equation 1:

Modified Cheng-Pruskoff equation containing a correction factor for protein concentration. For STAT5b assays, [Peptide]=10 nM, [Protein]=250 nM, and $K_d$=170 nM. For STAT3 assays, [Peptide]=10 nM, [Protein]=160 nM, and $K_d$=105 nM.

Figure 4:
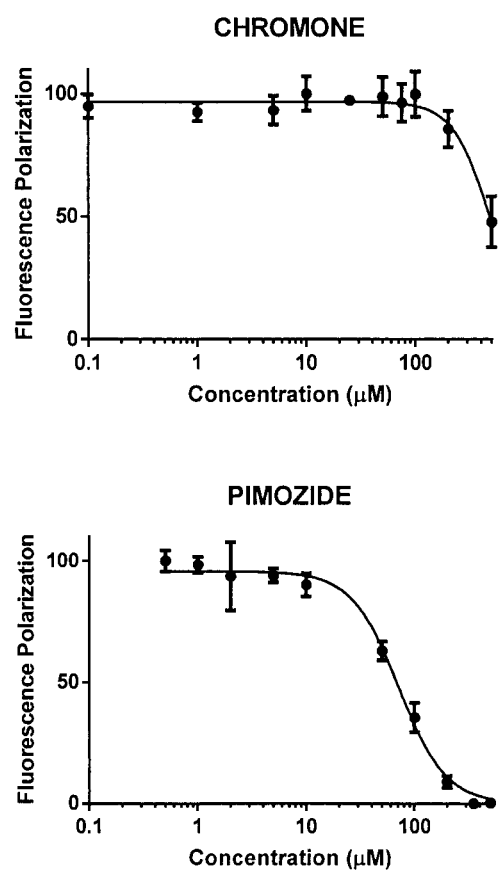
FIG. 4 are normalized Fluorescence Polarization (FP) curves displaying the competitive binding of control STAT5 inhibitors (pimozide and chromone) to wildtype STAT5B protein.
Figure 5:
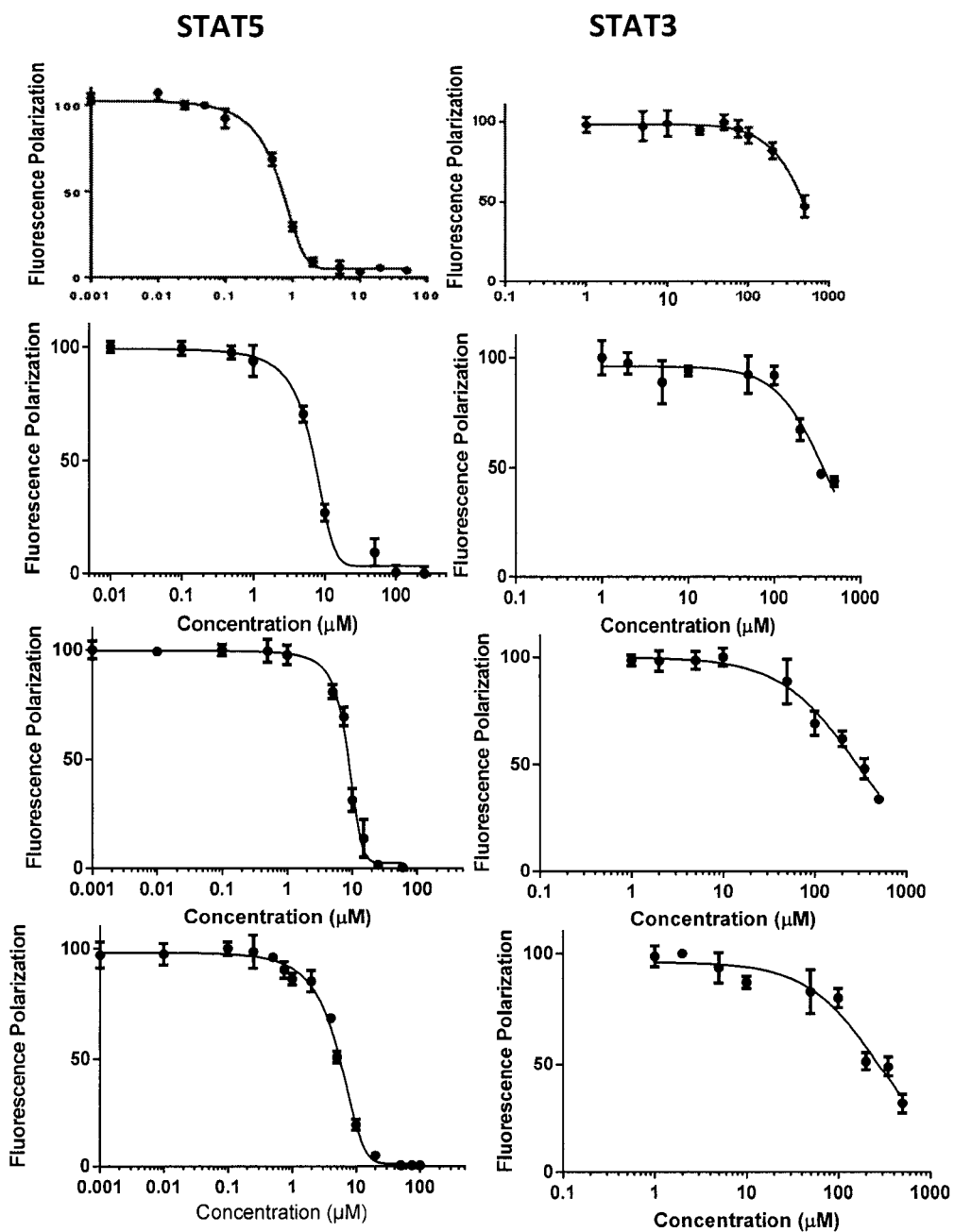
FIG. 5 are normalized FP curves displaying the competitive binding of compounds 13a-d of the disclosure against wildtype STAT5B and STAT3 proteins.

As shown in FIGS. 4 and 5, compounds of the disclosure were evaluated using FP, in which 13a was found to potently disrupt the phosphopeptide-STAT5B interactions, $K_i$=145 nM. Moreover, 13a was a 1000-fold more selective for STAT5B over STAT3, with a STAT3 $K_i$=143 µM.

Example 5: Cell Lines and Culture Techniques

Human erythroleukemia K562 and MV-4-11 cells were cultured in Iscove's modified dulbecco's medium (Gibco) supplemented with 10% FBS (Sigma). Breast carcinoma lines MDA-MB-231 and MDA-MB-468 were grown in dulbecco's modified eagles medium (DMEM) supplemented with 10% FBS (sigma). For downregulation of STAT5 activity, cells were treated with 5, 10, 15, 20 µM of 13a-d STAT5 compounds, for 3 h and 5 h time points. As a control, cells were treated with the DMSO alone.

Figure 6:
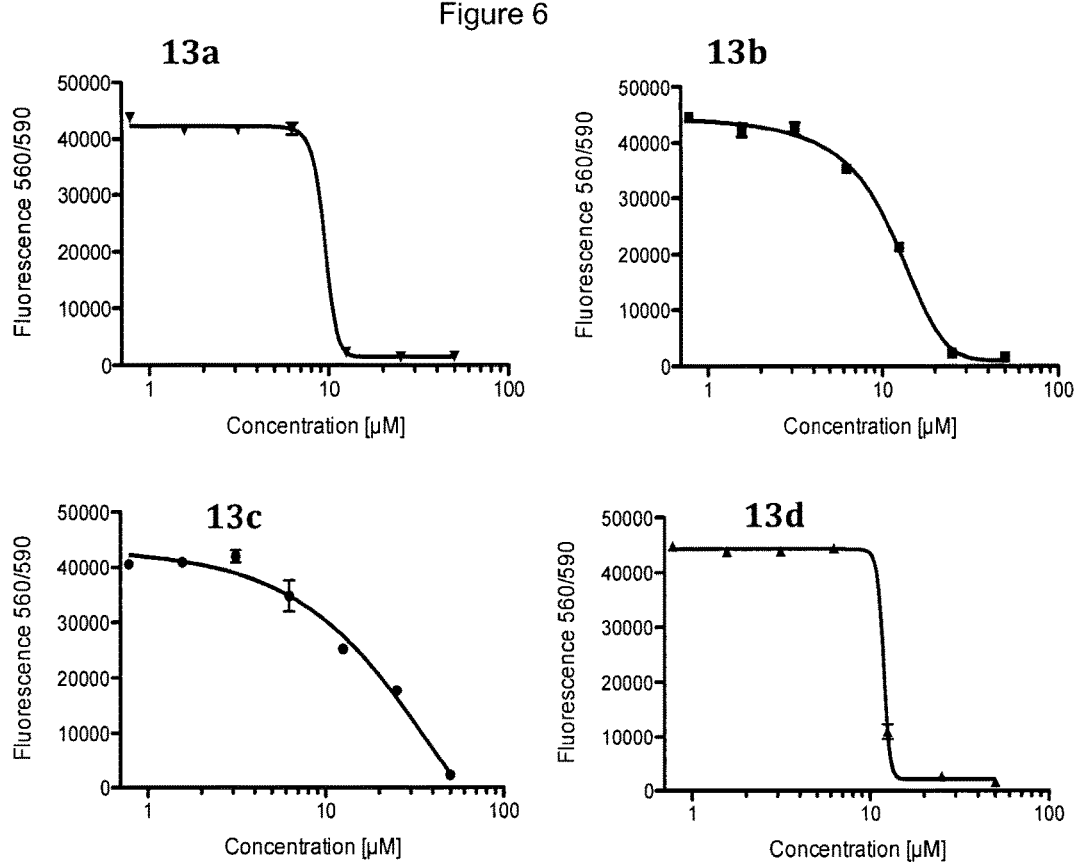
FIG. 6 are graphs showing the cytotoxic potential of compounds 13a-d of the disclosure in K562 cell viability assays.
Figure 7:
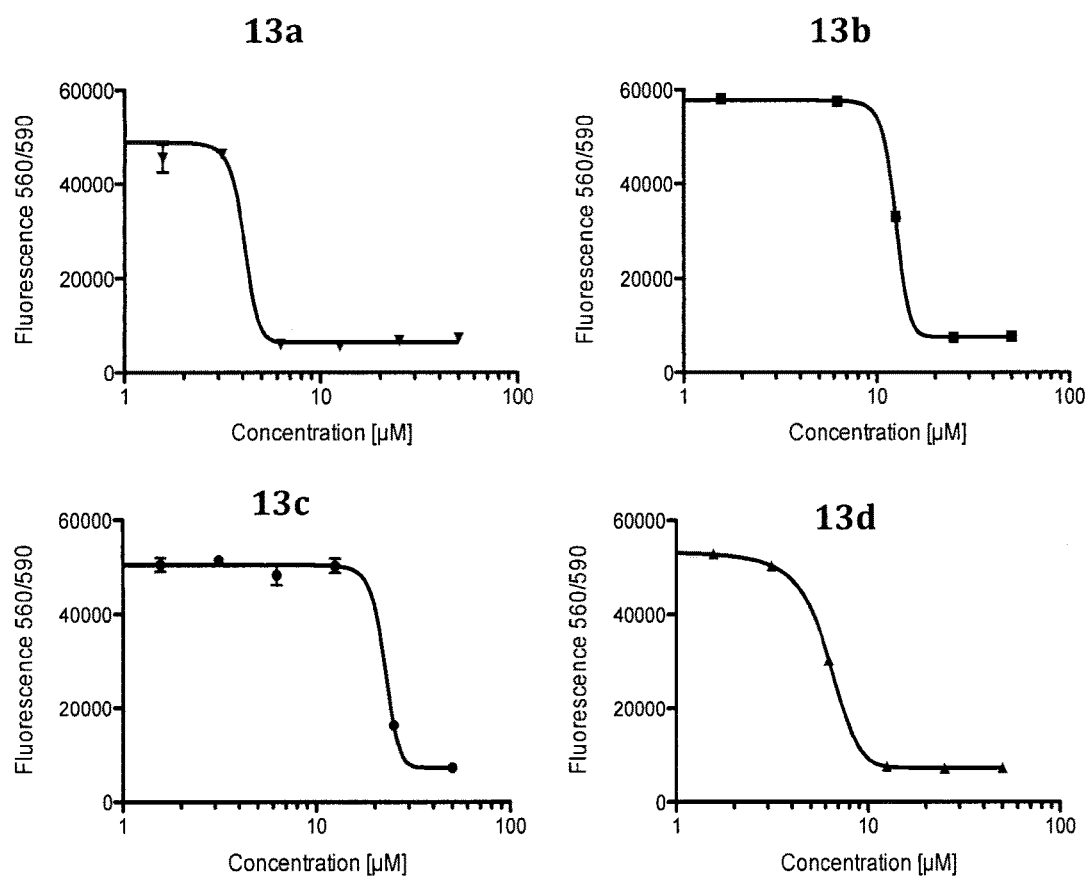
FIG. 7 are graphs showing the cytotoxic potential of compounds 13a-d of the disclosure in MV4-11 cell viability assays.

As shown in FIGS. 6 and 7, 13a was assessed for whole cell potency against STAT5 transformed CML and AML cell lines, K562 (Bcr-Abl) and MV-4; 11 (FLT3-ITD), respectively. Cell viability was assessed following treatment at various concentrations of inhibitor (0.78-50 µM) using a CellTiter-Blue cell viability assay (72 hours). As compared to the STAT5 inhibitors (8j, 8l, 8v, 8x), $IC_{50}$ values for 13a-d were 2-3-fold higher in potency, with activities ranging from 3-20 µM (supporting). 13a, displayed the most potent activity in FLT3-ITD driven MV4; 11 cells, $IC_{50}$=3.5 µM.

Example 6: Western Blotting $1 \times 10^6$ Cells were grown in a 25 cm cell culture flasks (cellstar) and treated with 13a inhibitor. Proteins were extracted using RIPA buffer with protease and phosphates inhibitors and a careful protein determination were preformed (BCA protein assay kit, Pierce). In each assay, 30 µg of clarified whole cell extract were resolved on a 10% polyacrylamide-SDS gel and transferred to a nitrocellulose membrane (Bio-Rad). The membranes were blocked with 5% nonfat milk for at least 1 h followed by an overnight incubation in primary antibody.

Immunodetection was performed using antibodies against the total STAT5 (Cell Signaling #9363), phosphorylated STAT5 (Tyr 694) (Cell Signaling, cat. #9359), total STAT3 (Cell Signaling #4904) and phosphorylated STAT3 (Tyr 705) (Cell Signaling #9661), Cleaved Caspase-3 (Asp175) (Cell Signaling #9661), Cleaved-Parp-1 (ab72805) Anti-Cyclin D1 (Abcam ab16663), Anti-Cyclin-D2 (Abcam ab94685), Anti-c-Myc (Abcam ab32072) and β-actin (Cell Signaling #3700) as a loading control, followed by fluorescent conjugated goat secondary antibodies Alexa Fluor 488 (Cell Signaling #4408) and Alexa Fluor 647.

As shown in FIG. 8, 13a mediated inhibition of STAT5 phosphorylation levels. K652 leukemia cells were treated with 13a for 5 hrs, the cells were harvested, and the levels of phosphorylated STAT5 (Y694) were determined (A). 13a decreased pSTAT5 in a dose dependant manner and ablated pSTAT5 above 10 µM with no change in the total STAT5 concentration or cleavable PARP-1. However, K562 cells were found to undergo cell death (cleaved PARP-1, Caspase-3) at 24 hrs at 15 µM, indicating that 13a induces apoptosis as a result of STAT5 inactivation (B). To investigate selectivity, MDA-MB-231 breast cancer cells, which harbor high pSTAT3 and low pSTAT5 activity, were assessed for differential pSTAT inhibition by 13a. pSTAT3 was not inhibited at doses corresponding to STAT5 inhibition within the leukemic cell line (C). Downstream of STAT5, modulation of the STAT5 transcriptional targets, MCL-1, CYCLIND1/D2 and MYC was assessed. It was reasoned that 13a should decrease gene expression and induce apoptosis by 24 hrs. K562 cells were dosed with 13a at the same concentrations observed for selective STAT5 inhibition. At 5 hrs, dose-dependant decreases in MYC and complete knockdown of MCL-1 was observed at 24 hrs (D).

Example 7—ADME Properties

The metabolic stability of compound 13a was assessed through an ADME profile screen in mouse hepatocytes, as shown in FIGS. 9-13. LC-MS and tandem MS/MS spectra were obtained, illustrating that the presence of metabolites of 13a is minimal and that the majority of intact 13a is recovered after 240 min.

As shown in FIG. 9, compound 13a was assessed for its metabolic stability in mouse hepatocytes and LC-MS spectra were obtained at various time points. Peak 1: 13a conjugated to glutathione+dehydration (MW=1054.2 g/mol). Peak 2: 13a conjugated to glutathione+acetylation+dehydration (MW=1096.3 g/mol). Peak 3: Oxidation of compound 13a (MW=783.2 g/mol). Peak 4: Intact compound 13a (MW=767. Relative peak areas for Peak 1: (<1%), Peak 2: (<1%), Peak 3 (1-10%), Peak 4: (>10%).

FIG. 10 shows a tandem mass spectra (MS/MS) for Peak 1 illustrating fragmentation for the purpose of structure elucidation of compound 13a dehydrated and conjugated to glutathione. FIG. 11 shows a tandem mass spectra (MS/MS) for Peak 2 illustrating fragmentation for the purpose of structure elucidation of compound 13a dehydrated, acetylated and conjugated to glutathione. FIG. 12 shows a tandem mass spectra (MS/MS) for Peak 3 illustrating fragmentation for the purpose of structure elucidation of the oxidation of compound 13a. FIG. 13 shows a tandem mass spectra (MS/MS) for Peak 4 illustrating fragmentation for the parent compound 13a.

Example 8—Effect on CD34+ Cells and MV4-11 AML Cells

Compound 13a was evaluated in healthy human CD34+ umbilical cord cells to determine off-target effects and the therapeutic window. There existed an approximate order of magnitude difference in sensitivity, with little reduction in cell viability at 10 μM of 13a, whilst MV-4; 11 cells were abolished at the same concentrations.

As shown in FIG. 14, compound 13a showed little effect on healthy human CD34+ cells umbilical cord cells at 10 μM with limited effect on cell viability in comparison to MV4; 11 cells.

Example 9—Effect on CML and AML Cells

To investigate selectivity, MDA-MB-231 breast cancer cells, which harbor high pSTAT3 and negligible pSTAT5 activity, FIG. 8c and FIG. 15c, were assessed for differential pSTAT inhibition by 13a. pSTAT3 was not inhibited at doses corresponding to pSTAT5 inhibition within the leukemic cell line and neither total STAT3 or STAT5 protein levels were affected. Furthermore, there were no detectable pSTAT1 levels in both K562 and MDA-MB-231 cells. Correspondingly, 13a did not disrupt the phosphopeptide-STAT1 complex with $IC_{50}$ values of >150 μM, FIG. 15a. It was also shown that 13a was 3-fold less cytotoxic in MDA-MB-231 cells ($IC_{50}$=10 μM) than in the high pSTAT5 leukemic cell line, FIG. 15d.

Previous reports indicate that knockdown of pSTAT5 in leukemia cells abrogates downstream MCL-1 expression at both the mRNA and protein level and is sufficient to induce apoptosis. Furthermore, MCL-1 expression is highly dependent upon STAT5 signaling pathways, suggesting that STAT5 inhibitors might be important for triggering apoptosis in leukemia cells. With selectivity established upstream of the transcription factor, as well as within the STAT family, the downstream effects of pSTAT5 knockdown were investigated, specifically the modulation of the STAT5 transcriptional targets. To confirm the inhibitory effects of 13a, experiments were conducted to measure the changes in level of expression of known STAT5-regulated genes, MCL-1, CYCLIN D1/D2 and MYC in K562 cells.

K562 cells were dosed with 13a at the same concentrations observed for selective pSTAT5 inhibition. After 5 h, dose-dependent decreases in c-MYC expression were observed and complete knockdown of MCL-1 observed at 24 h at 15 μM, which are both consistent with their respective cellular turnover rates, FIG. 8d.

Correspondingly, western blot analysis for protein levels of pSTAT5 and downstream target gene expression were also investigated within the AML cell line, MV-4; 11. Consistent with the CML K562 cell line, 13a at similar concentrations showed dose-dependent decrease of pSTAT5 at 5 h with complete ablation of phosphorylation after 24 h at 10 μM, FIG. 16a. In addition, at 24 h, the initiation of apoptosis was observed, FIG. 16b, as well as complete knockdown of downstream target MCL-1 at 10 μM, FIG. 16c. Overall, 13a had a more pronounced potency within AML than CML cells. These data, in conjunction with the Western blot analysis of pSTAT5, the potent in vitro disruption of STAT5/phosphopeptide complexation (Table 1), the SPR (FIG. 2) and KINOME screen (FIG. 1), and whole cell results (FIGS. 6 and 7), indicate that the STAT5 binding agents inhibit the transcriptional function of STAT5.

Example 9—Metabolic Studies

Primary hepatocytes are popular for drug biotransformation due to their strong resemblance of the in vivo human liver. Intact hepatocytes contain phase I oxidative enzymes as well phase II enzymes like sulfo- and glucuronosyltransferases. Hepatocytes can be generated from various animal species, with the method requiring the whole liver, which may not be available in the case of the human liver. Rather, human liver is obtained from patients that undergo partial liver resection due to liver metastasis. Once isolated, hepatocytes are cryopreserved to maintain the catalytic activity of the metabolic enzymes. Therefore, to understand the physiochemical properties and metabolic profile of 13a, absorption, distribution, metabolism and excretion (ADME) screenings on both s9 fractions and intact hepatocytes were investigated.

The metabolic stability of 13a was evaluated in both pooled human and mouse liver s9 fractions and human and mouse hepatocytes. The concentrations of the parent drug 13a were evaluated by LC-MS/MS to estimate its stability in both reaction systems.

For the pooled s9 fractions, solution of the s9 fraction along with NADPH was added to each well. The negative control did not have NADPH, which was used to exclude the factor from the instability of the drug itself. The positive control used in the assay was Verapamil, a known drug to be metabolized by liver enzymes. The reaction was started by the addition of 13a and performed in duplicate. Aliquots were taken from the reaction solution at 0 min and 60 min. The reaction was stopped by the addition of cold methanol. Samples were then analyzed through LC-MS/MS to determine the metabolic profile. As FIG. 17 illustrates, after 60 min, 13a was recovered at 59.82% in human liver s9 (HLS9) fractions with only 6.96% recovered in mouse liver s9 (MMLS9) fractions. The lower recovery of 13a in MMLS9 vs. HLS9 is due to 1.5 times greater concentration of CPY450 and phase II conjugating enzymes.

13a was then evaluated within intact human and mouse hepatocytes. Like the s9 fractions, Verapamil was used as a positive control in the assay. Cryopreserved hepatocytes were thawed and plated to a working cell density of $0.5 \times 10^6$ viable cell/mL. A portion of the hepatocytes at $0.5 \times 10^6$ viable cell/mL were boiled for 5 min prior to adding to the plate as a negative control to eliminate the enzymatic activity so that little or no substrate turnover should be observed, and to exclude the possibility of instability from 13a itself. Both 13a and verapamil were added and the time points of 0 min and 120 min were taken by the addition of cold methanol to stop the reaction and the remaining percentages of 13a was analyzed through LC-MS/MS. As FIG. 18 shows, 13a is recovered in a significant portion at 68.56% in human hepatocytes in comparison to 53.37% in mouse hepatocytes. As expected, the negative control had higher recoverable rates of 13a at ~85% in both hepatic systems.

Overall, it is apparent that 13a is stable amongst pooled mouse and human s9 fractions as well as hepatocytes. Within these studies, a series of phase I and phase II metabolites within mouse hepatocytes were identified. As FIG. 9 illustrates, 13a is recoverable at >85% after 4 h with three measurable phase I and phase II metabolites. Each peak from the initial mass spectrum is rerun through a tandem mass spec to identify the major peak along with the corresponding fractionation patterns of that metabolite. First, we analyzed the tandem mass spec of peak 4, which confirmed that the parent drug 13a was recovered. Present between 1-10% after 4 h, peak 1 with a major m/z of 1054.2, corresponds to a phase II, glutathione conjugated metabolite of 13a, FIG. 10. Peak 2 on the other hand is a combination of both phase I and phase II metabolism. With a major mass peak at m/z 1096.3, this corresponds to a glutathione-conjugated 13a (m/z 1054.2), which has been further acetylated. Most likely, we deduced the acetylation is occurring at the acid position of the salicylic acid moiety, FIG. 11.

As the major metabolite recovered between 10-20%, peak 3 is a product of phase I metabolism in which 13a (m/z 767.1) has been oxidized to produce the major peak with a m/z of 783.1. Based on the fragmentation pattern, the most likely site of oxidation could reside on the glycine core or the benzyl ring of the salicylic acid, FIG. 12.

Two of the major peaks corresponded to a glutathione derivative of the parent drug 13a, which collectively make up 10% of the metabolites recovered. The stability of 13a under harsher conditions with an excess of the glutathione tripeptide was investigated. Considering the structure of 13a, the pentafluorobenzene is the functional moiety that is likely most susceptible to nucleophilic attack from the GST enzyme. Specifically, the para position is highly electron withdrawn enabling for nucleophilic aromatic substitution to take place. HPLC experiments of 13a with 1000× the concentration of the glutathione tripeptide (10 mM) relative to 13a (100 µM) were run in a phosphate (HEPES) buffer which was chosen based on the solubility of 13a within this buffer system. Data points obtained with the analytical HPLC experiments were fit using ORIGIN software using an exponential decay equation. This equation models for chemical/biological processes whereby a rate in which something happens is proportional to the amount left. Each drug molecule has a certain probability of being metabolized in a small time interval. Thus, as a drug concentration goes down, the rate of its metabolism goes down as well. As FIG. 19 illustrates, 13a (decreasing line) was stable to glutathione conjugation (increasing line) over a time period of 20 h.

TABLE 1

Summary of the $IC_{50}$ values and inhibitory constants ($K_i$) derived from FP binding assays with compounds (13a-d), and the control STAT5 inhibitors (pimozide and chromone).

| Compound | STAT5b | | STAT3 | |
| --- | --- | --- | --- | --- |
| | $IC_{50}$ (µM) | $K_i$ (µM) | $IC_{50}$ (µM) | $K_i$ (µM) |
| 13a | 0.37 | 0.15 | >150 | >60 |
| 13b | 6.53 | 2.57 | >150 | >60 |
| 13c | 8.2 | 3.24 | >150 | >60 |
| 13d | 3.95 | 1.56 | >150 | >60 |
| Pimozide | 75.11 | 29.64 | n/a | n/a |
| Chromone | >150 | >60 | n/a | n/a |

REFERENCES CITED HEREIN AND INCORPORATED BY REFERENCE (1) Hasinoff, B. B., Patel, D. The lack of target specificity of small molecule anticancer kinase inhibitors correlated with their ability to damage myocytes in vitro. *Toxicol. Appl. Pharm.* 2010, 249, 132-39.

(2) Mouhayar, E., Durand, J. B., Cortes, J. Cardiovascular toxicity of tyrosine kinase inhibitors. *Expert. Opin. Drug Saf.* 2013, 12, 687-96.

(3) Yang, B., Papoian, T. Tyrosine kinase inhibitor (TKI)-induced cardiotoxicity: approaches to narrow the gaps between preclinical safety evaluation and clinical outcome. *J. Appl. Toxicol.* 2012, 32, 945-51.

(4) Engelman, J. A., Settleman, J. Acquired resistance to tyrosine kinase inhibitors during cancer therapy. *Curr. Opin. Genet. Dev.* 2008, 18, 73-79.

(5) Barouch-Bentov, R. Mechanisms of Drug-Resistance in Kinases. *Expert. Opin. Inv. Drug.* 2011, 2, 153-208.

(6) Daub, H., Specht, K., Ullrich, A. Strategies to overcome resistance to targeted protein kinase inhibitors. *Nat. Rev. Drug. Discov.* 2004, 3, 1001-10.

(7) Shyh-Han, T., Nevaleinen, M. T. Signal Transducer and Activator of Transcription 5A/B in prostate and breast cancers. *Endocr. Relat. Cancer.* 2008, 15, 367-90.

(8) Becker, S., Groner, B., Muller, C. W. Three-dimensional structure of the Stat3beta homodimer bound to DNA. *Nature.* 1998, 394, 145-51.

(9) Chen, X., Vinkemeier, U., Zhao, Y., Jeruzalmi, D., Darnell J. E., Kuriyan, J. Crystal structure of a tyrosine phosphorylated Stat-1 dimer bound to DNA. *Cell.* 1998, 93, 827-39.

(10) Nosaka, T., Kawashima, T., Misawa, K., Ikuta, K., Mui, A. L., Kitamura, T. STAT5 as a molecular regulator of proliferation, differentiation and apoptosis in hematopoietic cells. *EMBO. J.* 1999, 18, 4754-65.

(11) A) Cumaraswamy, A. A., Todic, A., Resetca, D., Minden, M. D., Gunning, P. T. Inhibitors of Stat5 protein signaling. *Med. Chem. Comm.* 2012, 3, 22-27. B) Cumaraswamy, A. A., Gunning, P. T. Progress towards direct inhibitors of Stat5 protein. *Horm. Mol. Biol. Clin. Invest.* 2012, 10, 281-286.

(12) Muller, J., Sperl, B., Reindl, W., Kiessling, A., Berg, T. Discovery of chromone-based inhibitors of the transcription factor Stat5. *ChemBioChem.* 2008, 9, 723-27.

(13) Nelson, E. A., Walker, S. R., Xiang, M., Weisberg, E., Bar-Natan, M., Barrett, R., Liu, S., Kharbanda, S., Christie, A. L., Nicolais, M., Griffin, J. D., Stone, R. M., Kung, A. L., Frank, D. A. The STAT5 inhibitor pimozide displays efficacy in models of acute myelogenous leukemia driven by FLT3 mutations. *Blood.* 2011, 117, 3421-29.

(14) Walker, S. R., Xiang, M., Frank, D. A. Distinct roles of STAT3 and STAT5 in the pathogenesis and targeted therapy of breast cancer. *Mol. Cell. Endocrinol.* 2014, 382, 616-21.

(15) Muller, J., Schust, J., Berg, T. A high-throughput assay for signal transducer and activator of transcription 5b based on fluorescence polarization. *Anal. Biochem.* 2008, 375, 249-54.

(16) Page, B. D., Khoury, H., Laister, R. C., Fletcher, S., Vellozo, M., Manzoli, A., Yue, P., Turkson, J., Minden, M. D., Gunning, P. T. Small molecule STAT5-SH2 domain inhibitors exhibit potent antileukemia activity. *J. Med. Chem.* 2012, 55, 1047-55.

(17) Andricopulo, A. D., Salum, L. B., Abraham, D. J. Structure-based drug design strategies in medicinal chemistry. *Curr. Top. Med. Chem.* 2009, 9, 771-90.

(18) Kraskouskaya, D., Duodu, E., Arpin, C. C., Gunning, P. T. Progress towards the development of SH2 domain inhibitors. *Chem. Soc. Rev.* 2013, 42, 3337-70.

The invention claimed is:

1. A compound of the Formula

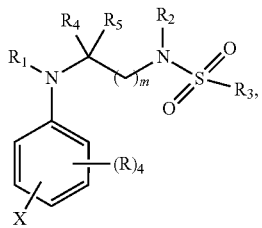

wherein
$R_1$ is —$(CH_2)_n$—$(C_6$-$C_{10})$-aryl or —C(=O)—$(CH_2)_n$—$(C_6$-$C_{10})$-aryl, wherein the aryl groups are optionally substituted with one to five substituents selected from halo, OH, $(C_1$-$C_6)$-alkyl, $(C_1$-$C_6)$-alkoxy, halo-substituted-$(C_1$-$C_4)$-alkyl, -(cyclopropyl)-$CF_3$, —$NO_2$, CN, —$SO_3R'$ and —COOR', wherein R' is H or $(C_1$-$C_4)$-alkyl;
$R_2$ is —$(CH_2)_n$—$(C_6$-$C_{10})$-aryl, wherein the aryl groups are substituted with one to five substituents selected from halo, OH, $(C_1$-$C_6)$-alkyl, $(C_1$-$C_6)$-alkoxy, halo-substituted-$(C_1$-$C_4)$-alkyl, -(cyclopropyl)-$CF_3$, —$NO_2$, CN, —$SO_3R'$ and —COOR', wherein R' is H or $(C_1$-$C_4)$-alkyl;
$R_3$ is —$(CH_2)_n$—$(C_6$-$C_{10})$-aryl, wherein the aryl groups are substituted with one to five halo substituents;
X is —COOR", —P(O)(OR")$_2$, tetrazole, —C(=O)NR"—OH, or —$CF_2$OH, wherein R" is H or $(C_1$-$C_4)$-alkyl or —$CH_2$—$(C_6$-$C_{10})$benzyl;
$R_4$ and $R_5$ are independently or simultaneously H or $CF_3$, wherein one of $R_4$ or $R_5$ is H, or taken together $R_4$ $R_5$ are —C(=O) or —C(=S);
R is H, OH, halo, $(C_1$-$C_6)$-alkyl or $(C_1$-$C_6)$-alkoxy;

n is independently or simultaneously 0, 1, 2, 3, 4, 5, or 6; and m is 1, 2, 3 or 4;

or a pharmaceutically acceptable salt, solvate, prodrug and/or stereoisomer thereof.

2. The compound according to claim 1, wherein $R_1$ is —$(C_6$-$C_{10})$-aryl, —$(CH_2)$—$(C_6$-$C_{10})$-aryl or —C(=O)—$(C_6$-$C_{10})$-aryl.

3. The compound according to claim 2, wherein $R_1$ is phenyl, naphthyl, —$CH_2$-phenyl, —$CH_2$-naphthyl, —C(=O)-phenyl or —C(=O)-naphthyl.

4. The compound according to claim 1, the optional substituents on the aryl group of $R_1$ are selected from one to five of halo, $(C_1$-$C_6)$-alkyl and $(C_1$-$C_6)$-alkoxy.

5. The compound according to 4, the optional substituents on the aryl group of $R_1$ are selected from one to three substituents selected from fluoro, methyl or t-butyl.

6. The compound of claim 1 wherein $R_1$ is —$(CH_2)_n$—$(C_6$-$C_{10})$-aryl or —C(=O)—$(CH_2)_n$—$(C_6$-$C_{10})$-aryl, wherein the aryl groups are optionally substituted with one to five substituents selected from methyl, ethyl, propyl, cyclopropyl, butyl, t-butyl, isobutyl, pentyl, —O-methyl, —O-ethyl, —O-propyl, —O-butyl, —O-isobutyl, —O-pentyl, and OCH$_2$-cyclopropyl.

7. The compound of claim 6 wherein R is —O-$CH_3$, —O-cyclopropyl, —O-cyclopentyl, or cyclopropyl.

8. The compound of claim 6 wherein $R_2$ is —$(CH_2)_n$-$(C_6$-$C_{10})$-aryl, wherein the aryl groups are optionally substituted with one to five substituents selected from F, Cl and $CF_3$.

9. The compound according to claim 1, wherein $R_1$ is

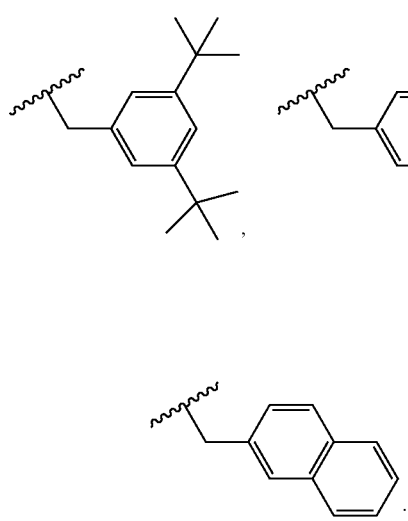

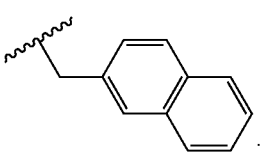

10. The compound according to claim 1, wherein $R_2$ is —or —$(CH_2)$—$(C_6$-$C_{10})$-aryl.

11. The compound according to claim 10, wherein $R_2$ is phenyl or —$CH_2$-phenyl.

12. The compound according to claim 10, wherein the substituents on the aryl group of $R_2$ are selected from one to five of halo, halo-substituted-$(C_1$-$C_4)$-alkyl, -(cyclopropyl)-$CF_3$, —$NO_2$, CN, —$SO_3R'$ and —$COOR'$, wherein $R'$ is H or $(C_1$-$C_4)$-alkyl.

13. The compound according to claim 12, wherein the substituents on the aryl group of $R_2$ are one to three chloro groups.

14. The compound according to claim 1, wherein $R_3$ is —$(C_6$-$C_{10})$-aryl or —$(CH_2)$—$(C_6$-$C_{10})$-aryl, and wherein the aryl is substituted with one to five halo substituents.

15. The compound according to claim 1, wherein R is H, OH, fluoro, chloro, bromo, or $(C_1$-$C_4)$-alkyl.

16. The compound according to claim 1, wherein X is COOR", wherein R" is H or $(C_1$-$C_4)$-alkyl.

17. The compound according to claim 1, wherein the compound has the following structure:

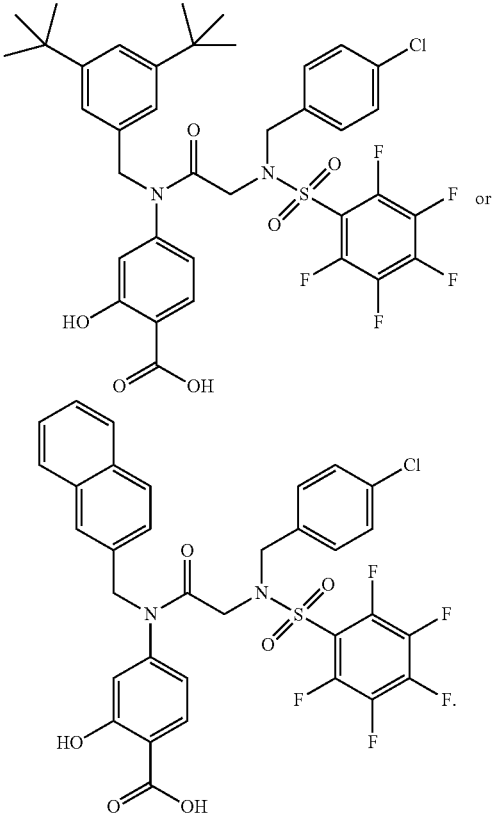

18. A method for the treatment of a disease or condition mediated by signal transducer and activator of transcription 5 (STAT5) protein, comprising administering a pharmaceutically effective amount of a compound of claim 1 to a subject in need thereof.

19. A method for the treatment of hematopoietic malignancies, skin conditions, non-melanoma skin cancer, prostate cancer or inflammation, the method comprising administering a pharmaceutically effective amount of a compound of claim 1 to a subject in need thereof.

20. The method of claim 19, wherein the hematopoietic malignancies is leukemia.

21. The method of claim 19, wherein the skin condition is psoriasis or dermatitis.

* * * * *

SEQUENCE LISTING

<160> NUMBER OF SEQ ID NOS: 2

<210> SEQ ID NO 1

```
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa=5-FAM-pTyr

<400> SEQUENCE: 1

Xaa Tyr Leu Pro Gln Thr Cys
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa=5-FAM-pTyr

<400> SEQUENCE: 2

Gly Xaa Tyr Leu Val Leu Asp Lys Trp
1               5
```